US008642567B2

(12) United States Patent
Ip et al.

(10) Patent No.: US 8,642,567 B2
(45) Date of Patent: Feb. 4, 2014

(54) RECEPTOR MODULATORS EXHIBITING NEUROPROTECTIVE AND MEMORY ENHANCING ACTIVITIES

(75) Inventors: Nancy Yuk-Yu Ip, Hong Kong (CN); Fanny Chui-Fun Ip, Hong Kong (CN); Yueqing Hu, Hong Kong (CN); Wen Cai Ye, Guangzhou (CN)

(73) Assignee: The Hong Kong University of Science and Technology, Kowloon, Hong Kong (CN)

( * ) Notice: Subject to any disclaimer, the term of this patent is extended or adjusted under 35 U.S.C. 154(b) by 234 days.

(21) Appl. No.: 12/616,094

(22) Filed: Nov. 10, 2009

(65) Prior Publication Data

US 2010/0222286 A1      Sep. 2, 2010

Related U.S. Application Data

(63) Continuation of application No. PCT/CN2008/000348, filed on Feb. 14, 2008.

(60) Provisional application No. 60/917,562, filed on May 11, 2007.

(51) Int. Cl.
| C07J 63/00 | (2006.01) |
| A61K 31/573 | (2006.01) |
| C07J 1/00 | (2006.01) |
| A61K 31/58 | (2006.01) |
| C07D 317/14 | (2006.01) |
| C07H 15/24 | (2006.01) |

(52) U.S. Cl.
USPC ............. 514/26; 514/172; 514/177; 514/182; 536/6; 549/454; 549/554; 552/603

(58) Field of Classification Search
USPC ......... 514/26, 172, 177, 182; 536/6; 549/454, 549/455; 552/603
See application file for complete search history.

(56) References Cited

U.S. PATENT DOCUMENTS 4,252,951 A * 2/1981 Jackson et al. ................ 540/220
6,689,767 B2   2/2004 Krasutsky et al.

FOREIGN PATENT DOCUMENTS

| CN | 1784215 A | 6/2006 | |
| CN | 1861627 A * | 11/2006 | ............... C07J 63/00 |
| JP | 2006-151902 A | 6/2006 | |
| WO | WO 98/24795 A1 | 6/1998 | |
| WO | WO 99/09043 A1 | 2/1999 | |
| WO | WO 02/26761 * | 4/2002 | ............... C07J 63/00 |
| WO | WO 02/26761 A1 | 4/2002 | |

OTHER PUBLICATIONS

Wolff, Manfred E. "Burger's Medicinal Chemistry, 5ed, vol. I", John Wiley & Sons, 1995, pp. 975-977.*
Banker, G.S. et al, "Modern Pharmaceutics, 3ed.", Marcel Dekker, New York, 1996, pp. 451 and 596.*
Chem. Comm. 2005, 29, 3635-3645.*
Kuo et al J. Chinese Chem. Soc., 2002, 49, 427-431.*
Bi et al, Bioorganic & Medicinal Chemistry Letters, 2007, 17, 1475-78.*
International Search Report for International Application No. PCT/CN2008/000348 filed on Feb. 14, 2008, 6 pages.
Bang et al., "Antitumor Activity of *Pulsatilla koreana* Saponins and Their Structure-Activity Relationship," Chem. Pharm. Bull., 2005, vol. 53, pp. 1451-1454.
Bi et al., "Synthesis and cytotoxic activity of 17-carboxylic acid modified 23-hydroxy betulinic acid ester derivatives," Bioorganic & Medicinal Chemistry Letters, 2007, vol. 17, pp. 1475-1478.
Lee et al., Bipolar Disorders, 2002, 4, 117-28.
Merck Manual 16th Edn., 1992, pp. 1403-1404, 1488-1489, 1493-1494.
Office Action mailed Jan. 28, 2013, U.S. Appl. No. 13/344,393.

* cited by examiner

*Primary Examiner* — Shaojia Anna Jiang
*Assistant Examiner* — Ganapathy Krishnan
(74) *Attorney, Agent, or Firm* — Kilpatrick Townsend & Stockton LLP

(57) ABSTRACT

The present invention provides therapeutically active compounds and compositions as NMDA and MC receptor antagonists, which are useful in treating central nervous system disorders by over-activation of NMDA and/or MC receptors. In one aspect, the present invention provides methods of enhancing brain's cognitive function and reducing neuronal cell death in mammals and humans.

9 Claims, 22 Drawing Sheets

SEQUENCE LISTING

```
<160> NUMBER OF SEQ ID NOS: 13

<210> SEQ ID NO 1
<211> LENGTH: 7
<212> TYPE: PRT
<213> ORGANISM: Artificial Sequence
<220> FEATURE:
<223> OTHER INFORMATION: synthetic Semax heptapeptide analog of
      adrenocorticotropin fragment (4-10) melanocortin
      receptor MC4 antagonist

<400> SEQUENCE: 1

Met Glu His Phe Pro Gly Pro
 1               5

<210> SEQ ID NO 2
<211> LENGTH: 20
<212> TYPE: DNA
<213> ORGANISM: Artificial Sequence
<220> FEATURE:
<223> OTHER INFORMATION: synthetic real-time PCR brain-derived
      neurotrophic factor (BDNF) forward primer

<400> SEQUENCE: 2
ttgagcacgt gatcgaagag                                              20

<210> SEQ ID NO 3
<211> LENGTH: 20
<212> TYPE: DNA
<213> ORGANISM: Artificial Sequence
<220> FEATURE:
<223> OTHER INFORMATION: synthetic real-time PCR brain-derived
      neurotrophic factor (BDNF) reverse primer

<400> SEQUENCE: 3
ccagcagaaa gagcagagga                                              20

<210> SEQ ID NO 4
<211> LENGTH: 20
<212> TYPE: DNA
<213> ORGANISM: Artificial Sequence
<220> FEATURE:
<223> OTHER INFORMATION: synthetic real-time PCR NT-3 forward primer

<400> SEQUENCE: 4
```
gggggattga tgacaaacac                                          20

<210> SEQ ID NO 5
<211> LENGTH: 20
<212> TYPE: DNA
<213> ORGANISM: Artificial Sequence
<220> FEATURE:
<223> OTHER INFORMATION: synthetic real-time PCR NT-3 reverse primer

<400> SEQUENCE: 5
acaaggcaca cacacaggaa                                          20

<210> SEQ ID NO 6
<211> LENGTH: 20
<212> TYPE: DNA
<213> ORGANISM: Artificial Sequence
<220> FEATURE:
<223> OTHER INFORMATION: synthetic real-time PCR Bcl-2 forward primer

<400> SEQUENCE: 6
ataaccggga gatcgtgatg                                          20

<210> SEQ ID NO 7
<211> LENGTH: 20
<212> TYPE: DNA
<213> ORGANISM: Artificial Sequence
<220> FEATURE:
<223> OTHER INFORMATION: synthetic real-time PCR Bcl-2 reverse primer

<400> SEQUENCE: 7
caggctggaa ggagaagatg                                          20

<210> SEQ ID NO 8
<211> LENGTH: 20
<212> TYPE: DNA
<213> ORGANISM: Artificial Sequence
<220> FEATURE:
<223> OTHER INFORMATION: synthetic real-time PCR c-fos forward primer

<400> SEQUENCE: 8
ggagccggtc aagaacatta                                          20

<210> SEQ ID NO 9
<211> LENGTH: 20
<212> TYPE: DNA
<213> ORGANISM: Artificial Sequence
<220> FEATURE:
<223> OTHER INFORMATION: synthetic real-time PCR c-fos reverse primer

<400> SEQUENCE: 9
tgctgcatag aaggaaccag                                          20

<210> SEQ ID NO 10
<211> LENGTH: 21
<212> TYPE: DNA
<213> ORGANISM: Artificial Sequence
<220> FEATURE:
<223> OTHER INFORMATION: synthetic real-time PCR hypoxanthine
      phosphoribosyltransferase 1 (HPRT1) forward primer

<400> SEQUENCE: 10
tgacactggt aaaacaatgc a                                        21

<210> SEQ ID NO 11
<211> LENGTH: 21
<212> TYPE: DNA
<213> ORGANISM: Artificial Sequence

```
<220> FEATURE:
<223> OTHER INFORMATION: synthetic real-time PCR hypoxanthine
      phosphoribosyltransferase 1 (HPRT1) reverse primer

<400> SEQUENCE: 11
ggtccttttc accagcaagc t                                          21

<210> SEQ ID NO 12
<211> LENGTH: 20
<212> TYPE: DNA
<213> ORGANISM: Artificial Sequence
<220> FEATURE:
<223> OTHER INFORMATION: synthetic real-time PCR glyceraldehyde
      3-phosphate dehydrogenase (GAPDH) forward primer

<400> SEQUENCE: 12
tgcaccacca actgcttagc                                            20

<210> SEQ ID NO 13
<211> LENGTH: 21
<212> TYPE: DNA
<213> ORGANISM: Artificial Sequence
<220> FEATURE:
<223> OTHER INFORMATION: synthetic real-time PCR glyceraldehyde
      3-phosphate dehydrogenase (GAPDH) reverse primer

<400> SEQUENCE: 13
ggcatggact gtggtcatga g                                          21
```

RECEPTOR MODULATORS EXHIBITING NEUROPROTECTIVE AND MEMORY ENHANCING ACTIVITIES

CROSS-REFERENCES TO RELATED APPLICATIONS

This application is a continuation application of PCT Patent Application No. PCT/CN2008/000348, filed Feb. 14, 2008, which claims priority to U.S. Provisional Patent Application No. 60/917,562 filed May 11, 2007; the disclosures of each is hereby incorporated by reference in its entirety and for all purposes.

BACKGROUND OF THE INVENTION

N-methyl-D-aspartate (NMDA) receptors are ligand-gated ion channels located primarily within the central nervous system (CNS). They belong to the family of ionotropic glutamate receptors and exist as multiple subtypes due to the different combinations of subunits—NR1, NR2 (NR2A, NR2B, NR2C, NR2D) and NR3—that can be expressed. In addition to the agonist binding site, NMDA receptors have multiple distinct binding sites for various compounds that enhance, modulate and inhibit the activation of the receptors.

It is known that NMDA receptors are involved in neuronal communication and play important roles in synaptic plasticity and mechanisms that underlie learning and memory. Under normal conditions, NMDA receptors engage in synaptic transmission via the neurotransmitter glutamate, which regulates and refines synaptic growth and plasticity. However, when there are abnormally high levels of glutamate (i.e. under pathological conditions), NMDA receptors become over-activated, resulting in an excess of $Ca^{2+}$ influx into neuronal cells, which in turn causes excitotoxicity and the activation of several signaling pathways that trigger neuronal apoptosis. Glutamate-induced apoptosis in brain tissue also accompanies oxidative stress resulting in loss of ATP, loss of mitochondrial membrane potential, and the release of reactive oxygen species and reactive nitrogen species (e.g. $H_2O_2$, NO, $OONO^-$, $O_2^-$) causing associated cell damage and death. Decreased nerve cell function and neuronal cell death eventually occur. Excitotoxicity also occurs if the cell's energy metabolism is compromised.

Over-activation of the NMDA receptors is implicated in neurodegenerative diseases and other neuro-related conditions as it causes neuronal loss and cognitive impairment, and also plays a part in the final common pathway leading to neuronal injury in a variety of neurodegenerative disorders such as amyotrophic lateral sclerosis, Parkinson's disease, Alzheimer's disease and Huntington's disease, as well as conditions such as stroke. Recent findings have implicated NMDA receptors in many other neurological disorders, such as multiple sclerosis, cerebral palsy (periventricular leukomalacia), and spinal cord injury, as well as in chronic and severe mood disorders (Mathew S J et al., *Rev Bras Psiquiatr*, 27:243-248 (2005)).

NMDA receptors have played crucial roles in both regulating and promoting normal nervous system functions as well as in causing cell-death, which leads to lethal conditions. There has been increasing evidence that the type of signal given to a cell depends on the location of the activated NMDA receptor. Growth and survival-promoting signals result from the activated synaptic NMDA receptors, while cell death causing signals result from the extrasynaptic NMDA receptors. Recent studies also indicate that the activated synaptic NMDA receptors lead to robust phosphorylation of the transcription factor CREB on the transcriptional regulatory residue Ser133 and promote CREB-dependent gene expression and neuronal survival. However, the activated extrasynaptic NMDA receptors transiently phosphorylate CREB and do not activate CREB-dependent gene expression, resulting in neuronal cell death (Hardingham G E et al., *Nat Neurosci*, 5: 405-414 (2002)).

Yet, there are few effective therapeutic agents for excitotoxicity to alleviate symptoms of its associated neuronal disorders. One complication for the development of effective NMDA antagonists as neurotherapeutic drugs is that many NMDA antagonists also exhibit psychotogenic and neurotoxic properties. For example, MK-801 (dizocilpine maleate) is capable of providing certain degree of neuroprotection in ischemic stroke, but is associated with psychotropic and adverse motor effects. Thus, it is desirable to identify and/or to develop compounds that can potentiate NMDA synaptic activity resulting in neuroprotection.

Melanocortins (MC) receptors are a class of G protein coupled receptors. MC are a group of pituitary peptide hormones, which include adrenocorticotropic hormone (ACTH) and the alpha, beta and gamma melanocyte-stimulating hormones (MSH). They are derived from the pro-hormone proopiomelanocortin (Adan et al., (2000) Melanocortins and the brain: from effects via receptors to drug targets. *Eur J Pharmacol* 405: 13-24). MCs act through a multitude of melanocortin receptors designated MC1 through MC5. MC1 receptors are expressed in macrophages and monocytes, keratinocytes and melanocytes, endothelial cells, glioma cells and astrocytes, and pituitary and periaqueductal grey matter, where they are involved in melanogenesis and anti-inflammatory processes (Kang et al., (2006) A selective small molecule agonist of the melanocortin-1 receptor inhibits lipopolysaccharide-induced cytokine accumulation and leukocyte infiltration in mice. *J Leukoc Biol* 80: 897-904; and Slominski et al., (2004) Melanin pigmentation in mammalian skin and its hormonal regulation. *Physiol Rev* 84: 1155-228). They are also found in subcutaneous fat of obese subjects and thought to play a role in the pathophysiology of obesity (Hoch et al., Expression and localization of melanocortin-1 receptor in human adipose tissues of severely obese patients. *Obesity* (Silver Spring) 15: 40-9). ACTH binds to MC2 receptor (ACTH receptor) and mainly expressed in adrenal gland and adrenal cortex. While MC3 is expressed in both periphery and neural tissues, MC4 is mainly found in CNS and is the second neural MC receptor as they are expressed in multiple regions of the brain including the cortex, thalamus, hypothalamus, brainstem, and spinal cord. The receptor is also highly expressed in the paraventricular nucleus and is involved in the modulation of pituitary function. MC5, highly homologous to MC4, is the only MC receptor found in skeletal muscle and is broadly expressed in periphery and present in specific brain regions.

MC4 receptor activity has been linked to neurite outgrowth and peripheral nerve regeneration (Tanabe et al., (2007) Melanocortin receptor 4 is induced in nerve-injured motor and sensory neurons of mouse. *J Neurochem* 101:1145-52; and Adan et al., (1996) Melanocortin receptors mediate alpha-MSH-induced stimulation of neurite outgrowth in neuro 2A cells. *Brain Res Mol Brain Res* 36:37-44), cognitive functions and neuroprotection in brain ischemia stroke (Giuliani et al., 2006), inflammatory responses in astrocytes (Caruso et al., (2007) Activation of melanocortin 4 receptors reduces the inflammatory response and prevents apoptosis induced by lipopolysaccharide and interferon-gamma in astrocytes. *Endocrinology* 148: 4918-26). Studies conducted on the heptapeptide Semax (Met-Glu-His-Phe-Pro-Gly-Pro; SEQ ID NO:1)—an analog of the adrenocorticotropin fragment (4-10) but lack ACTH hormonal activity, is an antagonist for MC4 receptor (Adan et al., (1994) Identification of antagonists for melanocortin MC3, MC4 and MC5 receptors. Eur J Pharmacol 269: 331-7). Semax has been reported to enhance cognitive brain functions by modulating the expression and the activation of the hippocampal BDNF/trkB system (Tsai, (2007) Semax, an analogue of adrenocorticotropin (4-10), is a potential agent for the treatment of attention-deficit hyperactivity disorder and Rett syndrome. *Med Hypotheses* 68: 1144-1146; and Dolotov et al., (2006) Semax, an analogue of adrenocorticotropin (4-10), binds specifically and increases levels of brain-derived neurotrophic factor protein in rat basal forebrain. *J Neurochem* 97 Suppl 1: 82-86). BDNF has long been known for its involvement in learning and memory, modulation of dendritic spine density and morphology, regulation of axonal growth, and various therapeutic strategies for neurological disorders have targeted BDNF (Winckler, (2007) BDNF instructs the kinase LKB1 to grow an axon. *Cell* 129: 459-60; Ji et al., (2005) Cyclic AMP controls BDNF-induced TrkB phosphorylation and dendritic spine formation in mature hippocampal neurons. *Nat Neurosci* 8: 164-72; Pezet et al., (2004) Brain-derived neurotrophic factor as a drug target for CNS disorders. *Expert Opin Ther Targets* 8: 391-399; Yamada et al., (2003) Brain-derived neurotrophic factor/TrkB signaling in memory processes. *J Pharmacol Sci* 91: 267-270). BDNF expression is also linked to stress and depression, and various treatments for depression (such as antidepressants and electroconvulsive therapy) work by inducing BDNF expression in the brain (reviewed in Castren et al., (2007) Role of neurotrophic factors in depression. *Curr Opin Pharmacol* 7: 18-21; Kuipers et al, (2006) Brain-derived neurotrophic factor mechanisms and function in adult synaptic plasticity: new insights and implications for therapy. *Curr Opin Drug Discov Devel* 9: 580-586; and Malberg et al., (2005) Antidepressant action: to the nucleus and beyond. *Trends Pharmacol Sci* 26: 631-638). As such, MC4 receptor antagonism has been postulated as a therapeutic mechanism against depression, anxiety and cachexia (Chaki et al., (2007) Melanocortin-4 receptor antagonists for the treatment of depression and anxiety disorders. *Curr Top Med Chem* 7: 1145-1151; and Foster et al., (2007) Melanocortin-4 receptor antagonists as potential therapeutics in the treatment of cachexia. *Curr Top Med Chem* 7: 1131-1136).

Therefore, there is a need to develop effective NMDA and MC4 antagonists that have high potency and are capable of (i) preventing and/or treating the CNS disorders, such as excitotoxicity, neurodegenerative diseases and neuropathological conditions; (ii) providing neuroprotection under stress conditions, such as a stroke; (iii) enhancing the brain's cognitive functions; and (iv) offering treatment to conditions, such as depression, anxiety, anorexia and cachexia induced by other chronic diseases. The present invention satisfies this and other needs.

BRIEF SUMMARY OF THE INVENTION

In one aspect, the present invention provides a compound of formula (I):

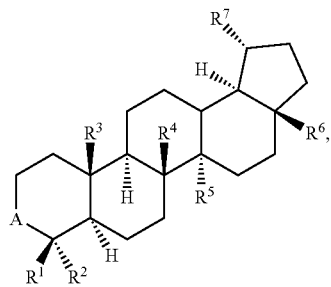

I or a pharmaceutically acceptable salt, prodrug, hydrate, isomer thereof; wherein:

$R^1$, $R^3$, $R^4$ and $R^5$ are each independently $C_{1-4}$alkyl;

$R^2$ is selected from the group consisting of $C_{1-6}$haloalkyl, $C_{3-6}$cycloalkyl, —$X^1$CN, —$X^1$NO$_2$, —$X^1$C(O)$R^a$, —$CR^b$=$NOR^c$, —$X^1$CO$_2R^c$, —$X^1$C(O)NR$^c$R$^d$, —$X^1$C(NR$^c$R$^d$)=NR$^c$, —$X^1$C(O)NR$^c$S(O)R$^d$, —$X^1$C(O)NR$^c$S(O)R$^d$, —$X^1$OR$^e$, $X^1$SR$^e$, —$X^1$NHR$^e$ and —$X^1$N($R^e$)$_2$ and —$X^1R^e$, wherein each $X^1$ is independently a bond or $C_{1-4}$alkylene, wherein $R^e$ is $C_{1-6}$alkyl, haloalkyl, arylC$_{0-6}$ alkyl, or cycloalkyl substituted with from 1-3 members of $R^f$, and wherein $R^a$, $R^b$, $R^c$ and $R^d$ are each independently H, $C_{1-6}$alkyl or aryl-$C_{1-6}$alkyl; wherein the aliphatic portion of each $R^2$ substituent is optionally substituted with from 1-3 $R^f$, wherein $R^f$ is selected from the group consisting of halo, CN, NO$_2$, —OH, —$R^g$, —OR$^g$, —OC(O)NHR$^g$, —OC(O)N($R^g$)$_2$, —OC(O)R$^g$, —OC(O)H, —NH$_2$, —NHR$^g$, —N($R^g$)$_2$, —SH, —SR$^g$, —S(O)$_2R^g$, —SO$_2$NH$_2$, —SO$_2$NHR$^g$, —SO$_2$N($R^g$)$_2$, —NHS(O)$_2R^g$, —NR$^g$S(O)$_2R^g$, —C(O)NH$_2$, —C(O)NHR$^g$, —C(O)N($R^g$)$_2$, —C(O)H, —C(O)R$^g$, —NHC(O)R$^g$, —NR$^g$C(O)R$^g$, —NHC(O)NH$_2$, —NR$^g$C(O)NH$_2$, —NR$^g$C(O)NHR$^g$, —NHC(O)NHR$^g$, —NR$^g$C(O)N($R^g$)$_2$, —NHC(O)N($R^g$)$_2$, —COOH, —CO$_2R^g$, —NHCO$_2R^g$, —NR$^g$CO$_2R^g$ and —OSi($R^g$)$_3$, wherein each $R^g$ is independently a $C_{1-6}$alkyl;

A is selected from the group consisting of C=$Y^1$, C=NOR$^c$, C=NOC(O)H, C=NOC(O)R$^g$, C=NOCO$_2R^g$, C=NOC(O)NH$_2$, C=NOC(O)NHR$^g$, C=NOC(O)N($R^g$)$_2$ and —CR$^c$R$^h$, wherein $Y^1$ is =O or =S, and $R^h$ is selected from the group consisting of halo, CN, NO$_2$, —OH, —OR$^i$, —OC(O)NHR$^i$, —OC(O)N($R^i$)$_2$, —OC(O)R$^i$, —OC(O)H, —NH$_2$, —NHR$^i$, —N($R^i$)$_2$, —SH, —SR$^i$, —S(O)$_2R^i$, —SO$_2$NH$_2$, —SO$_2$NHR$^i$, —SO$_2$N($R^i$)$_2$, —NHS(O)$_2R^i$, —NR$^i$S(O)$_2R^i$, —C(O)NH$_2$, —C(O)NHR$^i$, —C(O)N($R^i$)$_2$, —C(O)H, —C(O)R$^i$, —NHC(O)R$^i$, —NR$^i$C(O)R$^i$, —NHC(O)NH$_2$, —NR$^i$C(O)NH$_2$, —NR$^i$C(O)NHR$^i$, —NHC(O)NHR$^i$, —NR$^i$C(O)N($R^i$)$_2$, —NHC(O)N($R^i$)$_2$, —COOH, —CO$_2R^i$, —NHCO$_2R^i$, —NR$^i$CO$_2R^i$, —OSi($R^i$)$_3$, —O—(Z)$_{1-6}$, —S—(Z)$_{1-6}$, —NH(Z)$_{1-6}$ and —NR$^c$(Z)$_{1-6}$, wherein each $R^i$ is independently a $C_{1-6}$alkyl, $C_{1-6}$haloalkyl, arylC$_{0-6}$alkyl or $C_{3-6}$cycloalkyl, optionally substituted with from 1-3 $R^f$; —(Z)$_{1-6}$ is a sequence of 1-6 independently selected $C_{4-7}$monosaccharide residues linked together through ether bonds, optionally each Z is independently substituted with from 1-3 $C_{1-6}$alkyl or $R^f$;

$R^6$ is selected from the group consisting of $C_{1-6}$haloalkyl, $C_{3-6}$cycloalkyl, —$X^2$CN, —$X^2$NO$_2$, —$X^2$C(O)$R^a$, —$CR^b$=$NOR^c$, —$X^2$OC(O)$R^a$, —$X^2$CO$_2R^c$, —$X^2$C(O)NR$^c$R$^d$, —$X^2$C(NR$^c$R$^d$)=NR$^c$, —$X^2$C(O)NR$^c$S(O)R$^d$, —$X^2$C(O)NR$^c$S(O)R$^d$, —$X^2$OR$^a$, —$X^2$SR$^a$, —$X^2$NHR$^a$ and $X^2$N($R^a$)$_2$, wherein each $X^2$ is independently a bond or $C_{1-4}$alkylene; wherein the aliphatic portion of each $R^6$ substituent is optionally substituted with from 1-3 $R^f$, wherein the two adjacent $R^f$ substituents together with the atoms to which they are attached optionally form a 5-membered heterocyclic ring having from 1-3 heteroatoms selected from N, O or S, wherein the heterocyclic ring is optionally substituted with from 1-3 $R^g$, and the aromatic ring of each $R^6$ is optionally substituted with from 1-5 $R^f$; and $R^7$ is selected from the group consisting of $C_{1-6}$alkyl, $C_{1-6}$haloalkyl, $C_{3-6}$cycloalkyl, $C_{2-6}$alkenyl, $C_{2-6}$haloalkenyl, $C_{5-6}$cycloalkenyl and $C_{2-6}$epoxyalkyl, each of which is optionally substituted with from 1-3 $R^f$, with the proviso that the compounds are other than DA001-003, DA005-006, DA010-011, DA015, DA018 and DA020 as set forth in Table 1. In one embodiment, the present invention provides a pharmaceutical composition comprising compounds of formula I and a pharmaceutically acceptable carriers, excipients or diluents.

In another aspect, the present invention provides a method of inhibiting the activities of an NMDA and/or MC receptor. The method includes contacting compounds of formula I or any of compounds DA001-047 with the NMDA and or MC receptor.

In yet another aspect, the present invention provides methods of preventing and/or treating central nervous system disorders in a subject, such as a mammal or human. In one embodiment, the present invention provides methods for preventing and/or treating a neurodegenerative disease and neuropathological conditions in a mammal. In another embodiment, the present invention provides a method for enhancing the brain's cognitive function in a mammal. In yet another embodiment, the present invention provides a method of preventing neuronal damage under a stress condition, such as a stroke in a mammal. In still another embodiment, the present invention provides a method of treating depression, anxiety and cachexia induced by a chronic disease. The methods for treating and/or preventing CNS disorders in the above embodiments include administering to the mammal a therapeutically effective amount of compounds of formula I or any of compounds DA001-047 or a pharmaceutical composition comprising the compounds of formula I or any of compounds DA001-047.

DETAILED DESCRIPTION OF THE INVENTION

I. Introduction

Figure 1:
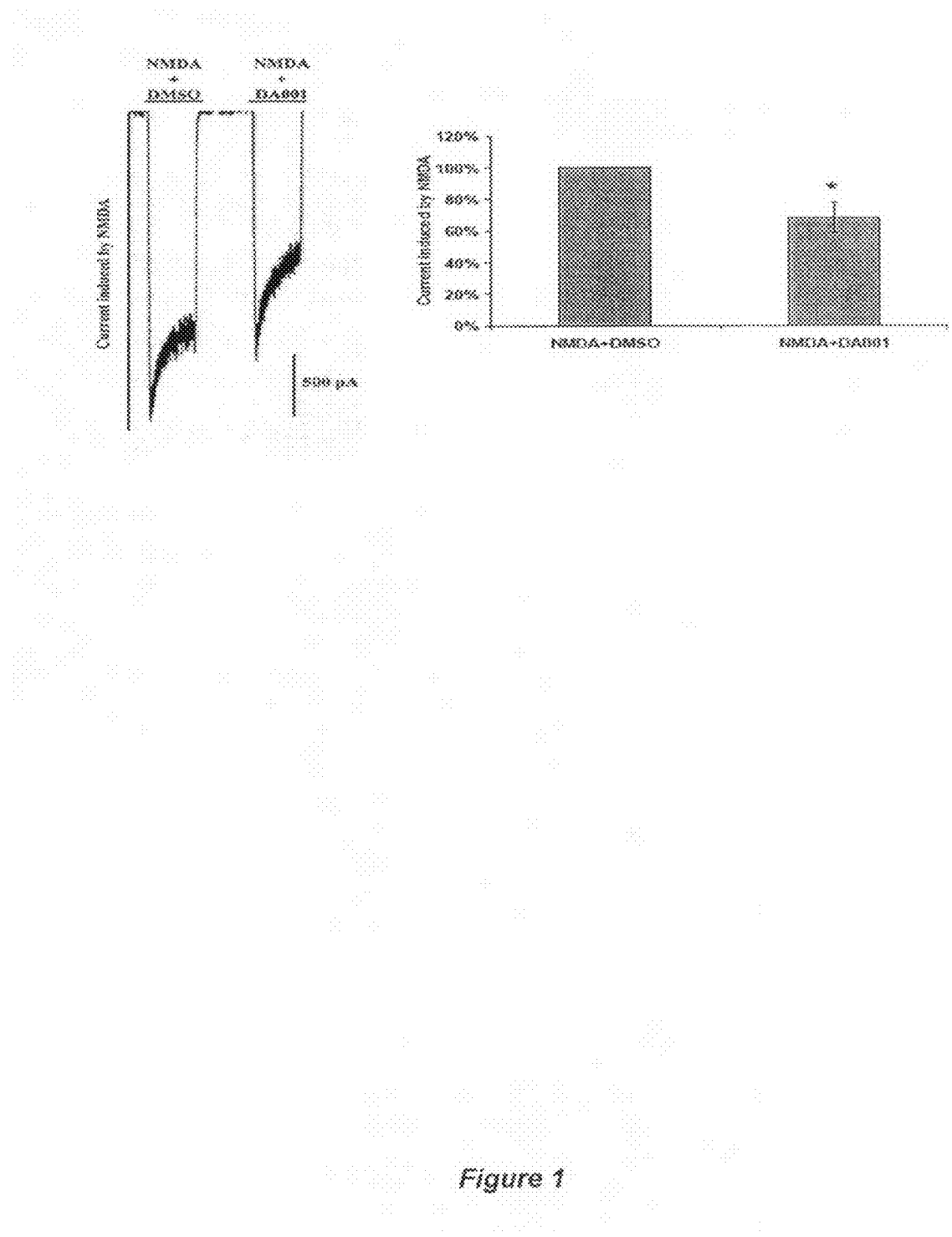
FIG. 1. DA001 decreases the NMDA induced current in hippocampal neurons. Hippocampal neurons from embryonic day 18 rats were isolated, trypsinized, plated onto 35-mm plates at a density of $3 \times 10^4$ cells/plate and cultured in Neurobasal medium (NB) supplemented with B27 nutrient. DIV 10-14 rat hippocampal neurons were treated with NMDA (50 μM) in the absence or presence of the compound DA001 (10 μg/ml). Data is presented as % of NMDA-induced current. DMSO is the solvent control.

The present invention is directed to therapeutically active compounds and pharmaceutical compositions as NMDA and MC receptor antagonists, methods of inhibiting over-activation of NMDA and MC receptors, methods of treating and/or preventing neurodegenerative diseases and neuropathological disorders, methods of providing neuroprotection under stress conditions, such as a stroke, and methods of enhancing the brain's cognitive functions in mammals and humans. For example, the present invention provides therapeutic agents and methods for prevention and/or treatment of acute and chronic disorders of CNS, ranging from neuropathological conditions, such as neuropathic pain, stroke, brain trauma, and epilepsy to neurodegenerative diseases such as amyotrophic lateral sclerosis, Alzheimer's disease, Parkinson's disease and Huntington's disease. Furthermore, the present invention provides neuronal protection against glutamate-induced neurodegeneration and toxicity, and enhances the brain's cognitive functions, such as learning and memory. For instance, compound 3-O-[α-L-rhamnopyranosyl-(1→2)-αL-arabinopyranosyl]-3,23-dihydroxy-20(29)-lupen-28-oic acid (DA001) and its derivatives are capable of protecting nerve cells and tissues subjected to glutamate-induced stress from damage by blocking the toxic effects of over-activated N-methyl-D-aspartate (NMDA) receptors.

Advantageously, the present invention provides NMDA and MC receptor antagonists. In particular, the present invention provides the NMDA and MC receptor antagonists that have unique functionality, for example, the compounds can (i) inhibit NMDA and MC receptor-mediated excitotoxicity; (ii) prevent and/or treat neurodegenerative diseases including amyotrophic lateral sclerosis, Alzheimer's disease, Parkinson's disease and Huntington's disease, and neuropathological conditions; (iii) improve learning and memory in mammals or humans by enhancing long-term potentiation; (iv) confer neuroprotection under oxidative stress and in stroke-like conditions; and (v) treat depression, anxiety, anorexia and cachexia induced by other chronic diseases. As such, the compounds are therapeutically potent over a range of disorders including dementia, neurodegeneration, brain trauma and stroke.

II. Definitions

Disease states that can be treated using the compounds of the invention to inhibit NMDA and/or MC receptor activity and protect against glutamate induced neurotoxicity include, but are not limited to, neurodegenerative disorders, head and brain trauma, genetic disorders, infectious disease, inflammatory disease, medication, drug and alcohol disorders, neuropathic pain, cancer, metabolic disorders, mental retardation, and learning and memory disorders, such as age related memory loss, Alzheimer's disease, mild cognitive impairment, amyotrophic lateral sclerosis, Huntington's chorea, amnesia, B1 deficiency, schizophrenia, depression and bipolar disorder, stroke, hydrocephalus, subarachnoid hemorrhage, vascular insufficiency, celebrovascular ischemia, brain tumor, epilepsy, Parkinson's disease, cerebral microangiopathy, pain medication, chemotherapy, oxygen deprivation, e.g, caused by a heart-lung machine, anesthesia, or near drowning, dementia (vascular, frontotemporal, Lewy-body, semantic, primary progressive aphasia, Pick's), progressive supranuclear palsy, corticobasal degeneration, Hashimoto encephalopathy, ADD, ADHD, dyslexia, Down syndrome, fragile X syndrome, Turner's syndrome, fetal alcohol syndrome, depression, anxiety, anorexia, cachexia, and cognitive deterioration such as in schizophrenia, cerebral palsy and autism, for example.

"Neuropathic" pain refers to pain resulting from injury to or chronic changes in peripheral and/or central sensory pathways, where the pain often occurs or persists without an obvious noxious input.

As used herein, "administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, pentyl, hexyl, iso-propyl, iso-butyl, sec-butyl, tert-butyl, etc.

As used herein, the term "alkenyl" refers to a straight or branched unsaturated alkyl group having one or more double bonds. Exemplary $C_{2-6}$alkenyl group include, but are not limited to, vinyl, 1-propenyl, 2-propenyl, 1-butenyl, 2-butenyl, 1-pentenyl, 2-pentenyl, 1-hexenyl, 2-hexenyl, 3-hexenyl, crotyl, 2-isopentenyl, 2-(butadienyl), 2,4-pentadienyl, 3-(1,4-pentadienyl), and the higher homologs and isomers.

As used herein, the term "cycloalkyl" refers to hydrocarbon rings having the indicated number of ring atoms (e.g., $C_{3-6}$cycloalkyl) and being fully saturated or having no more than one double bond between ring vertices. One or two C atoms may optionally be replaced by a carbonyl.

As used herein, the term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention.

As used herein, the term "aryl" refers to, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "composition" as used herein is intended to encompass a product comprising the specified ingredients in the specified amounts, as well as any product which results, directly or indirectly, from combination of the specified ingredients in the specified amounts.

As used herein, the term "epoxyalkyl" refers to an alkyl group defined hereinabove having an epoxide group. More particularly, C$_{2-6}$epoxyalkyl includes epoxyethyl, epoxypropyl, epoxybutyl, epoxypentyl, epoxyhexyl and the other isomeric forms thereof. For example, C$_{2-3}$epoxyalkyl includes epoxyethyl and epoxypropyl. As used herein, the term "epoxide" refers to chemical compounds or reagents comprising a bridging oxygen wherein the bridged atoms are also bonded to one another either directly for indirectly. Examples of epoxides include 1,2-epoxyethylene (oxirane), propylene oxide, and the like.

As used herein, the terms "halo" or "halogen," by themselves or as part of another substituent, mean, unless otherwise stated, a fluorine, chlorine, bromine, or iodine atom.

As used herein, the terms such as "haloalkyl," are meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, and the like.

As used herein, the term "hydrate" refers to a compound that is complexed to at least one water molecule. The compounds of the present invention can be complexed with from 1 to 10 water molecules.

As used herein, the term "inhibiting" refers to a compound that partially or fully prohibits or a method of partially or fully prohibiting a specific action or function.

As used herein, the term "monosaccharide" or "sugar" refers to a carbohydrate molecule that are straight-chain aldehydes or ketones, which may be combined in acetal or ketal forms. The remaining carbons of the molecule usually have hydrogen and multiple hydroxyl groups. The monosaccharide has an empirical formula of (CH$_2$O)$_n$, wherein n is 3-7, and preferably 4-7, even more preferably 5-7. In some embodiments, the term refers to "simple sugars" that consist of a single polyhydroxy aldehyde or ketone unit. Representative examples of monosaccharides include, but are not limited to, glucose, fructose, mannose, and galactose. Representative examples of disaccharides include, but are not limited to, lactose, maltose, and sucrose.

As used herein, the term "patient in need" refers to a patient suffering from the central nervous disorders including neurodegenerative diseases and neuropathological conditions. Non-limiting examples include amyotrophic lateral sclerosis, Parkinson's disease, Alzheimer's disease, Huntington's disease, neuropathic pain, stroke, brain trauma, epilepsy stroke, and dementia. Patients suffering from other conditions treatable with the NMDA antagonists are also treatable with the methods of the present invention. Patients treatable using the methods of the present invention are animals such as mammals, including, but not limited to, primates (e.g., humans), cows, sheep, goats, horses, dogs, cats, rabbits, rats, mice and the like. In certain embodiments, the patient is a human.

As used herein, the term "prodrug" refers to covalently bonded carriers which are capable of releasing the active agent of the methods of the present invention, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of the active agents of the present invention include active agents wherein a hydroxy, amidino, guanidino, amino, carboxylic or a similar group is modified.

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

As used herein, pharmaceutically acceptable salts of the basic compounds of the present invention are salts formed with acids, such as of mineral acids, organic carboxylic and organic sulfonic acids, e.g., hydrochloric acid, methanesulfonic acid, maleic acid, are also possible provided a basic group, such as pyridyl, constitutes part of the structure.

As used herein, "pharmaceutically acceptable" is meant the carrier, diluent or excipient must be compatible with the other ingredients of the formulation and not deleterious to the recipient thereof.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g, Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

III. Compounds

In one aspect, the present invention provides compounds of formula (I):

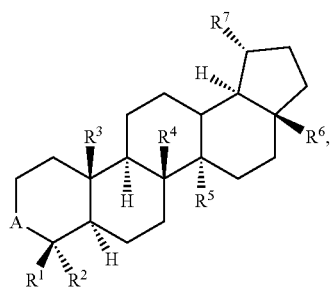

or a pharmaceutically acceptable salt, prodrug, hydrate, isomer thereof.

In formula I, $R^1$, $R^3$, $R^4$ and $R^5$ are each independently $C_{1-4}$alkyl. In one embodiment, $R^1$, $R^3$, $R^4$ and $R^5$ are each independently selected from the group consisting of methyl, ethyl, propyl, isopropyl, butyl, iso-butyl and s-butyl. In another embodiment, $R^1$, $R^3$, $R^4$ and $R^5$ are each independently methyl.

In formula I, $R^2$ is selected from the group consisting of $C_{1-6}$haloalkyl, $C_{3-6}$cycloalkyl, —$X^1$CN, —$X^1$NO$_2$, —$X^1$C(O)$R^a$, —$CR^b$=NOR$^c$, —$X^1$CO$_2R^c$, —$X^1$C(O)NR$^c R^d$, —$X^1$C(NR$^c R^d$)=NR$^c$, —$X^1$C(O)NR$^c$S(O)$R^d$, —$X^1$C(O)NR$^c$S(O)$R^d$, —$X^1$SR$^e$, —$X^1$NHR$^e$ and —$X^1$N(R$^e$)$_2$ and —$X^1R^e$, wherein each $X^1$ is independently a bond or $C_{1-4}$alkylene, wherein $R^e$ is $C_{1-6}$alkyl, $C_{1-6}$haloalkyl, arylC$_{0-6}$alkyl or $C_{3-6}$cycloalkyl substituted with from 1-3 members of $R^f$, and wherein $R^a$, $R^b$, $R^c$ and $R^d$ are each independently H, $C_{1-6}$alkyl or aryl-$C_{1-6}$alkyl; wherein the aliphatic portion of each $R^2$ substituent is optionally substituted with from 1-3 $R^f$, wherein $R^f$ is selected from the group consisting of halo, CN, NO$_2$, —OH, —$R^g$, —OR$^g$, —OC(O)NHR$^g$, —OC(O)N(R$^g$)$_2$, —OC(O)R$^g$, —OC(O)H, —NH$_2$, —NHR$^g$, —N(R$^g$)$_2$, —SH, —SR$^g$, —S(O)$_2R^g$, —SO$_2$NH$_2$, —SO$_2$NHR$^g$, —SO$_2$N(R$^g$)$_2$, —NHS(O)$_2R^g$, —NR$^g$S(O)$_2R^g$, —C(O)NH$_2$, —C(O)NHR$^g$, —C(O)N(R$^g$)$_2$, —C(O)H, —C(O)R$^g$, —NHC(O)R$^g$, —NR$^g$C(O)R$^g$, —NHC(O)NH$_2$, —NR$^g$C(O)NH$_2$, —NR$^g$C(O)NHR$^g$, —NHC(O)NHR$^g$, —NR$^g$C(O)N(R$^g$)$_2$, —NHC(O)N(R$^g$)$_2$, —COOH, —CO$_2R^g$, —NHCO$_2R^g$, —NR$^g$CO$_2R^g$ and —OSi(R$^g$)$_3$, wherein each R$^g$ is independently a $C_{1-6}$alkyl. R$^g$ can also be optionally substituted with an aryl. In certain instances, the aryl in R$^g$ can be further substituted with from 1-3 R$^f$. In one embodiment, $R^a$, $R^b$, $R^c$ and $R^d$ are each independently H, $C_{1-6}$alkyl or phenyl-$C_{1-6}$alkyl.

In one group of embodiments of compounds having formula I, $R^2$ is selected from the group consisting of —$X^1$C(O)R$^a$, —CR$^b$=NOR$^c$, —$X^1$NHR$^e$, —$X^1$N(R$^e$)$_2$ and —$X^1R^e$. In certain instances, $X^1$ is a bond. In certain other instances, $X^1$ is CH$_2$. In yet certain other instances, R$^e$ is $C_{1-6}$alkyl substituted with from 1-3 R$^f$. In some occasions, R$^e$ is —CH$_2$—R$^f$.

In another group of embodiments of compounds having formula I, $R^2$ is selected from the group consisting of —CH$_2$OH, —CH$_2$OAc, —CH$_2$OC$_{1-6}$alkyl, —CHO, —CH=NOR$^c$, —CH$_2$NHR$^e$, —CH$_2$OSi(R$^e$)$_3$ and —CH$_2$OSi(R$^f$)$_3$. In certain instances, $R^2$ is —CH$_2$OH, —CH$_2$OAc, —CH$_2$OC$_{1-6}$alkyl, —CHO, —CH$_2$OSiTBS, —CH=NOH, —CH$_2$NH—C$_{1-6}$alkyl-aryl and —CH=NOR$^g$. In certain other instances, $R^2$ is selected from the group consisting of —CH$_2$OH, —CH$_2$OAc, —CH$_2$OTBS, —CHO, —CH=NOH and —CH$_2$NHBn.

In formula I, the symbol A is selected from the group consisting of C=$Y^1$, C=NOR$^c$, C=NOC(O)R$^g$, C=NOCO$_2R^g$, C=NOC(O)NH$_2$, C=NOC(O)NHR$^g$ and C=NOC(O)N(R$^g$)$_2$ and —CR$^c R^h$, wherein $Y^1$ is =O or =S, and R$^h$ is selected from the group consisting of halo, CN, NO$_2$, —OH, —OR$^i$, —OC(O)NHR$^i$, —OC(O)N(R$^i$)$_2$, —OC(O)R$^i$, —OC(O)H, —NH$_2$, —NHR$^i$, —N(R$^i$)$_2$, —SH, —SR$^i$, —S(O)$_2R^i$, —SO$_2$NH$_2$, —SO$_2$NHR$^i$, —SO$_2$N(R$^i$)$_2$, —NHS(O)$_2R^i$, —NR$^i$S(O)$_2R^i$, —C(O)NH$_2$, —C(O)NHR$^i$, —C(O)N(R$^i$)$_2$, —C(O)H, —C(O)R$^i$, —NHC(O)R$^i$, —NR$^i$C(O)R$^i$, —NHC(O)NH$_2$, —NR$^i$C(O)NH$_2$, —NR$^i$C(O)NHR$^i$, —NHC(O)NHR$^i$, —NR$^i$C(O)N(R$^i$)$_2$, —NHC(O)N(R$^i$)$_2$, —COOH, —CO$_2R^i$, —NHCO$_2R^i$, —NR$^i$CO$_2R^i$, —OSi(R$^i$)$_3$, —O—(Z)$_{1-6}$, —S—(Z)$_{1-6}$, —NH(Z)$_{1-6}$ and —NR$^c$(Z)$_{1-6}$, wherein each R$^i$ is independently a $C_{1-6}$alkyl, $C_{1-6}$haloalkyl, $C_{3-6}$cycloalkyl, arylC$_{0-6}$alkyl or —(Z)$_{1-6}$, optionally substituted with from 1-3 R$^f$; —(Z)$_{1-6}$ is a sequence of 1-6 independently selected $C_{4-7}$monosaccharide residues linked together through ether bonds, optionally Z is substituted with from 1-3 $C_{1-6}$alkyl or R$^f$.

In one group of embodiments of compounds having formula I, A is CR$^c$—O(Z)$_{1-6}$. In one instance, Z is independently $C_{4-7}$monosaccharide. In another instance, Z is independently $C_{5-6}$monosacchardide residue. Exemplary $C_{4-7}$monosaccharides include, but are not limited to, erythrose, threose, arabinose, ribose, ribulose, xylose, xylulose, lyxose, allose, altrose, fructose, galactose, glucose, gulose, idose, mannose, sorbose, talose and tagatose, Sedoheptulose. Preferably, Z is a $C_{5-6}$monosaccharide residue selected from the group consisting of arabinose, ribose, ribulose, xylose, xylulose, lyxose, allose, altrose, fructose, galactose, glucose, gulose, idose, mannose, sorbose, talose, tagatose and each of which is optionally acetylated. In yet another instance, —(Z)$_2$ is selected from the group consisting of:

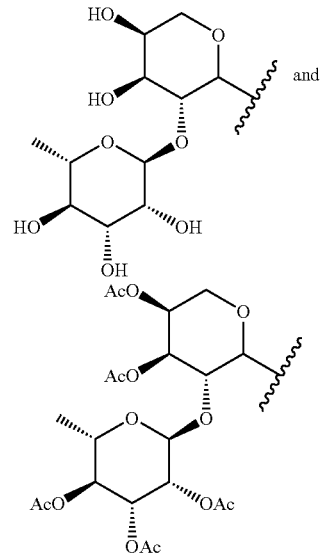

where the wavy line indicates the point of attachment to the rest of the molecule.

In another group of embodiments of compounds having formula I, A is selected from the group consisting of C=O, $CR^cR^h$, C=$NOR^c$, C=$NOC(O)R^g$, C=$NOCO_2R^g$, C=$NOC(O)NH_2$, C=$NOC(O)NHR^g$ and C=$NOC(O)N(R^g)_2$. In one instance, A is selected from the group consisting of C=O, $CR^c$—$OR^d$, $CR^c$—$OC(O)R^i$, C=$NOR^c$, C=$NOC(O)R^g$, C=$NOCO_2R^g$, C=$NOC(O)NH_2$, C=$NOC(O)NHR^g$, C=$NOC(O)N(R^g)_2$, $CR^c$—$NH_2$, $CR^c$—$NHR^i$, $CR^c$—$OSi(R^i)_3$ and $CR^c$—$N(R^i)_2$. In another instance, A is selected from the group consisting of C=O, $CR^c$-β-OH, $CR^c$—OBn, $CR^c$—OAc, C=NOH, $CR^c$—$NHR^c$ and $CR^c$—SiTBS. In one instance, $R_c$ is H. In certain other instances, A is selected from the group consisting of CH—OH, CHOAc, C=O, C=NOAc, CHO,

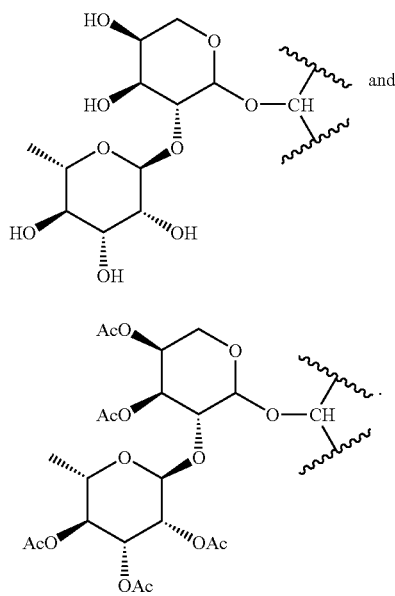

$R^6$ is selected from the group consisting of $C_{1-6}$haloalkyl, $C_{3-6}$cycloalkyl, —$X^2$CN, —$X^2NO_2$, —$X^2C(O)R^a$, —$CR^b$=$NOR^c$, —$X^2CO_2R^c$, —$X^2C(O)NR^cR^d$, —$X^2C(NR^cR^d)$=$NR^e$, —$X^2C(O)NR^cS(O)R^d$, —$X^2C(O)NR^cS(O)_2R^d$, —$X^2OR^a$, —$X^2SR^a$, —$X^2NHR^a$ and —$X^2N(R^a)_2$ and —$X^2R^e$, wherein each $X^2$ is independently a bond or $C_{1-4}$alkylene; wherein the aliphatic portion of each $R^6$ substituent is optionally substituted with from 1-3 $R^f$, wherein the two adjacent $R^f$ substituents together with the atoms to which they are attached optionally form a 5-membered heterocyclic ring having from 1-3 heteroatoms selected from N, O or S, wherein the heterocyclic ring is optionally substituted with from 1-3 $R^g$, and the aromatic ring of each $R^6$ is optionally substituted with from 1-5 $R^f$.

In one group of embodiments, $R^6$ is selected from the group consisting of —$X^2OC(O)R^a$, —$X^2CO_2R^c$, —$X^2C(O)NR^cR^d$, —$X^2R^e$, —$X^2C(O)R^a$ and —$CR^b$=$NOR^c$. In certain instances, $R^6$ is selected from the group consisting of —COOH, —$COOR^g$, —$CH_2OH$, —$CH_2OR^g$, —CHO, —$CH_2NHCH_2$Ph and —CH=$NOR^c$, —$CH_2OAc$, —$CH_2CH_2OH$, —$C_{1-6}$alkylene-OH, $CO_2$—$C_{1-6}$alkylene-OH, —$CH_2CH(OH)$—$CH_2OH$, $CO_2$—$CH_2CH(OH)$—$CH_2OH$, —$C_{1-6}$alkylene-$NH_2$, CONH—$C_{1-6}$alkylene-$NH_2$, —$C(O)NH_2$, —$C(O)NHR^c$ and

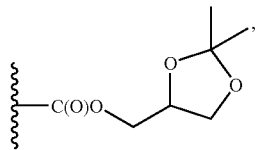

wherein $R^c$ is optionally substituted with —OH or $NH_2$. In certain other instances, $R^6$ is selected from the group consisting of —COOH, —$CH_2OH$ and —CH=$NOR^c$. In one occurrence, $R^c$ is —H. In another occurrence, $R^6$ is selected from the group consisting of —COOH, —COOMe, —COOEt, —$CH_2OH$, —CHO, —CH=NOH, —$CH_2OAc$, —$CH_2CH_2OH$, —$CO_2CH_2CH_2OH$, —$C_{1-6}$alkylene-OH, —$CO_2$—$C_{1-6}$alkylene-OH, —$CO_2CH_2CH_2OH$, —$CH_2CH(OH)$—$CH_2OH$, $CO_2$—$CH_2CH(OH)$—$CH_2OH$, —$C_{1-6}$alkylene-$NH_2$, —$C(O)NH_2$, —$C(O)NHCH_3$, —$C(O)NHCH_2$Ph, —$C(O)NH$—$C_{1-6}$alkylene-OH, —$CONHCH_2CH_2OH$, —$C(O)NH$—$C_{1-6}$alkylene-$NH_2$, —$CONHCH_2CH_2NH_2$ and

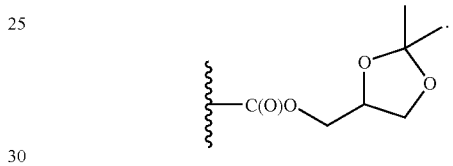

In yet another occurrence, $R^6$ is selected from the group consisting of —COOH, —COOMe, —COOEt, —$CH_2OH$, —CHO, —CH=NOH, —$CH_2OAc$, —$CO_2CH_2CH_2OH$, —$CH_2CH_2OH$, —$CO_2CH_2CH(OH)$—$CH_2OH$, —$C(O)NH_2$, —$C(O)NHCH_3$, —$C(O)NHCH_2$Ph, —$C(O)NH$—$CH_2CH_2$—$NH_2$ and

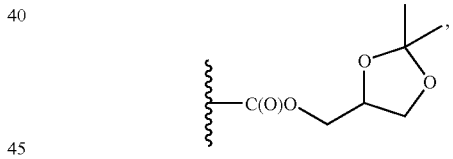

wherein the wavy line indicates the point of attachment to the rest of the molecule.

$R^7$ is selected from the group consisting of $C_{1-6}$alkyl, $C_{1-6}$haloalkyl, $C_{3-6}$cycloalkyl, $C_{2-6}$alkenyl, $C_{2-6}$haloalkenyl, $C_{5-6}$cycloalkenyl and $C_{2-6}$epoxyalkyl, optionally substituted with from 1-3 $R^f$. In certain instances, the aryl in $R^f$ can be further substituted with from 1-3 $R^f$ groups.

In one group of embodiments, $R^7$ is selected from the group consisting of $C_{1-6}$alkyl, $C_{2-6}$alkenyl and $C_{2-6}$epoxyalkyl, each of which is optionally substituted with 1-3 $R^f$. In certain instances, $R^7$ is $C_{1-6}$alkyl or $C_{2-6}$alkenyl. In certain other instances, $R^7$ is ethylene oxide radical, optionally substituted with 1-3 $R^f$. For example, $R^7$ is ethylene oxide substituted with from 1-3 $C_{1-6}$alkyl. Exemplary $R^7$ include epoxyethyl, epoxypropyl, epoxybutyl, epoxypentyl, epoxyhexyl and the other isomeric forms thereof, such as 1,2-epoxypropyl, 1,2-epoxy-2-propyl, 1,2-epoxy-3-propyl, 1,2-epoxybutyl, 1,2-epoxy-2-butyl, 1,2-epoxy-3-butyl, 2,3-epoxybutyl, and the like. In yet certain other instances, $R^7$ is selected from the group consisting of —CH=$CH_2$, —$C(CH_3)$=$CH_2$, —$C(CH_2OH)$=$CH_2$, —$CH_2CH_3$, —$CH_2CH_2CH_3$, —CH (CH₃)CH₃, epoxyethyl, epoxypropyl, epoxybutyl and 1,2-epoxy-2-propyl. In one occurrence, R⁷ is selected from the group consisting of —C(CH₃)=CH₂, —C(CH₂OH)=CH₂ and 1,2-epoxy-2-propyl.

In one embodiment, compounds of formula I have subformula Ia:

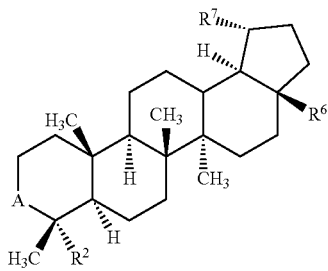

Ia where substituents R², R⁶, R⁷ and A are as defined above.

In a group of embodiments of compounds having formula Ia, A is CR$^c$—OH. In one instance, R⁶ is —COOH.

In a second group of embodiments of compounds having formula Ia, R² is C$_{1-6}$alkyl, haloalkyl or cycloalkyl substituted with 1-3 hydroxyl groups and A is other than CR$^c$—OC(O)C$_{1-6}$alkyl. In certain instances, R² is C$_{1-6}$alkyl substituted with a hydroxyl group. For example R² is —CH₂OH.

In one instance, compounds of subformula Ia have sub-subformula Ia-1:

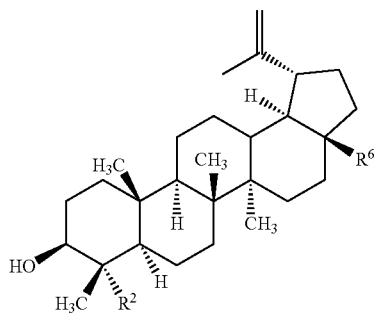

Ia-1 where substituents R² and R⁶ are as defined above.

In a second instance, compounds of subformula Ia have sub-subformula Ia-2:

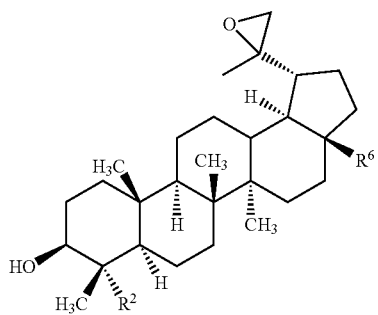

Ia-2 where substituents R² and R⁶ are as defined above.

In a third instance, compounds of subformula Ia have sub-subformula Ia-3:

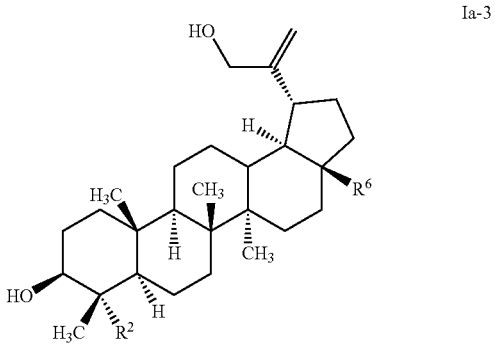

Ia-3 where substituents R² and R⁶ are as defined above.

In a fourth instance, compounds of subformula Ia have sub-subformula Ia-4:

Ia-4

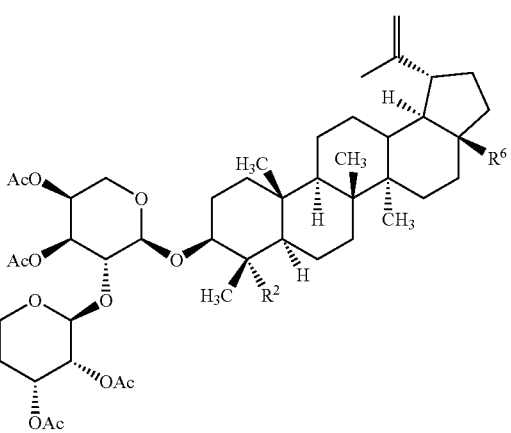

where substituents R² and R⁶ are as defined above.

In a fifth instance, compounds of subformula Ia have sub-subformula Ia-5:

Ia-5 where substituents R² and R⁶ are as defined above.

In one embodiment, the compounds have a formula selected from the group consisting of DA004, DA 007-9, DA012-14, DA016-17, DA019, DA021-029 and DA033-047 as set forth in Table 1.

Table 1 lists selected compounds according to some embodiments of the present invention. Exemplary compounds include selected 3-O-[α-L-rhamnopyranosyl-(1→2)-α-L-arabinopyranosyl]-3,23-dihydroxy-20(29)-lupen-28-oic acid derivatives.

TABLE 1

| Compound | A | $R^2$ | $R^6$ | $R^7$ |
|---|---|---|---|---|
| DA001 | (disaccharide structure shown) | —CH$_2$OH | —COOH | 2-propenyl |
| DA002 | CH—OH | —CH$_2$OH | —COOH | 2-propenyl |
| DA003 | CH—OH | —CH$_2$OH | —COOMe | 2-propenyl |
| DA004 | CH—OH | —CH$_2$OH | —COOEt | 2-propenyl |
| DA005 | CH—OH | —CH$_2$OH | —COOH | isopropyl |
| DA006 | CH—OAc | —CH$_2$OAc | —COOH | 2-propenyl |
| DA007 | CH—OAc | —CH$_2$OH | —COOH | 2-propenyl |
| DA008 | CH—OH | —CH$_2$OAc | —COOH | 2-propenyl |
| DA009 | CH—OH | —CH$_2$OH | —COOH | (epoxide group) |
| DA010 | CH—OH | —CH$_2$OH | —CH$_2$OH | 2-propenyl |
| DA011 | CH—OAc | —CH$_2$OAc | —COOMe | 2-propenyl |
| DA012 | CH—OH | —CH$_2$OAc | —COOMe | 2-propenyl |
| DA013 | C=O | —CH$_2$OAc | —COOMe | 2-propenyl |
| DA014 | C=O | —CH$_2$OH | —COOMe | 2-propenyl |
| DA015 | C=N—OH | —CH$_2$OH | —COOMe | 2-propenyl |
| DA016 | C=O | —CH$_2$OAc | —COOH | 2-propenyl |
| DA017 | CH—OH | —CH$_2$OTBS | —COOH | 2-propenyl |
| DA018 | C=O | —CH$_2$OH | —COOH | 2-propenyl |
| DA019 | CH=N—OH | —CH$_2$OH | —COOH | 2-propenyl |
| DA020 | CH—OH | —CH$_2$OH | —CHO | 2-propenyl |
| DA021 | C=O | —CH$_2$OH | —CHNOH | 2-propenyl |
| DA022 | CH—OAc | —CH$_2$OAc | CHO | 2-propenyl |
| DA023 | CH—OAc | —CH$_2$OAc | —CH$_2$NHCH$_2$Ph | 2-propenyl |
| DA024 | CH—OH | —CH$_2$OH | —CH$_2$NHCH$_2$Ph | 2-propenyl |
| DA025 | C=N—OAc | —CH$_2$OAc | —COOMe | 2-propenyl |
| DA026 | CH—OH | —CHO | —COOMe | 2-propenyl |
| DA027 | CH—OH | —CH=NOH | —COOMe | 2-propenyl |
| DA028 | CH—OH | —CH$_2$NHBn | —COOMe | 2-propenyl |
| DA029 | CH—OH | —CH$_2$NHBn | —COOH | 2-propenyl |
| DA033 | CH—OH | —CH$_2$OH | —CH$_2$OAc | 2-propenyl |

TABLE 1-continued

| Compound | A | $R^2$ | $R^6$ | $R^7$ |
|---|---|---|---|---|
| DA034 | CH—OH | —CH$_2$OH | —CH$_2$OAc | 2-methyloxiranyl |
| DA035 | CH—OH | —CH$_2$OH | —CH$_2$OAc | 2-methyloxiranyl |
| DA036 | C=O | —CHO | —CH$_2$OAc | 2-methyloxiranyl |
| DA037 | CH—OH | —CH$_2$OH | —C(O)OMe | 3-hydroxy-2-propenyl |
| DA038 | CH—OH | —CH$_2$OH | —C(O)OCH$_2$-(2,2-dimethyl-1,3-dioxolan-4-yl) | 2-propenyl |
| DA039 | CH—OH | —CH$_2$OH | —C(O)OCH$_2$CH(OH)CH$_2$OH | 2-propenyl |
| DA040 | CH—OH | —CH$_2$OH | —C(O)O(CH$_2$)$_2$OH | 2-propenyl |
| DA041 | CH—OAc | —CH$_2$OAc | —C(O)NHCH$_2$Ph | 2-propenyl |
| DA042 | CH—OH | —CH$_2$OH | —C(O)NHCH$_2$Ph | 2-propenyl |
| DA043 | (triacetyl disaccharide-O—) | —CH$_2$OAc | —C(O)OAc | 2-propenyl |

TABLE 1-continued

[Structure: pentacyclic triterpene core with ring A bearing H₃C and R² substituents, CH₃ groups, R⁶ at C-17 position, and R⁷ substituent]

| Compound | A | R² | R⁶ | R⁷ |
|---|---|---|---|---|
| DA044 | [trisaccharide: AcO-substituted arabinopyranosyl-(1→2)-rhamnopyranosyl with AcO, AcO, OAc, OAc, OAc] | —CH₂OAc | —C(O)OH | 2-propenyl |
| DA045 | [trisaccharide: HO-substituted arabinopyranosyl-(1→2)-rhamnopyranosyl with HO, HO, OH, OH, OH] | —CH₂OH | —C(O)NHCH₂Ph | 2-propenyl |
| DA046 | [trisaccharide: AcO-substituted arabinopyranosyl-(1→2)-rhamnopyranosyl with AcO, AcO, OAc, OAc, OAc] | —CH₂OAc | —C(O)NH(CH₂)₂NH₂ | 2-propenyl |
| DA047 | [trisaccharide: HO-substituted arabinopyranosyl-(1→2)-rhamnopyranosyl with HO, HO, OH, OH, OH] | —CH₂OH | —C(O)NH(CH₂)₂NH₂ | 2-propenyl |

Preparation of Compounds

As shown in the examples below, there are a variety of synthetic routes by which a skilled artisan can prepare compounds and intermediates of the present invention. Schemes 1-4 illustrate several methods for the preparation of certain 3-O-[α-L-rhamnopyranosyl-(1→2)-α-L-arabinopyranosyl]-3,23-dihydroxy-20(29)-lupen-28-oic acid (Pulchinenoside) derivatives. In each of these schemes R, R', R" and R'" are non-interfering substituents.

The schemes below provide certain synthetic routes that can be followed to access certain Pulchinenoside derivatives of the present invention. Other routes or modification of the routes presented below would be readily apparent to a skilled artisan and within the scope of the present invention.

Scheme 1 shows the synthesis of certain compounds of the present invention by modification of C20-C29 double bond.
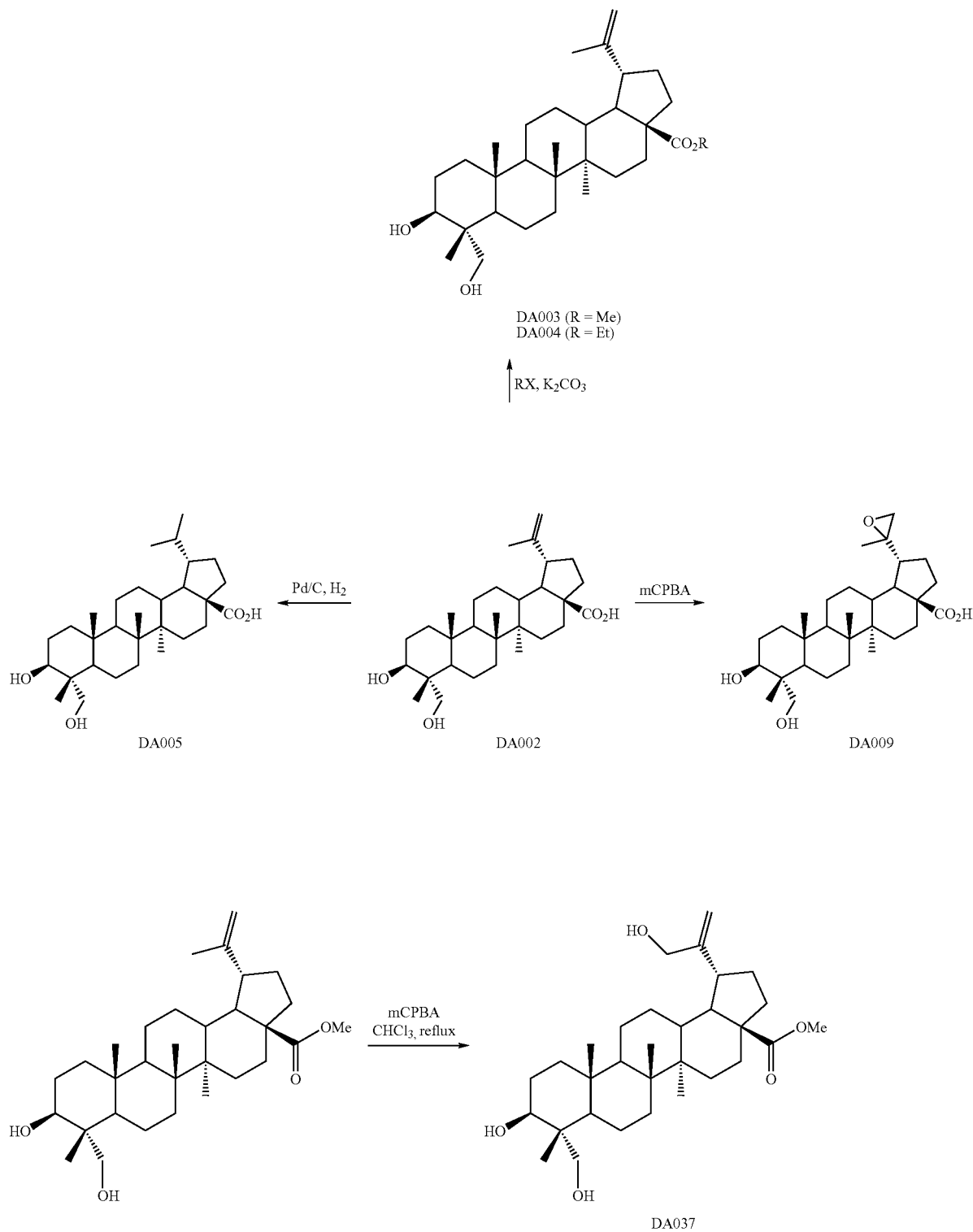

Scheme 2 shows the synthesis of certain compounds of the present invention by modifications at C3 position.
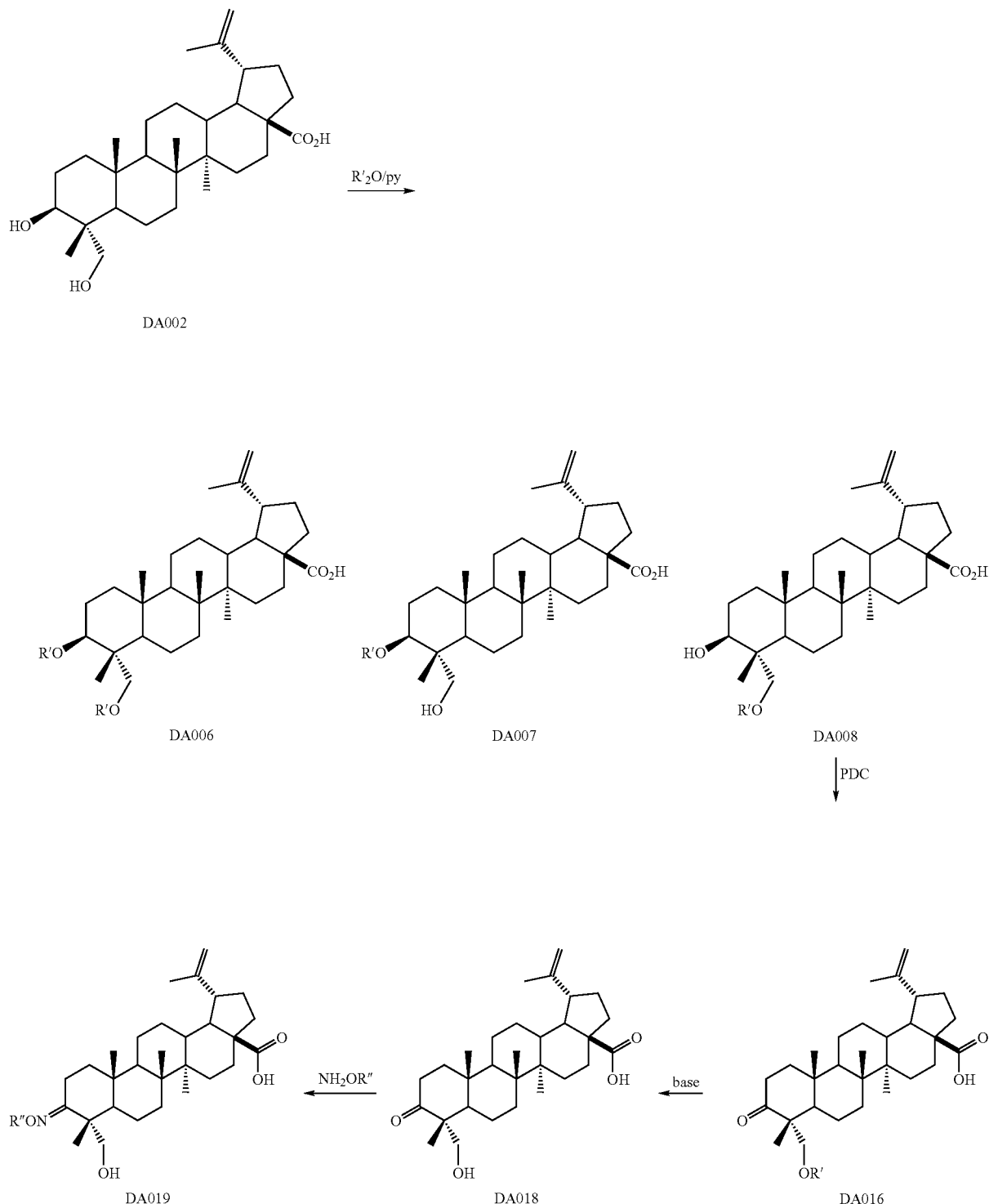
Scheme 3 shows the synthesis of certain compounds of the present invention by modifications at C28 position.

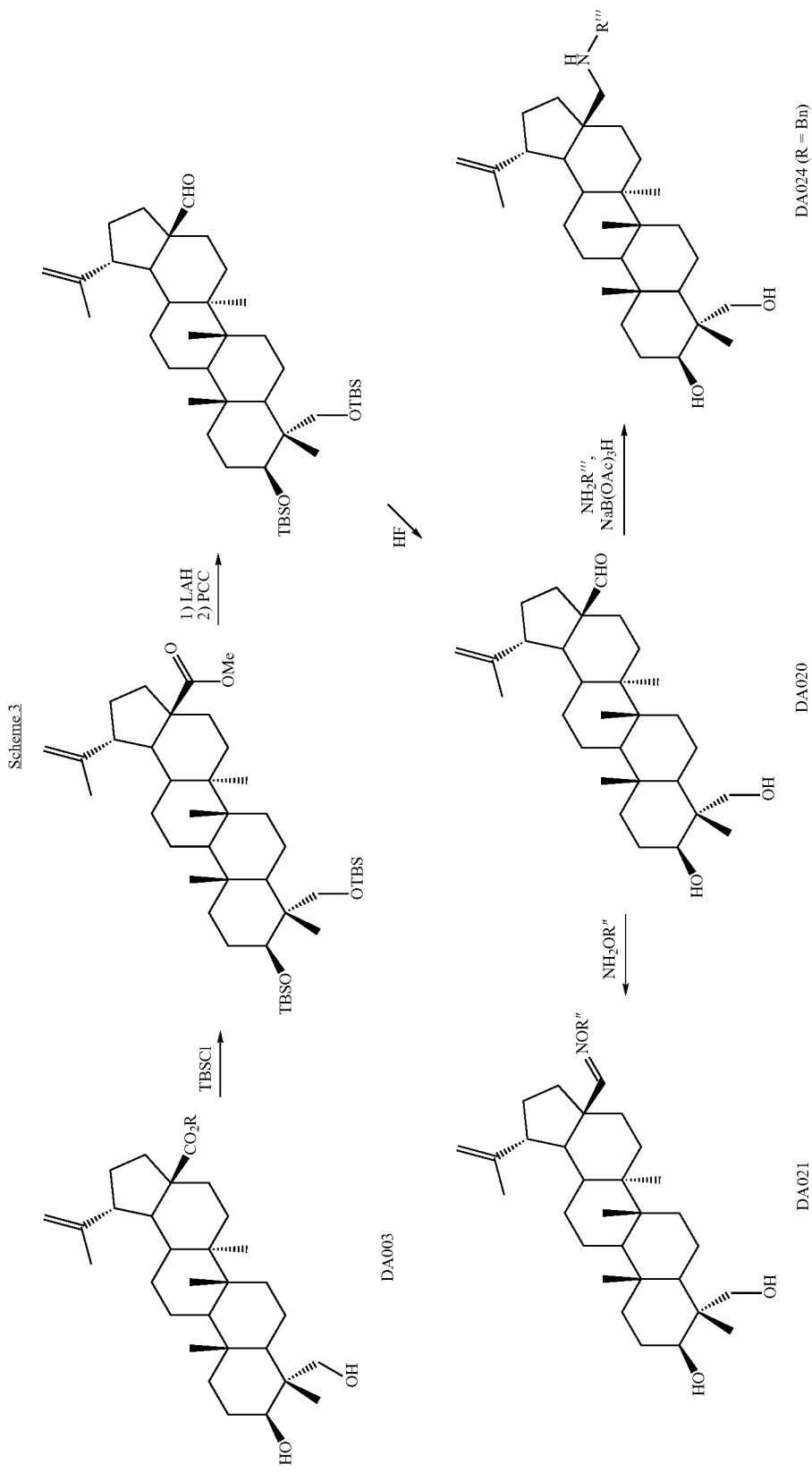

Scheme 4 shows the synthesis of certain compounds of the present invention by modifications at C23 position.
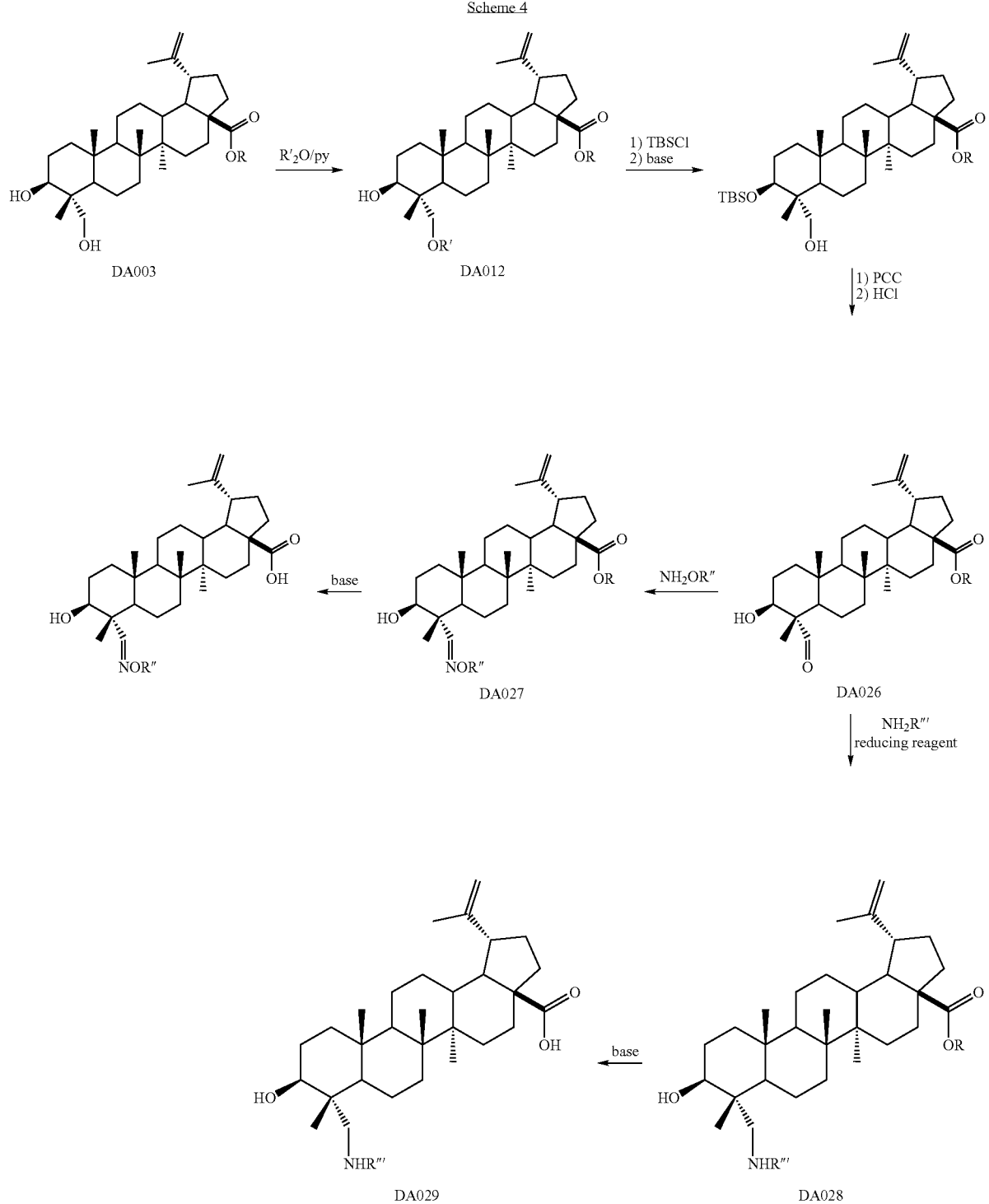
Scheme 5 shows a synthetic approach for the preparation of compounds D033-036 according to an embodiment of the invention.

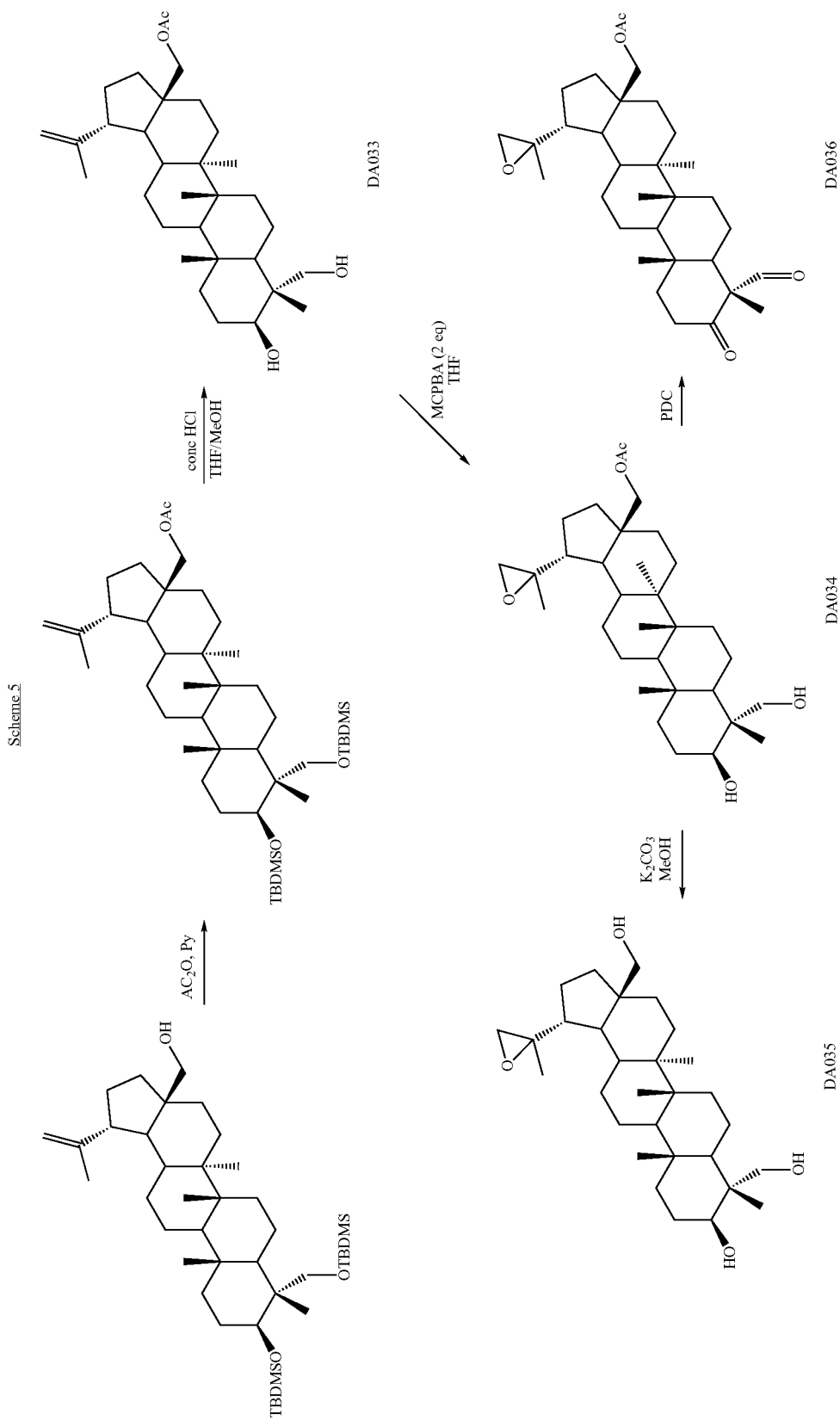

Scheme 6 shows the synthesis of compounds DA038-DA040 according to an embodiment of the invention.
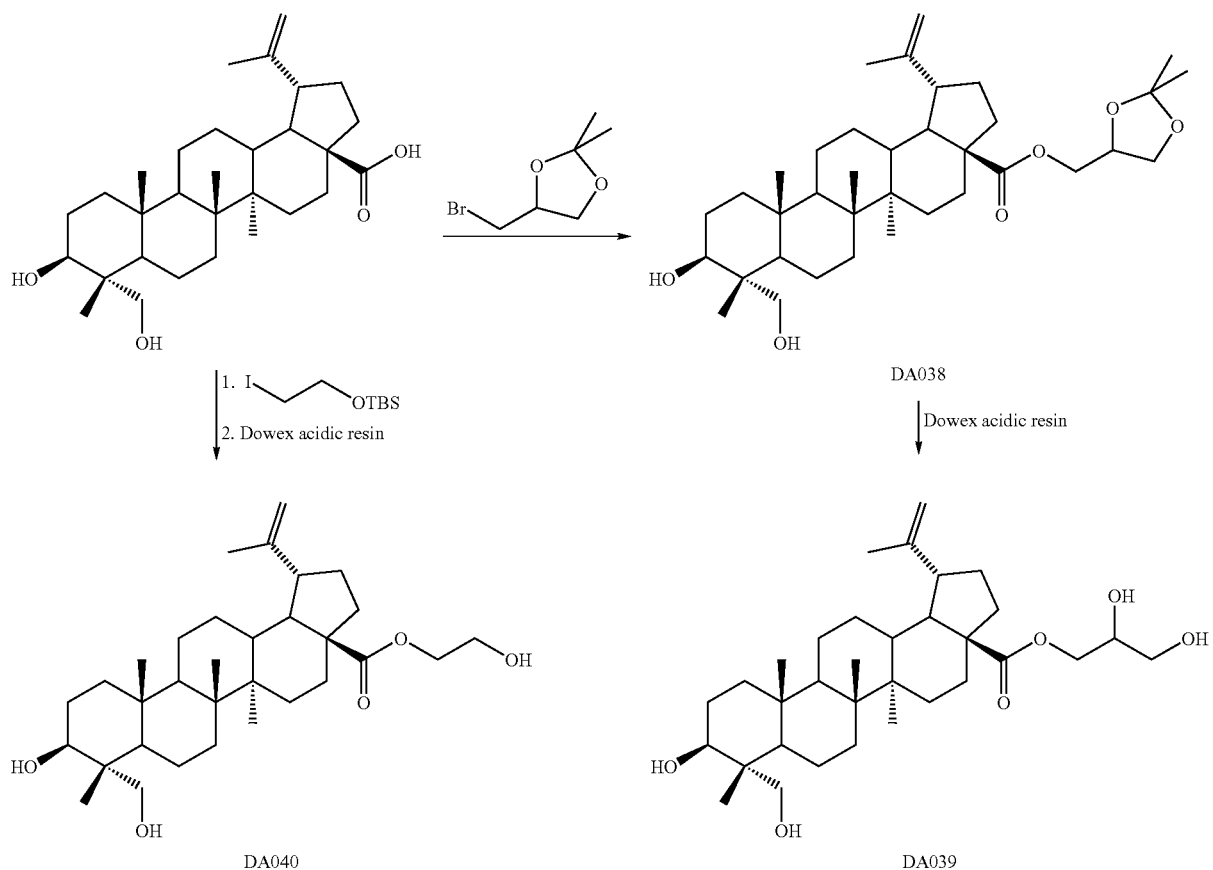
Scheme 7 describes the synthesis of compounds DA041-DA047 in accordance with an embodiment of the invention.
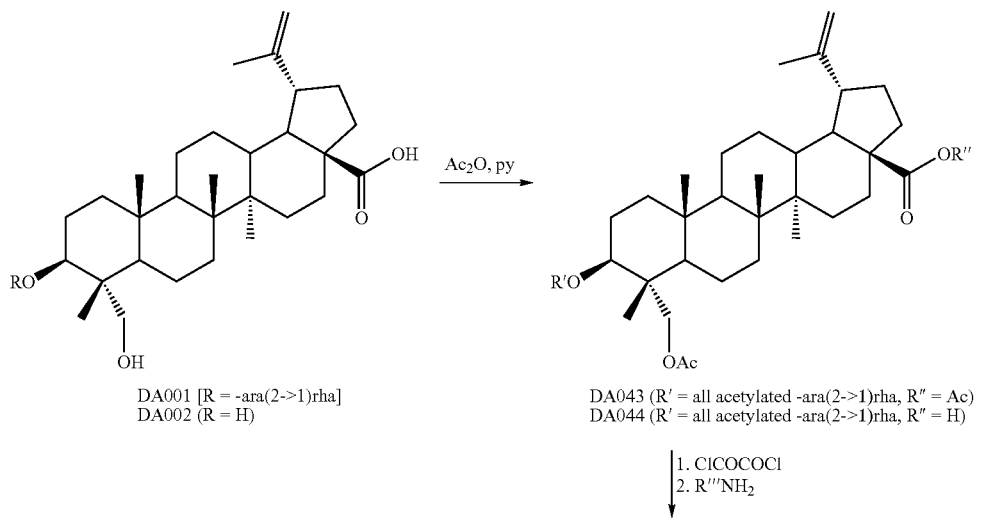

-continued

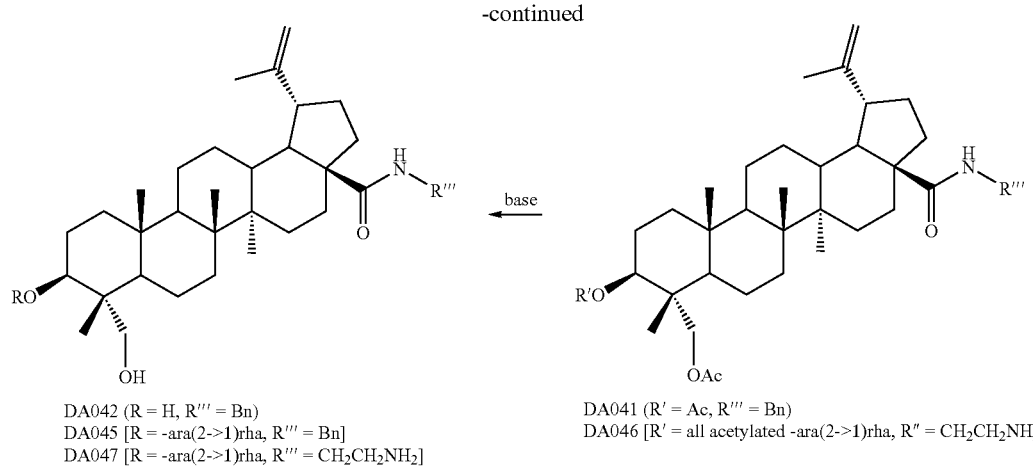

DA042 (R = H, R''' = Bn)
DA045 [R = -ara(2->1)rha, R''' = Bn]
DA047 [R = -ara(2->1)rha, R''' = CH$_2$CH$_2$NH$_2$]

DA041 (R' = Ac, R''' = Bn)
DA046 [R' = all acetylated -ara(2->1)rha, R'' = CH$_2$CH$_2$NH$_2$]

IV. Pharmaceutical Compositions

In addition to the compounds provided above, compositions for modulating NMDA and/or MC receptor activity in humans and animals will typically contain a compound of formula I or any of compounds DA001-047 and pharmaceutical carrier, excipient or diluent.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier, which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia; and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled with a carrier that is a suitable polymer as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

V. Methods of Treating Diseases and Disorders Modulated by NMDA and MC Receptors In another aspect, the present invention provides a method of inhibiting the activities of an NMDA receptor and/or an MC receptor, e.g. MC1 or MC4 receptor for treating and/or preventing CNS disorders. The method includes contacting a compound of formula I or any of compounds DA001-047, or a pharmaceutical composition thereof with the NMDA receptor. Preferably, the NMDA receptor is an activated NMDA receptor. In one embodiment, the method includes contacting a triterpene compound 3-O-[α-L-rhamnopyranosyl-(1→2)-α-L-arabinopyranosyl]-3,23-dihydroxy-20(29)-lupen-28-oic acid (DA001) or a pharmaceutical composition of compound DA001 with the NMDA receptor or the MC1 or MC4 receptor. The compound DA001 was isolated from the herb *Pulsatilla Chinensis* (see, Chen et al. "Saponins from *Pulsatilla Chinensis*" *Acta Chimica Sinica* 1990, 48, 501).

In one embodiment, the compounds of the present invention are NMDA and/or MC antagonists that can be used to inhibit the binding of NMDA and/or MC receptor ligand (e.g., glutamate) to NMDA receptor in vitro or in vivo. In general, such methods comprise the step of contacting an NMDA receptor or an MC with a sufficient amount of one or more NMDA or MC receptor antagonist as provided herein, in the presence of NMDA or MC receptor ligand in aqueous solution and under conditions otherwise suitable for binding of the ligand to NMDA or MC receptor. The NMDA or MC receptor may be present in suspension (e.g., in an isolated membrane or cell preparation), or in a cultured or isolated neuron cell.

Preferably, the amount of NMDA or MC receptor modulator contacted with the receptor should be sufficient to inhibit NMDA or MC binding to NMDA or MC receptor in vitro as measured, for example, using whole-cell patch clamp studies, calcium mobilization assay, fluorometric imaging plate reader (FLIPR) assay, or neuronal survival assay as described herein.

In one embodiment of the invention, the NMDA or MC receptor antagonists of the invention are used to modulate, preferably inhibit, the activity of an NMDA or MC receptor, for example, by contacting one or more compound(s) of the invention with an NMDA or MC receptor (either in vitro or in vivo) under conditions suitable for binding of the modulator(s) to the receptor. The receptor may be present in solution or suspension, in a cultured or isolated cell preparation or within a patient. Any modulation of the activity may be assessed using patch clamp, FLIPR, or calcium assay techniques by detecting the ion current across the surface of neurons, or by survival assay, or immunocytochemical analysis. In general, an effective amount of NMDA or MC antagonist(s) in an amount sufficient to modulate NMDA or MC receptor activity in vitro within patch clamp studies and calcium mobilization assays, followed by neuronal survival assays.

In another embodiment, comparative studies are conducted to determine its efficacy in comparison to the known antagonist memantine. The effect of the compound on cognitive functions, such as in treating dementia, improving memory in test subjects is evaluated in animal models using Morris Water Maze task.

In yet another aspect, the present invention provides methods and use of the compounds of formula I and any of compounds DA001-047 for the preventing and/or treating a neurodegenerative diseases or neuropathological conditions in a mammal or human. The methods include administering to the mammal or human a therapeutically effective amount of the compounds of the present invention.

In a further aspect, the present invention provides methods and uses of compounds of formula I or any of compounds DA001-047 for enhancing the brain's cognitive function in a mammal or human. The methods include administering to the subject a therapeutically effective amount of the compounds of the present invention.

In still another aspect, the present invention provides methods and use of compounds of formula I or any of compounds DA001-DA047 for inhibiting the activities of an MC receptor. The method includes contacting the compound with the MC receptor. In one embodiment, the MC receptor is MC1 or MC4 receptor. In another embodiment, the MC receptor is an MC4 receptor.

In another aspect, the present invention provides methods of treating depression, anxiety and cachexia induced by a chronic disease in a mammal. The method includes administering to the mammal a therapeutically effective amount of a compound of formula I or any compound of DA001-DA047. Non-limitaing chronic diseases that can induce cachexia include cancer, AIDS, renal failure, liver failure, congestive heart failure and lung disease.

Conditions that can be Treated by NMDA and MC Receptor Antagonists:

The present invention provides neuroprotection as well as improves cognitive deficits. As NMDA receptor antagonists, the compounds of the present invention are useful in the treatment of acute and chronic disorders of CNS, ranging from neuropathological conditions to neurodegenerative diseases and conditions related to excitotoxicity. Disease states that can be treated using the compounds of the present invention include, but are not limited to, neurodegenerative disorders, head and brain trauma, genetic disorders, infectious disease, inflammatory disease, medication, drug and alcohol disorders, neuropathic pain, cancer, metabolic disorders, mental retardation, and learning and memory disorders, such as age related memory loss, Alzheimer's disease, mild cognitive impairment, amyotrophic lateral sclerosis, Huntington's chorea, amnesia, B1 deficiency, schizophrenia, depression and bipolar disorder, celebrovascular, stroke, hydrocephalus, subarachnoid hemorrhage, vascular insufficiency, brain tumor, epilepsy, Parkinson's disease, cerebral microangiopathy, pain medication, chemotherapy, oxygen deprivation, e.g, caused by a heart-lung machine, anesthesia, or near drowning, dementia (vascular, frontotemporal, Lewy-body, semantic, primary progressive aphasia, Pick's), progressive supranuclear palsy, corticobasal degeneration, Hashimoto encephalopathy, ADD, ADHD, dyslexia, Down syndrome, fragile X syndrome, Turner's syndrome, fetal alcohol syndrome, depression, anxiety, anorexia and cachexia, for example.

The present invention also represents a new paradigm for ischemic stroke treatment. Current treatments are severely limited. Traditionally, acute ischemic stroke is treated using a tissue plasminogen activator (tPA). This drug can prevent some of the adverse impacts associated with stroke but only if it is administered intravenously within the first three hours of the event and only if there is no bleeding in the brain. With such a small therapeutic window, only a small percentage of stroke patients (~3%) receive effective treatment. In recent years, stroke research has focused on developing neuroprotective agents, compounds that may make the brain more resistant to damage from stroke. The compounds of the present invention have the ability to halt the ischemic cascade.

The compounds of the present invention exhibit neuroprotective properties. Moreover, they have demonstrated the abilities to prevent neuronal damage under conditions of stress. They confer protection to neuronal tissue when exposed to stroke-related conditions, and have immense potential as therapeutic drugs in the prevention and management of ischemic stroke.

In one embodiment of the invention, the compounds of the invention can be used for the treatment of diseases selected from the group consisting of amyotrophic lateral sclerosis, Alzheimer's disease, Parkinson's disease and Huntington's disease, acute or chronic neuropathic pain, stroke, brain trauma, epilepsy stroke and dementia.

Treatment methods provided herein include, in general, administration to a patient an effective amount of one or more compounds provided herein, e.g., orally, nasally or parenterally. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein, for example, compounds of formula I. In a preferred embodiment, the compound(s) of the invention are preferably administered to a patient (e.g., a human) orally. The effective amount may be an amount sufficient to modulate the NMDA and/or MC receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit the NMDA and/or MC receptor in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

The compounds of the present invention can be administered as frequently as necessary, including hourly, daily, weekly or monthly. Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch.

The pharmaceutical compositions can be administered to the patient in a variety of ways, including topically, parenterally, intravenously, intradermally, intramuscularly, colonically, rectally or intraperitoneally. Preferably, the pharmaceutical compositions are administered parenterally, topically, intravenously, intramuscularly or orally.

The compounds of formula I or formulae DA001-047 can also be administered in combination with additional therapeutic agents or diagnostic agents can be administered in combination with the compounds of formulas I or formulae DA001-047.

VI. Examples

The following abbreviations are used in the Examples and throughout the description of the invention:
TBSCl/TBDMSCl: tert-butyldimethylsilyl chloride
NMDA: N-methyl-D-aspartic acid
LAH: lithium aluminum hydride
PCC: pyridinum chloro chromate
PDC: pyridinum dichloro chromate
DMAP: 4-dimethylaminopyridine
Ac: acetyl
DMSO: dimethylsulfoxide
Bn: benzyl
MC: Melanocortins Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

Synthesis of 3,23-Dihydroxy-20(29)-lupen-28-oic acid (DA002)

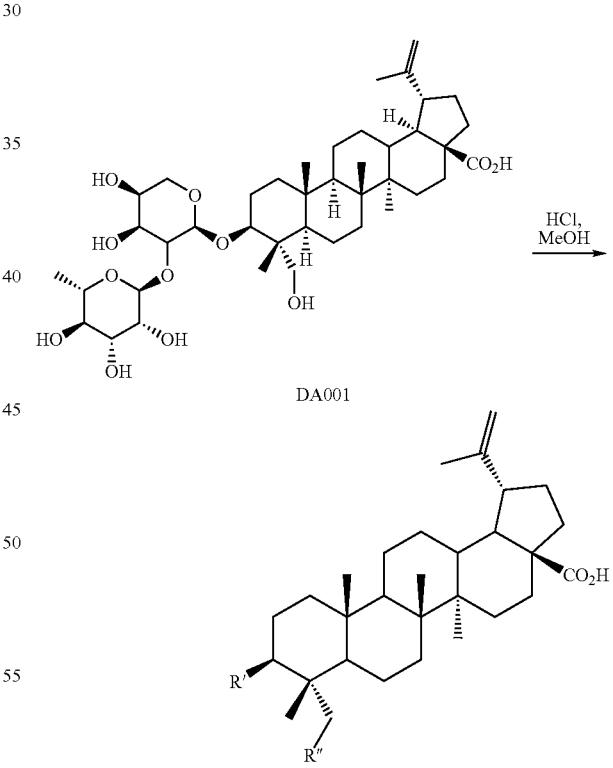

To a solution of HCl methanol reagent 10 (10 mL) was added Pulchinenoside A (DA001, 100 mg) and the resulting mixture was stirred at 35° C. for 4 days. After pouring into water (10 ml), the mixture was extracted with chloroform (3×50 ml). The combined organic layer was washed with $H_2O$ (1×10 ml), brine (1×10 ml), dried over sodium sulfate and concentrated under vacuum. The resulting residue was purified by column chromatography on silica gel using $CH_2Cl_2$-MeOH (v/v, 30:1) to yield the desired product as a white solid with 85% yield.

Example 2

Synthesis 3,23-Dihydroxy-20(29)-lupen-28-oic acid, methyl ester (DA003)

To a solution of 3,23-dihydroxy-20(29)-lupen-28-oic acid (10 mg, 0.021 mmol) in THF (2 mL) was added $K_2CO_3$ (4.4 mg, 0.032 mmol) and MeI (1.7 μL, 0.032 mmol). After stirring at room temperature for 12 h, the reaction was quenched by adding 20% $Na_2S_2O_3$ (0.5 ml) and saturated $NaHCO_3$ (0.5 ml). The mixture was extracted with ethyl acetate (3×10 ml). The combined organic layer was washed with $H_2O$ (1×2 ml), brine (1×2 ml), dried over sodium sulfate and concentrated under vacuum. The resulting residue was purified by column chromatography on silica gel using $CH_2Cl_2$-MeOH (v/v, 30:1) to yield the desired product as a white solid with 95% yield. $^1$H NMR (300 MHz, $CDCl_3$, δ ppm): 4.73 (s, 1H), 4.59 (s, 1H), 3.71 (d, J=10.5 Hz, 1H), 3.66 (s, 3H, $OCH_3$), 5.59-3.64 (m, 1H), 3.41 (d, J=10.5 Hz, 1H), 2.98-3.00 (m, 1H), 2.19-2.24 (m, 2H), 1.79-1.90 (m, 2H), 1.70 (s, 3H, $CH_3$), 1.00-1.68 (m, 22H), 0.89-0.99 (m, 12H, 4×$CH_3$).

Example 3

Synthesis of 3,23-Dihydroxy-20(29)-lupen-28-oic acid, ethyl ester (DA004)

To a solution of 3,23-dihydroxy-20(29)-lupen-28-oic acid (20 mg, 0.043 mmol) in DMF (2 ml) was added $K_2CO_3$ (9 mg), and EtI (5.2 μl) at r.t., and the resulting mixture was stirred at 40° C. overnight. After the reaction was quenched with 20% $Na_2S_2O_3$ (0.5 ml) and saturated $NaHCO_3$ (0.5 ml), the mixture was extracted with ethyl acetate (3×15 ml). The combined organic layer was washed with $H_2O$ (6×2 ml), brine (1×2 ml), dried over sodium sulfate and concentrated under vacuum. The resulting residue was purified by column chromatography on silica gel using $CH_2Cl_2$-MeOH (v/v, 30:1) to yield compound DA004 as a white solid with 90% yield. $^1$H NMR (300 MHz, $CDCl_3$, δ ppm): 4.72 (s, 1H), 4.59 (s, 1H), 4.13 (q, J=6.3 Hz, 2H), 3.70 (d, J=10.5 Hz, 1H), 3.60 (t, J=7.5 Hz, 1H), 3.40 (d, J=10.5 Hz, 1H), 2.95-3.00 (m, 1H), 2.20-2.24 (m, 2H), 1.70-1.90 (m, 2H), 0.99-1.67 (m, 28H), 0.85-0.95 (m, 12H, 4×$CH_3$).

Example 4

Synthesis of 3,23-Dihydroxy-lupan-28-oic acid (DA005)

To a solution of 3,23-dihydroxy-20(29)-lupan-28-oic acid (20 mg, 0.043 mmol) in MeOH (5 ml) was added a catalytic amount of 10% Pd/C. The mixture was stirred for 3 days under $H_2$ atmosphere (balloon pressure). After removing the catalyst by filtration, the filtrate was concentrated under reduced pressure to yield the desired product as a white solid with 95% yield.

Example 5

Synthesis of 3,23-Diacetoxy-20(29)-lupen-28-oic acid (DA006); 3-Acetoxy-23-hydroxy-20(29)-lupen-28-oic acid (DA007); and 23-Acetoxy-3-hydroxy-20(29)-lupen-28-oic acid (DA008)

To a solution of 3,23-dihydroxy-20(29)-lupen-28-oic acid (40 mg, 0.085 mmol) in pyridine (2.0 ml) was added DMAP (cat) and $Ac_2O$ (16.5 μL, 0.174 mmol). After stirring at room temperature for 1 h, the reaction was diluted with water. The mixture was extracted with ethyl acetate (3×20 ml), and then the combined organic layer was washed with 5% HCl (1×3 ml), saturated $NaHCO_3$ (1×3 ml), $H_2O$ (1×2 ml), brine (1×2 ml), dried over sodium sulfate and concentrated under reduced pressure. The resulting residue was purified by column chromatography on silica gel using $CH_2Cl_2$-MeOH to yield three desired products.

3,23-Diacetoxy-20(29)-lupen-28-oic acid (DA006)

$^1$H NMR (400 MHz, $CDCl_3$, δ ppm): 4.75-4.79 (m, 2H), 4.62 (s, 1H), 3.84 (d, J=11.6 Hz, 1H), 3.69 (d, J=11.6 Hz, 1H), 2.95-3.06 (m, 1H), 2.18-2.29 (m, 2H), 2.07 (s, 3H, $CH_3$), 2.02 (s, 3H, $CH_3$), 1.70 (s, 3H, $CH_3$), 1.02-1.68 (m, 23H) 0.98 (s, 3H, $CH_3$), 0.94 (s, 3H, $CH_3$), 0.88 (s, 3H, $CH_3$), 0.81 (s, 3H, $CH_3$).

3-Acetoxy-23-hydroxy-20(29)-lupen-28-oic acid (DA007)

$^1$H NMR (400 MHz, $CDCl_3$, δ ppm): 4.87 (dd, J=12.4, 4.4 Hz, 1H), 4.74 (s, 1H), 4.61 (s, 1H), 3.37 (d, J=12.8 Hz, 1H), 2.95-3.02 (m, 1H), 2.89 (d, J=12.8 Hz, 1H), 2.10-2.28 (m, 2H), 2.08 (s, 3H, $CH_3$), 1.73-2.05 (m, 2H), 1.69 (s, 3H, $CH_3$), 1.07-1.64 (m, 22H), 0.98 (s, 3H, $CH_3$), 0.93 (s, 3H, $CH_3$), 0.83 (s, 3H, $CH_3$), 0.65 (s, 3H, $CH_3$).

23-Acetoxy-3-hydroxy-20(29)-lupen-28-oic acid (DA008)

$^1$H NMR (400 MHz, $CDCl_3$, δ ppm): 4.75 (s, 1H), 4.61 (s, 1H), 4.18 (d, J=11.6 Hz, 1H), 3.80 (d, J=11.6 Hz, 1H), 3.40 (t, J=8.8 Hz, 1H), 2.95-3.02 (m, 1H), 2.17-2.29 (m, 2H), 1.95-1.99 (m, 2H), 2.10 (s, 3H, $CH_3$), 1.69 (s, 3H, $CH_3$), 1.17-1.64 (m, 22H), 0.98 (s, 3H, $CH_3$), 0.94 (s, 3H, $CH_3$), 0.86 (s, 3H, $CH_3$), 0.75 (s, 3H, $CH_3$).

Example 6

Synthesis of 3,23-Dihydroxy-20(29)-epoxy-lupan-28-oic acid (DA009)

To a solution of 3,23-dihydroxy-20(29)-lupen-28-oic acid (35 mg, 0.074 mmol) in THF (3 ml) was added MCPBA (73% mix, 35 mg, 0.15 mmol). After stirring at room temperature for 2 days, the reaction was quenched with saturated $NaHCO_3$ (0.5 ml). After aqueous workup, the residue was purified by column chromatography on silica gel using $CH_2Cl_2$-MeOH (v/v, 20:1) as eluent to yield the desired product as a white solid with 90% yield. $^1$H NMR (400 MHz, $CD_3OD$, δ ppm): 3.58-3.60 (m, 1H), 3.51 (d, J=11.2 Hz, 1H), 3.26-3.31 (m, 3H), 1.32-2.25 (m, 28H), 1.24 (s, 3H, $CH_3$), 1.00 (s, 3H, $CH_3$), 0.95 (s, 3H, $CH_3$), 0.89 (s, 3H, $CH_3$), 0.67 (s, 3H, $CH_3$).

Example 7

Synthesis of 20(29)-Lupene-3,23,28-triol (DA010)

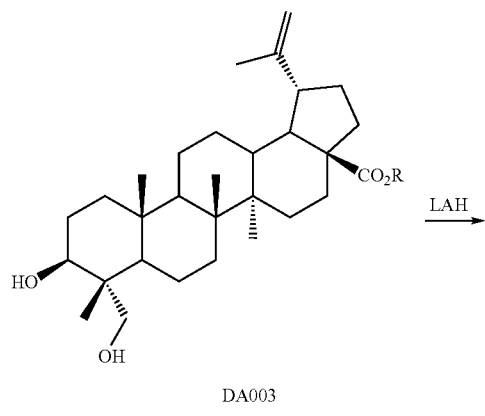

DA003

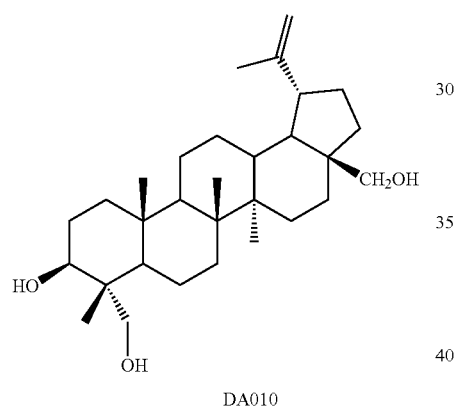

DA010

To a solution of 3,23-dihydroxy-20(29)-lupen-28-oic acid, methyl ester (30 mg, 0.062 mmol) in THF (3 ml) was added LiAlH$_4$ (12 mg, 0.31 mmol) at 0° C. The reaction was warmed up to room temperature and stirred overnight. After quenching with water (1 ml), the mixture was extracted with ethyl acetate (3×10 ml). The combined organic layer was washed with H$_2$O (1×2 ml), brine (1×2 ml), dried over sodium sulfate and concentrated under reduced pressure. The resulting residue was purified by column chromatography on silica gel using CH$_2$Cl$_2$-MeOH (v/v, 30:1) as eluent to yield the desired product as a white solid with 92% yield.

$^1$H NMR (400 MHz, CDCl$_3$, δ ppm): 4.68 (s, 1H), 4.58 (s, 1H), 3.79 (d, J=10.8 Hz, 1H), 3.73 (d, J=10.4 Hz, 1H), 3.62 (t, J=8.4 Hz, 1H), 3.42 (J=10.4 Hz, 1H), 3.33 (d, J=10.8 Hz, 1H), 2.35-2.39 (m, 1H), 1.83-1.94 (m, 4H), 1.68 (s, 3H, CH$_3$), 1.05-1.65 (m, 23H), 1.02 (s, 3H, CH$_3$), 0.98 (s, 3H, CH$_3$), 0.88 (s, 6H, 2×CH$_3$).

$^{13}$C NMR (100 MHz, CDCl$_3$, δ ppm): 150.1, 109.5, 71.9, 60.4, 50.3, 49.8, 48.6, 47.7, 42.7, 41.8, 40.8, 38.3, 37.2, 37.0, 33.9, 29.7, 29.1, 27.0, 25.1, 20.8, 19.1, 18.4, 16.4, 16.0, 14.7, 11.3, 11.2.

Example 8

Synthesis of 3,23-Diacetoxy-20(29)-lupen-28-oic acid, methyl ester (DA011); and 23-Acetoxy-3-hydroxy-20(29)-lupen-28-oic acid, methyl ester (DA012)

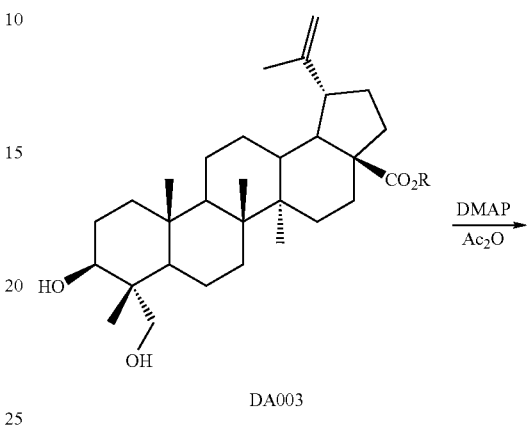

DA003

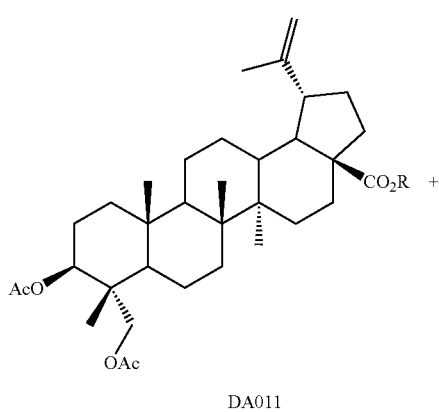

DA011

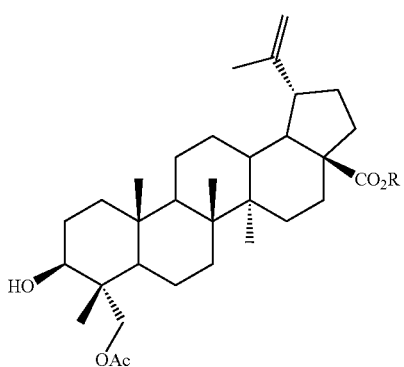

DA012

To a solution of 3,23-dihydroxy-20(29)-lupen-28-oic acid, methyl ester (50 mg, 0.10 mmol) in pyridine (1 ml) was added DMAP (cat) and Ac$_2$O (9 µL, 0.10 mmol) in an ice-water bath. After stirring at the same temperature for 0.5 h, the mixture was extracted with ethyl acetate (3×30 ml). The combined organic layer was washed with 5% HCl (2×5 ml), saturated NaHCO₃ (1×5 ml), H₂O (1×5 ml) and brine (1×5 ml). After drying over sodium sulfate, the mixture was concentrated and the resulting residue was purified by column chromatography on silica gel using petroleum-ethyl acetate to provide the desired products.

3,23-Diacetoxy-20(29)-lupen-28-oic acid, methyl ester (DA011)

¹H NMR (400 MHz, CDCl₃, δ ppm): 4.74-4.79 (m, 2H), 4.61 (s, 1H), 4.85 (d, J=11.6 Hz, 1H), 4.69 (d, J=11.6 Hz, 1H), 3.67 (s, 3H, CH₃), 2.98-3.00 (m, 1H), 2.17-2.25 (m, 2H), 2.07 (s, 3H, CH₃), 2.02 (s, 3H, CH₃), 1.87-1.90 (m, 2H), 0.96-1.73 (m, 23H), 0.93 (s, 3H, CH₃), 0.90 (s, 3H, CH₃), 0.87 (s, 3H, CH₃), 0.81 (s, 3H, CH₃).

23-Acetoxy-3-hydroxy-20(29)-lupen-28-oic acid, methyl ester (DA012)

¹H NMR (300 MHz, CDCl₃, δ ppm): 4.74 (s, 1H), 4.60 (s, 1H), 4.17 (d, J=11.6 Hz, 1H), 3.80 (d, J=11.6 Hz, 1H), 3.67 (s, 3H, CH₃), 3.40 (br, 1H), 2.98-3.02 (m, 1H), 2.13-2.25 (m, 2H), 2.09 (s, 3H, CH₃), 1.85-2.07 (m, 2H), 1.68 (s, 3H, CH₃), 1.02-1.66 (m, 21H), 0.97 (s, 3H, CH₃), 0.92 (s, 3H, CH₃), 0.86 (s, 3H, CH₃), 0.75 (s, 3H, CH₃).

Example 9

Synthesis of 23-Acetoxy-3-oxo-20(29)-lupen-28-oic acid, methyl ester (DA013)

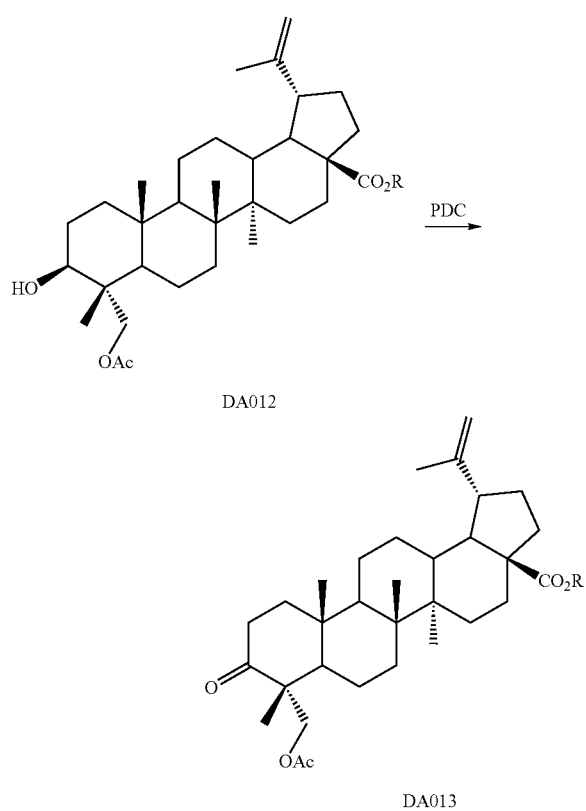

To a solution of 23-acetoxy-3-hydroxy-20(29)-lupen-28-oic acid, methyl ester (95 mg, 0.18 mmol) in CH₂Cl₂ (3 ml) was added silica gel (200 mg) and PDC (136 mg, 0.36 mmol). After stirring at room temperature overnight, the mixture was filtered through a pad of silica gel column. The filtrate was concentrated and the resulting yellow oil was purified by column chromatography on silica gel using petroleum-ethyl acetate (v/v 4:1) as eluent to yield compound the desired product as a white solid with 90% yield.

¹H NMR (300 MHz, CDCl₃, δ ppm): 4.73 (s, 1H), 4.60 (s, 1H), 4.05 (d, J=11 Hz, 1H), 4.02 (d, J=11 Hz, 1H), 3.66 (s, 3H, OCH₃), 2.98-3.00 (m, 1H), 2.42-2.47 (m, 2H), 2.25-2.24 (m, 2H), 2.02 (s, 3H, CH₃), 1.88-1.93 (m, 2H), 1.68 (s, 3H, CH₃), 1.18-1.64 (m, 18H), 0.99 (s, 3H, CH₃), 0.97 (s, 3H, CH₃), 0.96 (s, 3H, CH₃), 0.94 (s, 3H, CH₃).

Example 10

Synthesis of 23-Hydroxy-3-oxo-20(29)-lupen-28-oic acid, methyl ester (DA014)

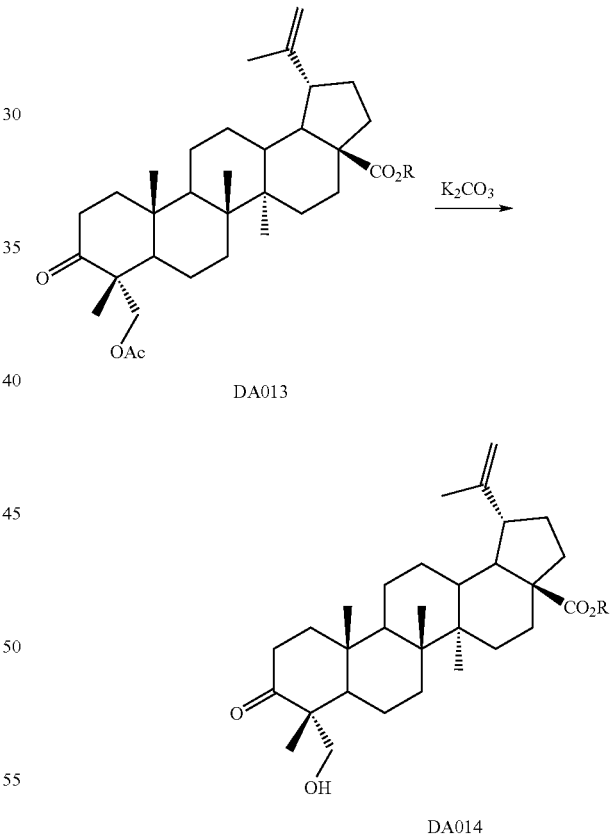

To a solution of 23-acetoxy-3-oxo-20(29)-lupen-28-oic acid, methyl ester (83 mg, 0.16 mmol) in MeOH (3 ml) was added K₂CO₃ (25 mg, 0.18 mmol). The mixture was stirred at room temperature for 3 h. The reaction was stopped and the mixture was extracted with ethyl acetate (3×30 ml). The combined organic layer was washed with H₂O (1×5 ml), brine (1×5 ml), dried over sodium sulfate, filtered and concentrated under reduced pressure. The resulting residue was purified by column chromatography on silica gel using petroleum-ethyl acetate (v/v 4:1) as eluent to yield the desired product as a white solid with 98% yield.

Example 11

Synthesis of 23-Hydroxy-3-hydroxyimino-20(29)-lupen-28-oic acid, methyl ester (DA015)

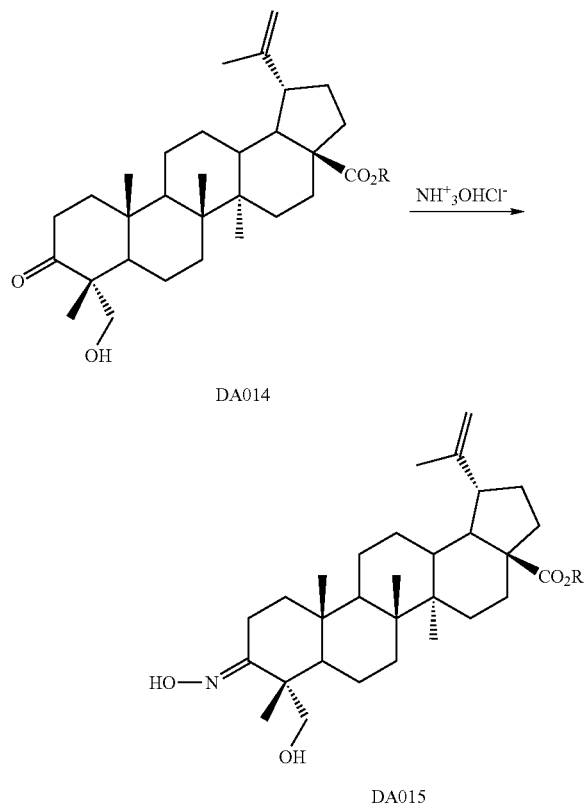

DA014

DA015

To a solution of 23-hydroxy-3-oxo-20(29)-lupen-28-oic acid, methyl ester (74 mg, 0.16 mmol) in pyridine (2 ml) was added hydroxylamine hydrochloride (44 mg, 0.64 mmol). After stirring at room temperature for 2 h, the reaction was stopped. The mixture was extracted with ethyl acetate (3×30 ml). The combined organic layer was washed with 5% HCl (2×5 ml), saturated NaHCO$_3$ (1×5 ml), H$_2$O (1×5 ml), brine (1×5 ml). After dried over sodium sulfate, filtered and concentrated, the resulting residue was purified by column chromatography on silica gel using CH$_2$Cl$_2$-MeOH (v/v, 10:1) as eluent to yield the desired product as a white solid with 98% yield.

Example 12

Synthesis of 23-Acetoxy-3-oxo-20(29)-lupen-28-oic acid (DA016)

To a solution of 23-acetoxy-3-hydroxy-20(29)-lupen-28-oic acid (100 mg, 0.20 mmol) in CH$_2$Cl$_2$ (3 ml) was added sil gel (200 mg) and PDC (147 mg, 0.40 mmol). After stirring at room temperature for 1.5 h, the reaction was stopped. The mixture was filtered through a plug of silica gel and the filtrate was concentrated. The resulting residue was purified by column chromatography on silica gel using petroleum-ethyl acetate (v/v 4:1) as eluent to yield the desired product as a white solid with 69% yield.

$^1$H NMR (300 MHz, CDCl$_3$, δ ppm): 4.75 (s, 1H), 4.61 (s, 1H), 4.07 (d, J=11 Hz, 1H), 4.02 (d, J=11 Hz, 1H), 3.03-3.06 (m, 1H), 2.45-2.51 (m, 2H), 2.28-2.33 (m, 2H), 2.03 (s, 3H), 1.70-2.00 (m, 2H), 1.67 (s, 3H, CH$_3$), 1.05-1.63 (m, 19H), 0.94-1.00 (m, 12H, 4×CH$_3$).

Example 13

Synthesis of 23-Hydroxy-3-oxo-20(29)-lupen-28-oic acid (DA018)

To a solution of 23-acetoxy-3-oxo-20(29)-lupen-28-oic acid (62 mg, 0.121 mmol) in MeOH (3 ml) was added K$_2$CO$_3$ (20 mg, 0.15 mmol). After stirring at room temperature for 2 h, the reaction was stopped. The mixture was extracted with ethyl acetate (3×30 ml), and the combined organic layer was washed with H$_2$O (1×5 ml), brine (1×5 ml), dried over sodium sulfate, filtered and concentrated. Purification by column chromatography on silica gel using CH$_2$Cl$_2$-MeOH (v/v, 60:1) as eluent yielded the desired product as a white solid with 90% yield.

$^1$H NMR (400 MHz, CDCl$_3$, δ ppm): 4.74 (s, 1H), 4.62 (s, 1H), 3.65 (d, J=11.2 Hz, 1H), 3.41 (d, J=11.2 Hz, 1H), 2.98-3.01 (m, 1H), 2.57-2.61 (m, 1H), 2.21-2.30 (m, 3H), 1.97-2.00 (m, 3H), 1.04-1.67 (m, 22H), 1.00 (s, 3H, CH$_3$), 0.98-0.99 (m, 9H, 3×CH$_3$)

Example 14

Synthesis of 23-Hydroxy-3-hydroxyimino-20(29)-lupen-28-oic acid (DA019)

To a solution of 23-hydroxy-3-oxo-20(29)-lupen-28-oic acid (24 mg, 0.051 mmol) in pyridine (2 ml) was added hydroxylamine hydrochloride (7 mg, 0.102 mmol). After stirring at room temperature for 2 h, the reaction was stopped. The mixture was extracted with ethyl acetate (3×30 ml). The combined organic layer was washed with 5% HCl (2×5 ml), saturated NaHCO$_3$ (1×5 ml), H$_2$O (1×5 ml) and brine (1×5 ml). After drying over sodium sulfate, filtered and concentrated, the mixture was purified by column chromatography on silica gel using CH$_2$Cl$_2$-MeOH (v/v, 10:1) as eluent to yield the desired product as a white solid with 84% yield.

$^1$H NMR (400 MHz, CDCl$_3$/CD$_3$OD, δ ppm): 4.72 (s, 1H), 4.60 (s, 1H), 3.59 (d, J=11.2 Hz, 1H), 3.49 (d, J=11.2 Hz, 1H), 3.73-3.81 (m, 1H), 2.96-3.06 (m, 2H), 1.78-2.26 (m, 7H), 1.69 (s, 3H, CH$_3$), 1.16-1.61 (m, 18H), 0.96-1.04 (m, 12H, 4×CH$_3$).

Example 15

Preparation of 3,23-Dihydroxy-20(29)-lupen-28-al (DA020)

Synthesis of 3,23-di-tert-butyldimethylsilioxy-20(29)-lupen-28-oic acid

To a solution of 3,23-dihydroxy-20(29)-lupen-28-oic acid in DMF was added TBSCl, imidazole and DMAP. After stirring at room temperature for 6 h, the reaction was stopped. The mixture was extracted with ethyl acetate (3×20 ml). The combined organic layer was washed with H$_2$O (6×2 ml), brine (1×2 ml), dried over sodium sulfate, filtered and concentrated. Purification by column chromatography on silica gel using petroleum-ethyl acetate (v/v 16:1) as eluent provided 3,23-di-tert-butyldimethylsilioxy-20(29)-lupen-28-oic acid as a colorless oil with 93% yield.

Synthesis of 3,23-Di-tert-butyldimethylsilioxy-20(29)-lupen-28-ol

To a solution of 3,23-di-tert-butyldimethylsilioxy-20(29)-lupen-28-oic acid (241 mg, 0.34 mmol) in THF (5 ml) was added LiAlH$_4$ (42 mg, 1.36 mmol). After stirring at room temperature for 8 h, the reaction was quenched with 5% HCl (2 ml). The mixture was extracted with ethyl acetate (3×40 ml). The combined organic layer was washed with 5% HCl (1×3 ml), saturated NaHCO$_3$ (1×3 ml), H$_2$O (1×2 ml), brine (1×2 ml), dried over sodium sulfate, filtered and concentrated. Purification by column chromatography on silica gel using CH$_2$Cl$_2$-MeOH (v/v, 50:1) as eluent provided 3,23-di-tert-butyldimethylsilioxy-20(29)-lupen-28-ol as a colorless oil with 87% yield.

Synthesis of 3,23-Di-tert-butyldimethylsilioxy-20(29)-lupen-28-al

To a solution of 3,23-di-tert-butyldimethylsilioxy-20(29)-lupen-28-ol (65 mg, 0.095 mmol) in CH$_2$Cl$_2$ (3 ml) was added PCC (26 mg, 0.12 mmol) and silica gel (130 mg). After stirring at room temperature for 2.5 h, the mixture was filtered though a silica gel column. The filtrate was concentrated to yield 3,23-di-tert-butyldimethylsilioxy-20(29)-lupen-28-al as yellow oil with 78% yield.

Synthesis of 3,23-Dihydroxy-20(29)-lupen-28-al

To a solution of 3,23-di-tert-butyldimethylsilioxy-20(29)-lupen-28-al (23 mg, 0.034 mmol) in THF/MeOH (1.5 ml/1.5 ml) was added 6 drops of concentrated HCl. After stirring at room temperature for 3.5 h, the reaction was stopped. The mixture was extracted with ethyl acetate (3×40 ml). The combined organic layer was washed with saturated NaHCO$_3$ (1×3 ml), H$_2$O (1×2 ml), brine (1×2 ml), dried over sodium sulfate, filtered and concentrated. Purification by column chromatography on silica gel using CH$_2$Cl$_2$-MeOH (v/v, 40:1) as eluent yielded the 3, 23-dihydroxy-20(29)-lupen-28-al as a white solid with 85% yield.

$^1$H NMR (400 MHz, CDCl$_3$, δ ppm): 9.67 (s, 1H), 4.75 (s, 1H), 4.63 (s, 1H), 3.71 (d, J=10.4 Hz, 1H), 3.61 (t, J=8.4 Hz, 1H), 3.41 (d, J=10.4 Hz, 1H), 2.83-2.87 (m, 1H), 1.71-2.09 (m, 4H), 1.69 (s, 3H, CH$_3$), 1.05-1.65 (m, 22H), 0.97 (s, 3H, CH$_3$), 0.91 (s, 3H, CH$_3$), 0.86 (s, 6H, 2×CH$_3$).

Example 16

Synthesis of 3,23-Dihydroxy-20(29)-lupen-28-iminol (DA021)

To a solution of 3,23-dihydroxy-20(29)-lupen-28-al (7 mg, 0.015 mmol) in pyridine (0.5 ml) was added hydroxylamine hydrochloride (2 mg, 0.031 mmol). After stirring at room temperature for 2 h, the mixture was extracted with ethyl acetate (3×10 ml). The combined organic layer was washed with 5% HCl (2×3 ml), saturated NaHCO$_3$ (1×3 ml), H$_2$O (1×2 ml) and brine (1×2 ml). After drying over sodium sulfate and concentrating under reduced pressure, the mixture was purified by column chromatography on silica gel using CH$_2$Cl$_2$-MeOH (v/v, 30:1) as eluent to yield the desired product as a white solid with 96% yield. ESI-MS (m/z), 472.34 (M+H$^+$).

$^1$H NMR (400 MHz, CDCl$_3$/CD$_3$OD, δ ppm): 7.53 (s, 1H), 4.71 (s, 1H), 4.60 (s, 1H), 3.54-3.62 (m, 2H), 3.30-3.33 (m, 1H), 2.52 (m, 1H), 1.72-2.02 (m, 4H), 1.70 (s, 3H, CH$_3$), 1.03-1.67 (m, 23H) 1.01 (s, 6H, 2×CH$_3$), 0.88 (s, 3H, CH$_3$), 0.75 (s, 3H, CH$_3$).

Example 17

Synthesis of 3,23-Diacetoxy-20(29)-lupen-28-al (DA022)

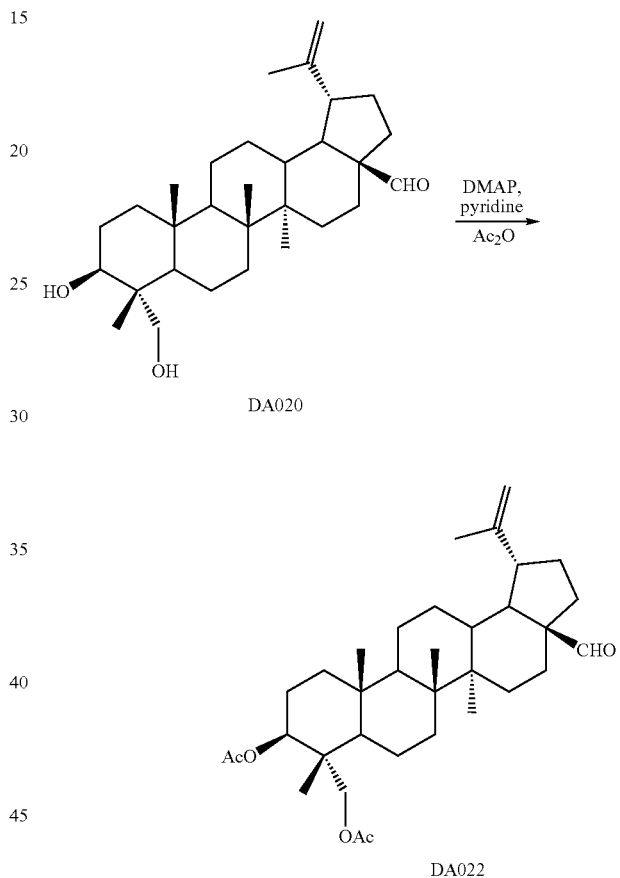

To a solution of 3,23-Dihydroxy-20(29)-lupen-28-al (22 mg, 0.053 mmol) in pyridine (1 ml) was added DMAP (cat) and Ac$_2$O (20 μL, 0.22 mmol). After stirring at room temperature for 4.5 h, the reaction was stopped. The mixture was extracted with ethyl acetate (3×10 ml). The combined organic layer was washed with 5% HCl (2×3 ml), saturated NaHCO$_3$ (1×3 ml), H$_2$O (1×2 ml), brine (1×2 ml), dried over sodium sulfate, filtered and concentrated. Purification by column chromatography on silica gel using CH$_2$Cl$_2$-MeOH (v/v, 100:1) as eluent yielded the desired product as a white solid with 92% yield.

$^1$H NMR (400 MHz, CDCl$_3$, δ ppm): 9.67 (s, 1H, CHO), 4.74-4.77 (m, 2H), 4.64 (s, 1H), 3.84 (d, J=11.2 Hz, 1H), 3.69 (d, J=11.2 Hz, 1H), 2.85-2.89 (m, 1H), 2.07 (s, 3H, CH$_3$), 2.02 (s, 3H, CH$_3$), 1.66-1.91 (m, 7H), 1.01-43 (m, 20H), 0.97 (s, 3H, CH$_3$), 0.92 (s, 3H, CH$_3$), 0.89 (s, 3H, CH$_3$), 0.81 (s, 3H, CH$_3$).

Example 18

Synthesis of
3,23-Diacetoxy-20(29)-lupen-28-benzylamine
(DA023)

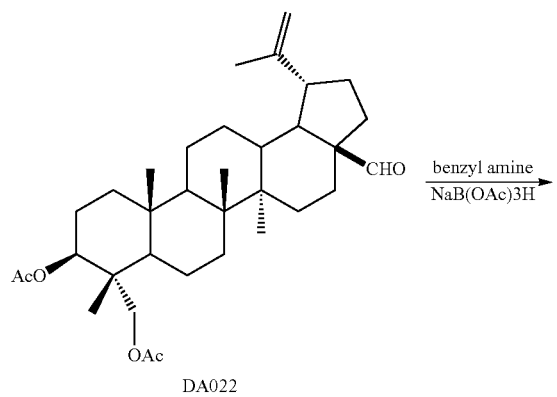

DA022

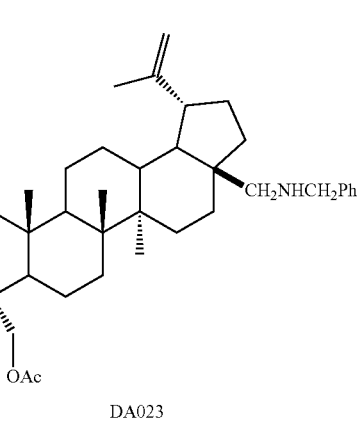

DA023

To a solution of 3,23-diacetoxy-20(29)-lupen-28-al (20 mg, 0.04 mmol) in CH$_2$Cl$_2$ (2 ml) was added benzyl amine (13 μl, 0.12 mmol), AcOH (5 μl, 0.08 mmol) and NaB(OAc)$_3$H (51 mg, 0.24 mmol). After stirring at room temperature for 9 h, the reaction was quenched with saturated NaHCO$_3$ (1 ml). The mixture was extracted with ethyl acetate (3×10 ml). The combined organic layer was washed with H$_2$O (1×2 ml) and brine (1×2 ml), dried over sodium sulfate, filtered and concentrated. Purification by column chromatography on silica gel using CH$_2$Cl$_2$-MeOH—NH$_3$OH (v/v, 60:1:0.1) as eluent yielded the desired product as a white solid with 83% yield.

$^1$H NMR (400 MHz, CDCl$_3$, δ ppm): 7.24-7.33 (m, 5H), 4.76 (dd, J=12.2, 4.4 Hz, 1H), 4.65 (s, 1H), 4.56 (s, 1H), 3.88 (d, J=14 Hz, 1H), 3.84 (d, J=11.2 Hz, 1H), 3.76 (d, J=14 Hz, 1H), 3.69 (d, J=11.2 Hz, 1H), 2.66 (d, J=11.2 Hz, 1H), 2.32-2.37 (m, 1H), 2.18 (d, J=11.2 Hz, 1H), 2.06 (s, 3H, CH$_3$), 2.01 (s, 3H, CH$_3$), 1.83-1.87 (m, 3H), 1.00-1.66 (m, 26H), 0.93 (s, 3H, CH$_3$), 0.86 (s, 3H, CH$_3$), 0.82 (s, 3H, CH$_3$), 0.81 (s, 3H, CH$_3$).

Example 19

Synthesis of
3,23-Dihydroxy-20(29)-lupen-28-benzylamine
(DA024)

To a solution of 3,23-diacetoxy-20(29)-lupen-28-benzylamine (17 mg, 0.027 mmol) in MeOH (2 ml) was added K$_2$CO$_3$ (22 mg, 0.16 mmol). After stirring at room temperature for 3 h, the reaction was stopped. The mixture was extracted with ethyl acetate (3×10 ml). The combined organic layer was washed with H$_2$O (1×2 ml) and brine (1×2 ml). After drying over sodium sulfate, filtered and concentrated, the mixture was purified by column chromatography on silica gel using CH$_2$Cl$_2$-MeOH—NH$_3$OH (v/v, 40:1:0.1) as eluent to yield the desired product as a white solid with 92% yield. ESI-MS (m/z), 547.49 (M+H$^+$).

$^1$H NMR (400 MHz, CDCl$_3$, δ ppm): 7.24-7.33 (m, 5H), 4.64 (s, 1H), 4.55 (s, 1H), 3.88 (d, J=13.6 Hz, 1H), 3.76 (d, J=13.6 Hz, 1H), 3.70 (d, J=10 Hz, 1H), 3.60 (t, J=9.2 Hz, 1H), 3.4 (d, J=10 Hz, 1H), 2.66 (d, J=11.6 Hz, 1H), 2.32-2.37 (m, 1H), 2.18 (d, J=11.6 Hz, 1H), 1.82-1.91 (m, 4H), 1.66 (s, 3H, CH$_3$), 1.02-1.62 (m, 23H), 0.93 (s, 3H, CH$_3$), 0.87 (s, 3H, CH$_3$), 0.84 (s, 3H, CH$_3$), 0.82 (s, 3H, CH$_3$).

Example 20

Preparation of 23-Formyl-3-hydroxy-20(29)-lupen-28-oic acid methyl ester (DA026)

Synthesis of 23-acetoxy-3-tert-butyldimethylsiloxy-20(29)-lupen-28-oic acid methyl ester To a solution of 23-acetoxy-3-hydroxy-20(29)-lupen-28-oic acid methyl ester DA012 (29 mg, 0.055 mmol) in DMF (1 ml) was added TBSCl (17 mg, 0.11 mmol), imidazole (10 mg, 0.14 mmol) and DMAP (cat). After stirring at room temperature for 8 h, the reaction was stopped. The mixture was extracted with ethyl acetate (3×20 ml). The combined organic layer was washed with H$_2$O (6×2 ml) and brine (1×2 ml), dried over sodium sulfate, filtered and concentrated. Purification by column chromatography on silica gel using petroleum-ethyl acetate (v/v 16:1) as eluent provided 23-acetoxy-3-tert-butyldimethylsiloxy-20(29)-lupen-28-oic acid methyl ester as a colorless oil with 93% yield.

Synthesis of 23-hydroxy-3-tert-butyldimethylsiloxy-20(29)-lupen-28-oic acid methyl ester To a solution of 23-acetoxy-3-tert-butyldimethylsiloxy-20(29)-lupen-28-oic acid methyl ester (41 mg, 0.064 mmol) in MeOH/THF (3 ml/1 ml) was added K$_2$CO$_3$ (18 mg, 0.13 mmol). After stirring at room temperature for 2 h, the reaction was stopped. The mixture was extracted with ethyl acetate (3×30 ml), and the combined organic layer was washed with H$_2$O (1×5 ml) and brine (1×5 ml). After dried over sodium sulfate, filtered and concentrated, the mixture was purified by column chromatography on silica gel using CH$_2$Cl$_2$-MeOH (v/v, 40:1, 20:1) as eluent provided 23-hydroxy-3-tert-butyldimethylsiloxy-20(29)-lupen-28-oic acid methyl ester as a white solid with 90% yield.

Synthesis of 23-formyl-3-tert-butyldimethylsiloxy-20(29)-lupen-28-oic acid methyl ester To a solution of 23-hydroxy-3-tert-butyldimethylsiloxy-20(29)-lupen-28-oic acid methyl ester (18 mg, 0.03 mmol) in CH$_2$Cl$_2$ (2 ml) was added sil gel (36 mg) and PCC (13 mg, 0.06 mmol). The reaction was stirred at room temperature for 2.5 h and stopped. The mixture was filtered through a plug of silica gel. The filtrate was concentrated and the resulting residue was purified by column chromatography on silica gel using petroleum-ethyl acetate (v/v 10:1) as eluent to yield 23-formyl-3-tert-butyldimethylsiloxy-20(29)-lupen-28-oic acid methyl ester as a white solid with 76% yield.

Synthesis of 23-formyl-3-hydroxy-20(29)-lupen-28-oic acid methyl ester

To a solution of 23-formyl-3-tert-butyldimethylsiloxy-20(29)-lupen-28-oic acid methyl ester (10 mg) in THF/MeOH (1 ml/1 ml) was added 3 drops concentrated HCl. After stirring at room temperature for 3.5 h, the reaction was stopped. The mixture was extracted with ethyl acetate (3×20 ml). The combined organic layer was washed with saturated NaHCO$_3$ (1×3 ml), H$_2$O (1×2 ml) and brine (1×2 ml). After drying over sodium sulfate, filtered and concentrated, the resulting residue was purified by column chromatography on silica gel using CH$_2$Cl$_2$-MeOH (v/v, 10:1) as eluent to yield 23-formyl-3-hydroxy-20(29)-lupen-28-oic acid methyl ester as a white solid with 82% yield.

Example 21

Synthesis of 3-Hydroxy-23-hydroxylimino-20(29)-lupen-28-oic acid methyl ester (DA027)

To a solution of 23-formyl-3-hydroxy-20(29)-lupen-28-oic acid methyl ester (10 mg, 0.021 mmol) in pyridine (1 ml) was added hydroxylamine hydrochloride (4 mg, 0.063 mmol). After stirring at room temperature for 2 h, the reaction was stopped. The mixture was extracted with ethyl acetate (3×20 ml). The combined organic layer was washed with 5% HCl (2×5 ml), saturated NaHCO$_3$ (1×5 ml), H$_2$O (1×5 ml) and brine (1×5 ml). After drying over sodium sulfate, filtered and concentrated, the resulting residue was purified by chromatography on silica gel using CH$_2$Cl$_2$-MeOH (v/v, 10:1) as eluent to yield the desired product as a white solid with 84% yield.

$^1$H NMR (400 MHz, CDCl$_3$, δ ppm): 7.24 (s, 1H), 4.74 (s, 1H), 4.60 (s, 1H), 3.67 (s, 3H, CH$_3$), 3.51-3.54 (m, 1H), 2.97-3.00 (m, 1H), 1.73-2.22 (m, 6H), 1.68 (s, CH$_3$), 1.14-1.60 (m, 20H), 1.02 (s, 3H, CH$_3$), 0.96 (s, 3H, CH$_3$), 0.92 (s, 3H, CH$_3$), 0.87 (s, 3H, CH$_3$).

Example 22

Synthesis of 23-Benzylamino-3-hydroxy-20(29)-lupen-28-oic acid methyl ester (DA028)

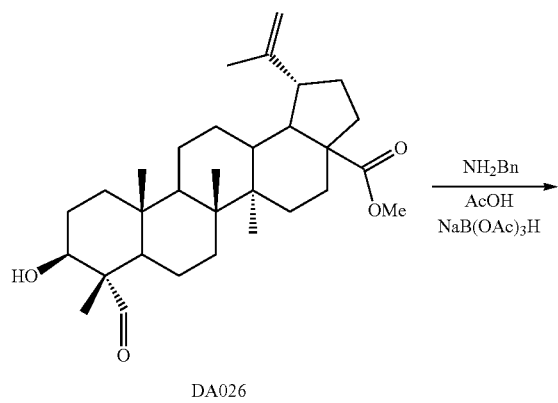

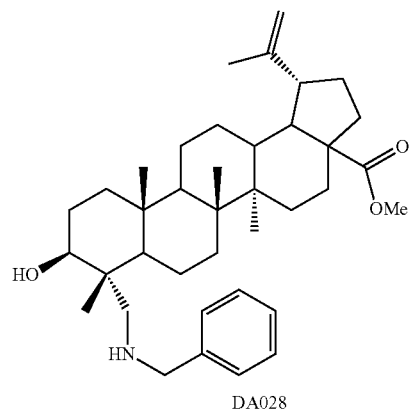

To a solution of 23-formyl-3-hydroxy-20(29)-lupen-28-oic acid methyl ester (41 mg, 0.085 mmol) in CH$_2$Cl$_2$ (4 mL) was added benzyl amine (28 μl, 0.26 mmol), AcOH (10 μl, 0.17 mmol) and NaB(OAc)$_3$H (108 mg, 0.51 mmol). After stirring at room temperature overnight, the reaction was quenched by saturated NaHCO$_3$ (1 ml). The mixture was extracted with ethyl acetate (3×10 ml). The combined organic layer was washed with H$_2$O (1×2 ml), brine (1×2 ml), dried over sodium sulfate, filtered and concentrated. Purification by column chromatography on silica gel using CH$_2$Cl$_2$-MeOH—NH$_3$OH (v/v, 30:1:0.1) as eluent yielded the desired product as a white solid with 88% yield.

$^1$H NMR (400 MHz, CDCl$_3$, δ ppm): 7.29-7.43 (m, 5H), 4.74 (s, 1H), 4.60 (s, 1H), 4.43 (d, J=5.6 Hz, 1H), 3.81 (d, J=11.6 Hz, 1H), 3.73 (d, J=11.6 Hz, 1H), 3.61-3.66 (m, 4H), 3.47-3.51 (m, 1H), 3.08 (d, J=12.0 Hz, 1H), 2.98-3.00 (m, 1H), 2.02-2.23 (m, 3H), 1.86-1.93 (m, 3H), 1.68 (s, 3H, CH$_3$), 1.12-1.60 (m, 19H), 0.95 (s, 3H, CH$_3$), 0.90 (s, 3H, CH$_3$), 0.89 (s, 3H, CH$_3$), 0.86 (s, 3H, CH$_3$).

Example 23

Synthesis of 23-Benzylamino-20(29)-lupene-3,28-diol (DA029)

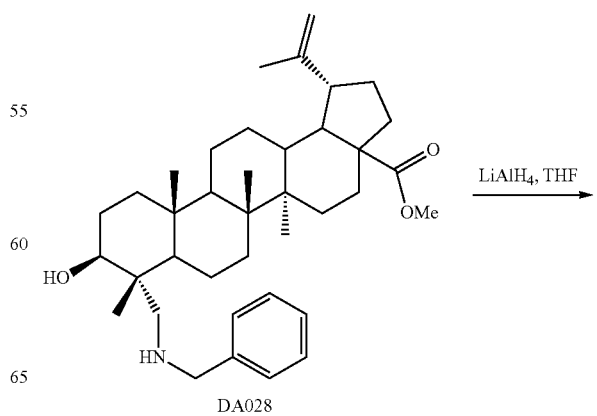

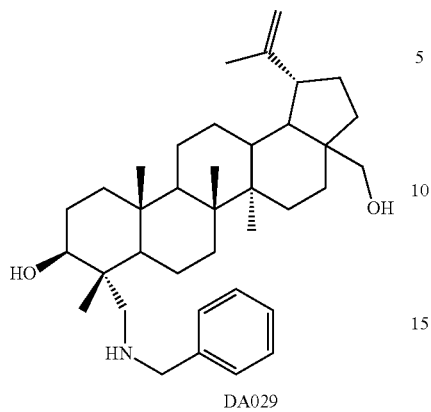

DA029

To a solution of 23-benzylamino-3-hydroxy-20(29)-lupen-28-oic acid methyl ester (25 mg, 0.043 mmol) in THF (3 ml) was added LiAlH$_4$ (9 mg, 0.22 mmol) at 0° C. After stirring at room temperature overnight, the reaction was quenched with H$_2$O (1 ml). The mixture was extracted with ethyl acetate (3×10 ml). The combined organic layer was washed with H$_2$O (1×2 ml), brine (1×2 ml), dried over sodium sulfate, filtered and concentrated. Purification by column chromatography on silica gel using CH$_2$Cl$_2$-MeOH—NH$_3$OH (v/v, 30:1:0.1) as eluent yielded the desired product as a white solid with 78% yield.

$^1$H NMR (400 MHz, CDCl$_3$, δ ppm): 7.30-7.34 (m, 5H), 4.68 (s, 1H), 4.58 (s, 1H), 3.81 (d, J=12.8 Hz, 1H), 3.78 (d, J=10.8 Hz, 1H), 3.74 (d, J=12.8 Hz, 1H), 3.49 (t, J=9.2 Hz, 1H), 3.33 (d, J=10.8 Hz, 1H), 3.09 (d, J=11.6 Hz, 1H), 2.35-2.38 (m, 1H), 2.23 (d, 11.6 Hz, 1H), 1.84-1.94 (m, 4H), 1.68 (s, 3H, CH$_3$), 1.04-1.63 (m, 25H), 1.01 (s, 3H, CH$_3$), 0.96 (s, 3H, CH$_3$), 0.89 (s, 3H, CH$_3$), 0.87 (s, 3H, CH$_3$).

Example 24

Synthesis of 28-acetoxy-3,23-dihydroxyl-20(29)-lupene (DA033)

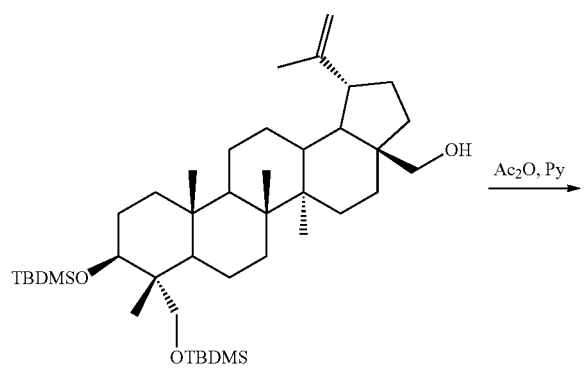

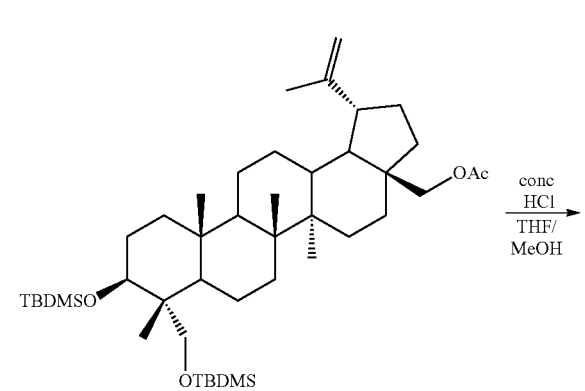

DA033

To a solution of 3,23-di-tert-butyldimethylsiloxy-20(29)-lupen-28-ol (393 mg, 0.86 mmol) in 4 mL pyridine, was added acetic anhydride (161 uL, 1.72 mmol). After stirring at room temperature for 4 h, the reaction was diluted with 300 mL of ethyl acetate. The resulting ethyl acetate solution was washed with 5% HCl (5 mL×6), saturated sodium bicarbonate (5 mL×1), water (5 mL×1), brine (5 mL x1) and dried over sodium sulfate. Column chromatography on silica gel provided the desired product (390 mg) as a white solid.

The solid was dissolved in THF/MeOH (3 mL each), and 6 drops of concentrated HCl was added. The resulting mixture was stirred at room temperature for 3 h and quenched with saturated sodium bicarbonate. After aqueous workup and purification by column chromatography on silica gel, the desired product was obtained as a white solid.

$^1$H NMR (300 MHz, CDCl$_3$, δ ppm): 4.68 (s, 1H), 4.58 (s, 1H), 4.24 (d, J=10.2 Hz, 1H), 3.84 (d, J=10.2 Hz, 1H), 3.69 (d, J=10.4 Hz, 1H), 3.60 (t, J=7.7 Hz, 1H), 3.40 (d, J=10.4 Hz, 1H), 2.73 (br, 2H), 2.39-2.48 (m, 1H), 2.13 (s, 3H, CH$_3$), 1.70-2.04 (m, 6H), 1.67 (s, 3H, CH$_3$), 1.04-1.63 (m, 29H), 1.02 (s, 3H, CH$_3$), 0.96 (s, 3H, CH$_3$), 0.85 (s, 6H, 2×CH$_3$)

$^{13}$C NMR (75 MHz, CDCl$_3$, δ ppm): 172.3, 150.7, 110.5, 77.2, 72.5, 63.4, 50.9, 50.4, 49.3, 48.3, 46.9, 43.3, 42.4, 41.4, 39.0, 38.1, 37.6, 35.1, 34.5, 30.3, 30.1, 27.6, 27.5, 25.7, 21.6, 21.4, 19.7, 19.0, 17.0, 16.6, 15.4, 11.8.

Example 25

Synthesis of 28-acetoxy-3,23-dihydroxyl-20(29)-epoxy-lupane (DA034)

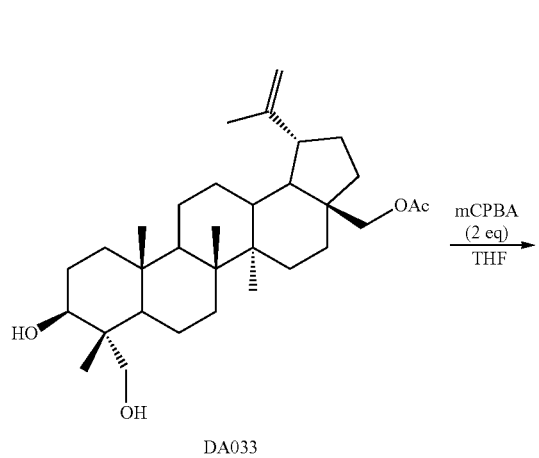

Example 26

Synthesis of 20(29)-epoxy-lupane-3,23,28-triol (DA035)

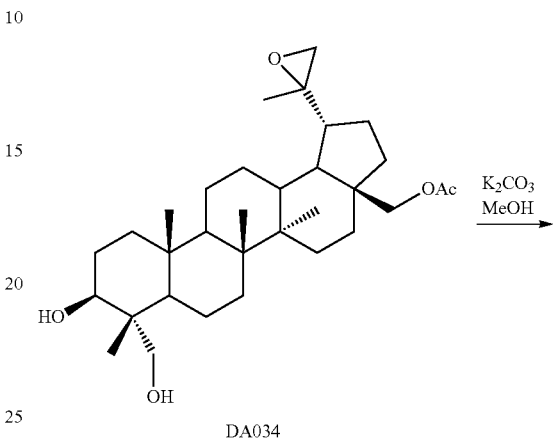

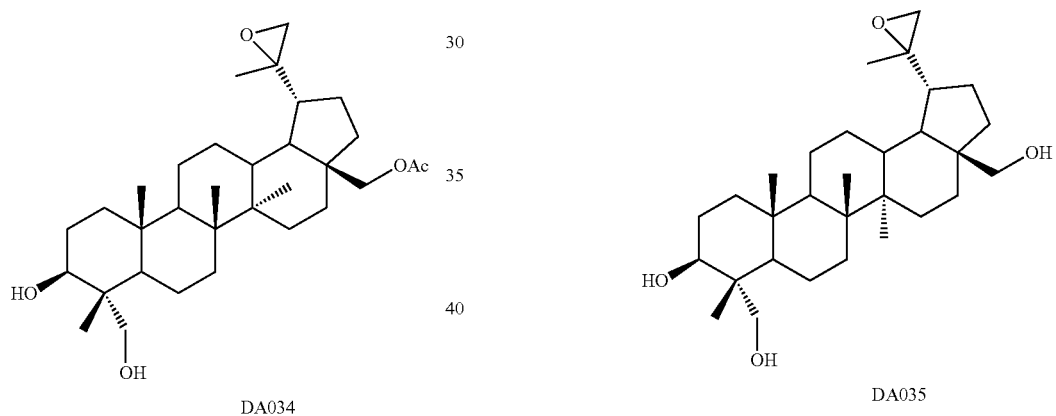

To a solution of 28-acetoxy-3,23-dihydroxyl-20(29)-lupene (216 mg, 0.43 mmol) in 4 mL THF, was added mCPBA (149 mg, 0.86 mmol) and the resulting mixture was stirred at room temperature overnight. The reaction was quenched with aqueous sodium bicarbonate and diluted with 300 mL ethyl acetate. The ethyl acetate layer was washed with saturated sodium bicarbonate (10 mL×4), water (10 mL×1), brine (10 ml x1) and dried over sodium sulfate. Purification by column chromatography on silica gel provided the desired epoxide product (200 mg) as a white solid.

$^1$H NMR (300 MHz, CDCl$_3$, δ ppm): 4.22 (d, J=10.2 Hz, 1H), 3.59-3.72 (m, 3H), 3.40 (d, J=10.2 Hz, 1H), 2.57-2.64 (m, 3H), 2.05 (s, 3H, CH$_3$), 1.26-1.98 (m, 26H), 1.24 (s, 3H, CH$_3$), 1.03 (s, 3H, CH$_3$), 0.96 (s, 3H, CH$_3$), 0.88 (s, 3H, CH$_3$), 0.86 s, 3H, CH$_3$).

$^{13}$C NMR (75 MHz, CDCl$_3$, δ ppm): 172.1, 77.1, 72.4, 63.1, 60.7, 57.7, 50.8, 50.4, 50.3, 47.2, 46.7, 43.3, 42.4, 41.4, 39.0, 37.6, 37.2, 34.9, 34.5, 30.3, 27.5, 27.4, 26.4, 21.6, 21.5, 19.0, 18.7, 17.0, 16.6, 15.2, 11.9.

To a solution of 28-acetoxy-3,23-dihydroxyl-20(29)-epoxy-lupane (30 mg, 0.058 mmol) in 2 mL methanol was added potassium carbonate (16 mg, 0.12 mmol) and the resulting mixture was stirred at room temperature for 6 h. The mixture was diluted with ethyl acetate (200 mL) and washed with water (5 mL×3), brine (5 mL×1) and dried over sodium sulfate. Purification by column chromatography on silica gel gave the desired product as a white solid.

$^1$H NMR (300 MHz, CD$_3$OD, δ ppm): 3.79 (d, J=11.0 Hz, 1H), 3.68-3.74 (m, 1H), 3.63 (d, J=11.0 Hz, 1H), 3.40 (d, J=11.0 Hz, 1H), 3.28 (d, J=11.0 Hz, 1H), 2.74-2.78 (m, 2H), 2.00-2.10 (m, 4H), 1.40-1.87 (m, 24H), 1.35 (s, 3H, CH$_3$), 1.19 (s, 3H, CH$_3$), 1.13 (s, 3H, CH$_3$), 1.02 (s, 3H, CH$_3$), 0.80 (s, 3H, CH$_3$).

$^{13}$C NMR (75 MHz, CD$_3$OD, δ ppm): 72.5, 65.9, 60.6, 58.9, 56.8, 50.3, 48.0, 47.6, 46.8, 46.1, 42.6, 42.1, 40.8, 38.4, 36.7, 36.4, 33.6, 33.5, 29.0, 26.9, 26.6, 26.3, 25.7, 20.7, 17.8, 17.0, 15.7, 15.2, 13.8, 11.3.

Example 27

Synthesis of 3,23,30-trihydroxy-20(29)-lupen-28-oic acid, methyl ester (DA037)

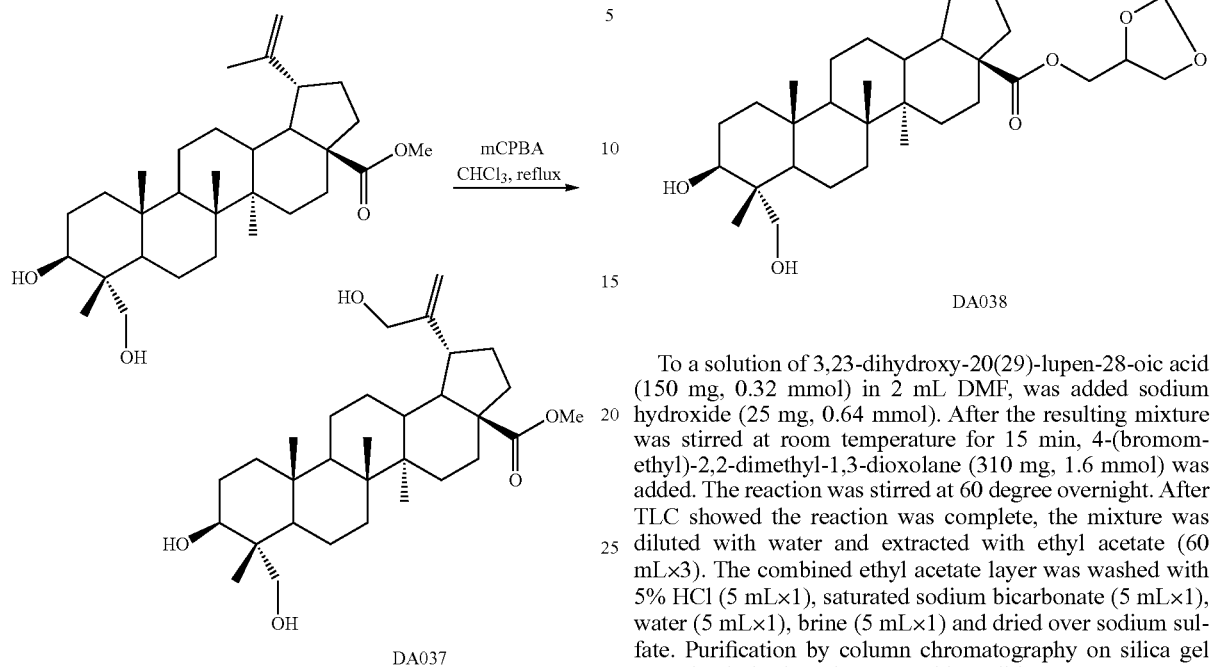

To a solution of 3,23-dihydroxy-20(29)-lupen-28-oic acid, methyl ester (240 mg, 0.49 mmol) dissolved in 20 mL chloroform, was added mCPBA (176 mg, 0.74 mmol). The resulting mixture was refluxed overnight. The reaction was quenched with aqueous sodium bicarbonate and diluted with 120 mL ethyl acetate. The ethyl acetate layer was washed with saturated sodium carbonate (5 mL×2), water (5 mL×1), brine (5 mL×1) and dried over sodium sulfate. Purification by column chromatography on silica gel provided the desired product as a white solid.

$^1$H NMR (300 MHz, CD$_3$OD, δ ppm): 5.08 (s, 1H), 4.15 (s, 2H), 3.67-3.72 (m, 1H), 3.62 (d, J=10.9 Hz, 1H), 3.37-3.42 (m, 4H), 2.95-3.01 (m, 1H), 2.33-2.37 (m, 2H), 1.20-2.95 (m, 25H), 1.13 (s, 3H, CH$_3$), 1.04 (s, 3H, CH$_3$), 1.00 (s, 3H, CH$_3$), 0.79 (s, 3H, CH$_3$).

$^{13}$C NMR (75 MHz, CD$_3$OD, δ ppm): 176.8, 154.8, 105.9, 72.5, 66.0, 63.9, 56.6, 50.6, 50.5, 49.9, 42.7, 42.2, 42.0, 40.5, 38.4, 38.3, 36.7, 36.4, 33.7, 32.1, 31.7, 29.5, 26.6, 26.3, 20.9, 17.8, 15.8, 15.3, 13.8, 11.2.

Example 28

Synthesis of 3,28-dihydroxy-20(29)-lupen-28-oic acid, 2,2-dimethyl-1,3-dioxolane-4-yl-methylester (DA038)

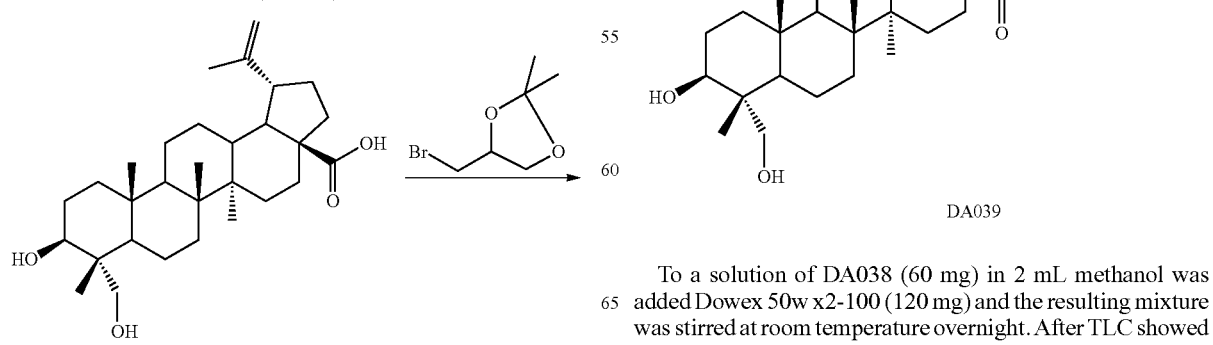

To a solution of 3,23-dihydroxy-20(29)-lupen-28-oic acid (150 mg, 0.32 mmol) in 2 mL DMF, was added sodium hydroxide (25 mg, 0.64 mmol). After the resulting mixture was stirred at room temperature for 15 min, 4-(bromomethyl)-2,2-dimethyl-1,3-dioxolane (310 mg, 1.6 mmol) was added. The reaction was stirred at 60 degree overnight. After TLC showed the reaction was complete, the mixture was diluted with water and extracted with ethyl acetate (60 mL×3). The combined ethyl acetate layer was washed with 5% HCl (5 mL×1), saturated sodium bicarbonate (5 mL×1), water (5 mL×1), brine (5 mL×1) and dried over sodium sulfate. Purification by column chromatography on silica gel gave the desired product as a white solid.

Example 29

Synthesis of 3,23-dihydroxy-20(29)-lupen-28-oic acid, 2,3-dihydroxypropyl ester (DA039)

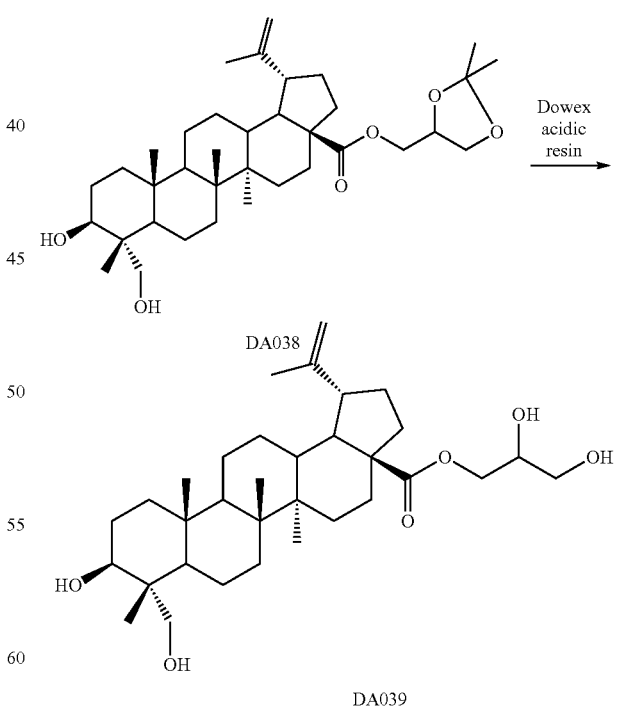

To a solution of DA038 (60 mg) in 2 mL methanol was added Dowex 50w x2-100 (120 mg) and the resulting mixture was stirred at room temperature overnight. After TLC showed that the reaction was complete, the reaction was stopped and filtered to remove the Dowex resin. The filtrate was concentrated and purified by column chromatography on silica gel to give the desired product as a white solid.

¹H NMR (300 MHz, CD₃OD, δ ppm): 4.83 (s, 1H), 4.71 (s, 1H), 4.14-4.30 (m, 2H), 3.92-3.96 (m, 1H), 3.67-3.73 (m, 3H), 3.62 (d, J=10.9 Hz, 1H), 3.39 (d, J=10.9 Hz, 1H), 3.12-3.16 (m, 1H), 2.35-2.41 (m, 2H), 1.98-2.07 (m, 2H), 1.81 (s, 3H, CH₃), 1.27-1.78 (m, 24H), 1.12 (s, 3H, CH₃), 1.06 (s, 3H, CH₃), 1.00 (s, 3H, CH₃), 0.79 (s, 3H, CH₃).

¹³C NMR (75 MHz, CD₃OD, δ ppm): 176.2, 150.5, 109.0, 72.6, 70.0, 66.0, 64.7, 63.1, 56.7, 50.6, 49.3, 42.3, 42.0, 40.6, 38.4, 38.3, 36.8, 36.6, 33.7, 31.8, 30.3, 29.5, 26.2, 25.5, 20.8, 18.2, 17.8, 15.8, 15.4, 13.8, 11.3.

Example 30

Synthesis of 3,23-dihydroxy-20(29)-lupen-28-oic acid, 2-hydroxy-ethyl ester (DA040)

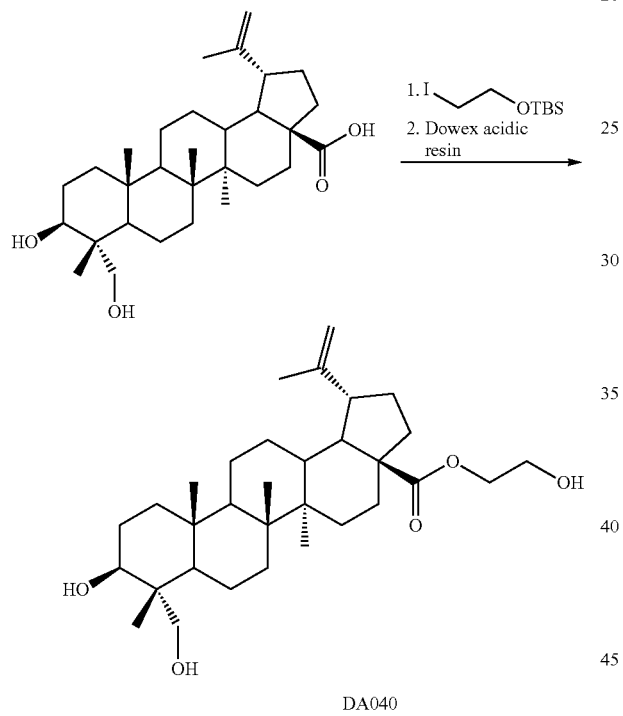

DA040

To a solution of 3,23-dihydroxy-20(29)-lupen-28-oic acid (100 mg, 0.21 mmol) in 2 mL DMF, was added potassium carbonate (58 mg, 0.42 mmol) and 2-(tert-butyldimethylsiloxy)-ethyl iodide (121 mg, 0.42 mmol). The mixture was stirred at room temperature overnight. Aqueous workup followed by purification by column chromatography on silica gel gave the desired product (44 mg) as a white solid.

The white solid was dissolved in 4 mL of MeOH and Dowex 50wx2-100 (88 mg) was added. After stirring at room temperature overnight, the mixture was filtered. The filtrate was concentrated and purified by column chromatography to give the desired product as a white solid.

¹H NMR (300 MHz, CDCl₃, 2 drops CD₃OD, δ ppm): 4.70 (s, 1H), 4.57 (s, 1H), 4.11-4.23 (m, 2H), 3.77 (t, J=4.8 Hz, 2H), 3.62 (d, J=10.4 Hz, 1H), 3.52-3.58 (m, 1H), 3.33 (d, J=10.4 Hz, 1H), 2.92-2.98 (m, 1H), 2.22-2.25 (m, 3H), 1.84-1.91 (m, 2H), 1.65 (s, 3H, CH₃), 0.97-1.65 (m, 12H), 0.93 (s, 3H, CH₃), 0.88 (s, 3H, CH₃), 0.82 (s, 3H, CH₃), 0.81 (s, 3H, CH₃).

¹³C NMR (75 MHz, CDCl₃, 2 drops CD₃OD, δ ppm): 177.3, 150.9, 110.2, 77.1, 72.2, 66.0, 61.7, 57.1, 51.0, 50.5, 49.9, 47.5, 42.9, 42.2, 41.2, 38.9, 38.7, 37.6, 37.5, 34.5, 32.6, 31.1, 30.2, 27.1, 26.0, 21.4, 19.9, 18.9, 17.0, 16.4, 15.2, 11.8.

Example 31

Synthesis of 3,23-diacetoxy-20(29)-lupen-28-oic acid, benzyl amide (DA041)

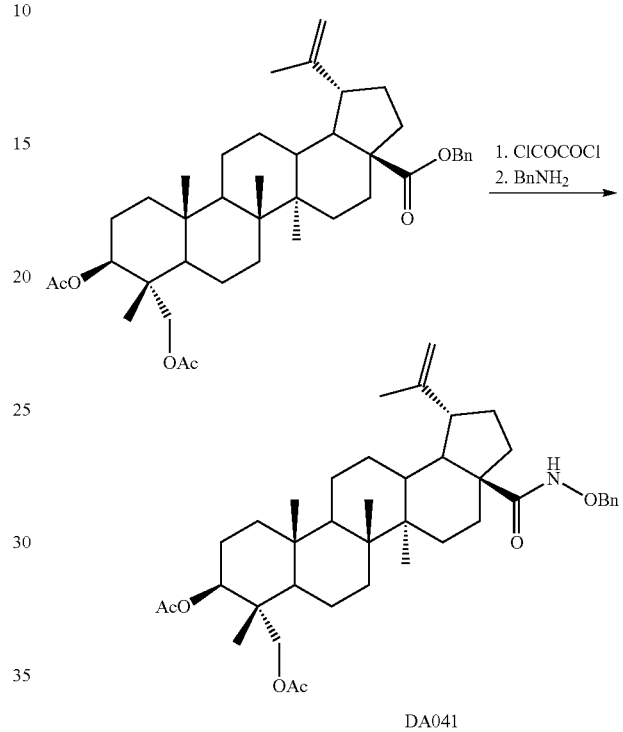

DA041

To a solution of 3,23-diacetoxy-20(29)-lupen-28-oic acid (100 mg, 0.18 mmol) in 5 mL dry dichloromethane, was added 0.1 mL oxalyl chloride at room temperature, and the resulting mixture was stirred at room temperature for 6 h. Benzyl amine (5 mL) and triethylamine (0.2 mL) were then added and the reaction was stirred overnight. After aqueous workup and purification by column chromatography, the desired product was obtained as a white solid.

¹³C NMR (75 MHz, CDCl₃, δ ppm): 176.4, 171.6, 171.2, 151.5, 139.7, 129.2, 128.3, 127.9, 110.0, 75.1, 66.0, 56.2, 51.3, 50.8, 48.7, 47.3, 43.9, 43.0, 41.3, 41.2, 39.0, 38.6, 38.3, 37.6, 34.6, 34.3, 31.5, 30.0, 26.2, 23.7, 21.8, 21.6, 21.5, 20.1, 18.5, 17.2, 16.7, 15.1, 13.5.

Example 32

Synthesis of 3,23-dihydroxy-20(29)-lupen-28-oic acid, benzyl amide (DA042)

To a solution of 3,23-diacetoxy-20(29)-lupen-28-oic acid, benzyl amide (121 mg) in 3 mL THF and 1.5 mL methanol, was added aqueous sodium hydroxide (1 M, 1.5 mL). The resulted mixture was stirred at room temperature for 4 h. After aqueous workup and purification by column chromatography, the resulting product was obtained as a white solid (84% for 2 steps).

¹³C NMR (75 MHz, CDCl₃, δ ppm): 176.6, 151.4, 139.6, 129.2, 128.3, 127.9, 109.9, 77.3, 72.5, 56.2, 51.2, 50.7, 50.6, 47.2, 43.8, 43.0, 42.3, 41.3, 39.0, 38.2, 37.6, 34.7, 34.3, 31.4, 30.0, 27.4, 26.2, 21.5, 20.1, 19.0, 17.1, 16.7, 15.2, 11.9.

Example 33

Synthesis of Compound DA043 from DA001

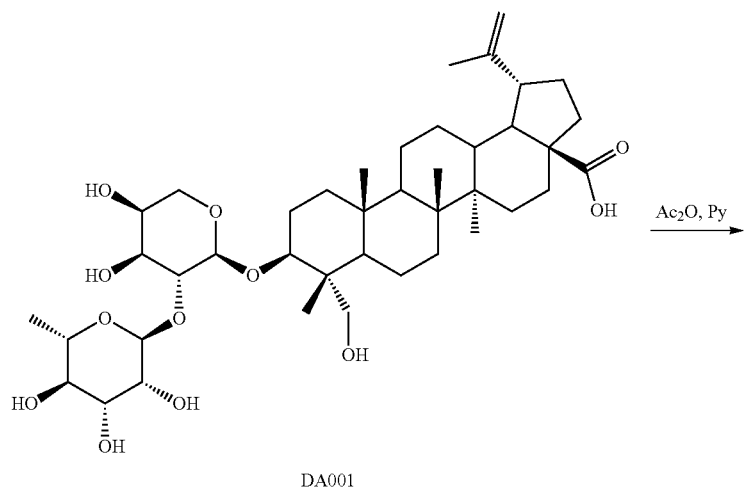

DA001

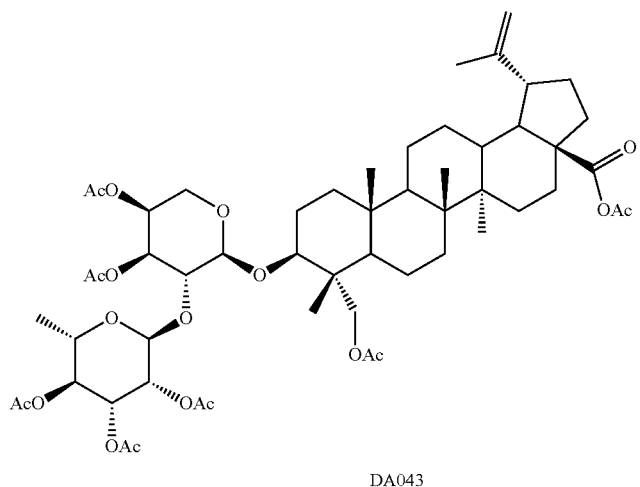

DA043

A solution of DA001 (100 mg) in 2 mL pyridine and 0.5 mL acetic anhydride was stirred at room temperature for overnight. The mixture was diluted was ethyl acetate and washed with 5% HCl(×3), saturated sodium bicarbonate (×1), brine (×1) and dried over sodium sulfate. Purification by column chromatography on silica gel provided the desired product as a white solid.

$^{13}$C NMR (75 MHz, CDCl$_3$, δ ppm): 172.0, 171.0, 170.9, 170.8, 170.7, 170.6, 170.2, 167.7, 150.4, 110.5, 104.1, 98.6, 82.4, 74.7, 72.5, 71.6, 70.1, 69.1, 68.4, 67.6, 65.7, 63.3, 58.3, 51.3, 49.7, 48.6, 47.0, 42.9, 42.5, 41.3, 39.2, 38.5, 37.3, 36.6, 34.5, 32.0, 30.8, 30.2, 26.2, 26.0, 22.9, 21.6, 21.5, 21.5, 21.3, 21.3, 21.2, 20.0, 18.5, 17.9, 17.2, 16.5, 15.0, 13.0.

Example 34

Synthesis of Compound DA044

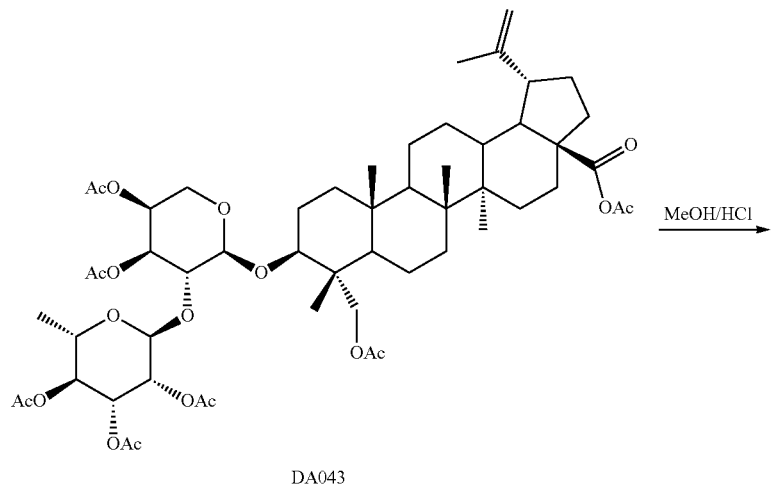

DA043

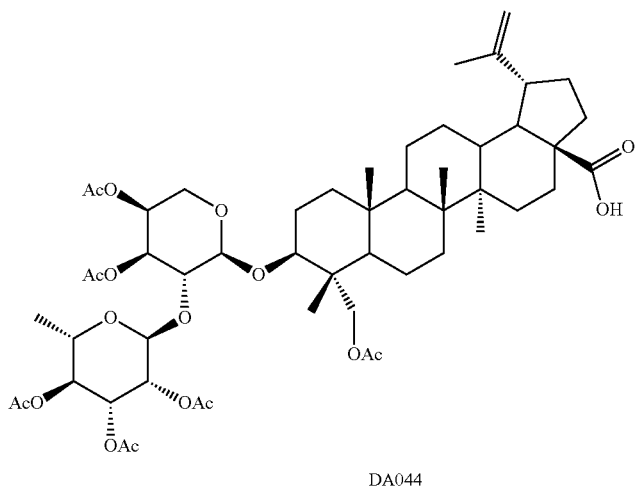

DA044

To a solution of DA043 (80 mg) in 3 mL THF and 3 mL MeOH was added 1% HCl (2 mL) and the reaction was stirred at room temperature overnight. The mixture was diluted with ethyl acetate, washed with water (×1), brine (×1) and dried over sodium sulfate. Purification by column chromatography on silica gel provided the desired product as a white solid.

$^{13}$C NMR (75 MHz, CDCl$_3$, δ ppm): 182.2, 171.0, 171.0, 170.9, 170.7, 170.6, 170.2, 151.0, 110.3, 104.1, 98.7, 82.5, 74.9, 72.4, 71.6, 70.1, 69.2, 68.4, 67.7, 65.7, 63.3, 56.9, 51.3, 49.8, 48.6, 47.5, 42.9, 42.5, 41.3, 39.2, 39.0, 37.6, 37.3, 34.6, 32.7, 31.1, 30.2, 26.3, 26.1, 21.6, 21.5, 21.5, 21.4, 21.3, 21.2, 19.9, 18.5, 17.9, 17.2, 16.5, 15.1, 13.0.

Example 35

Synthesis of Compound DA045

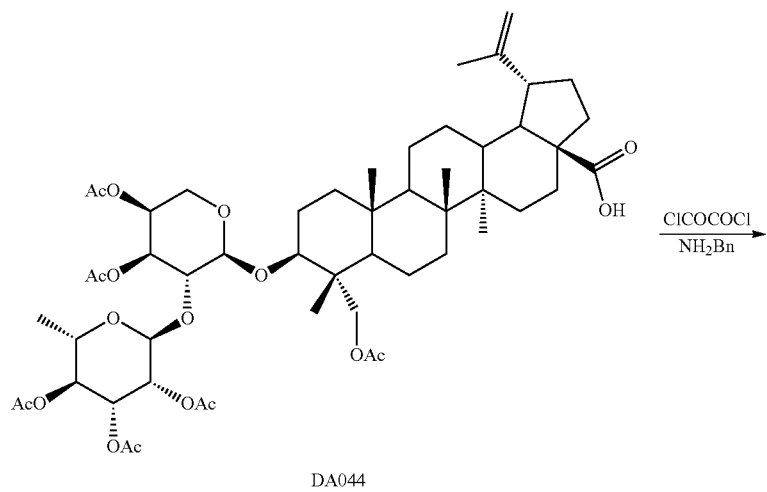

DA044

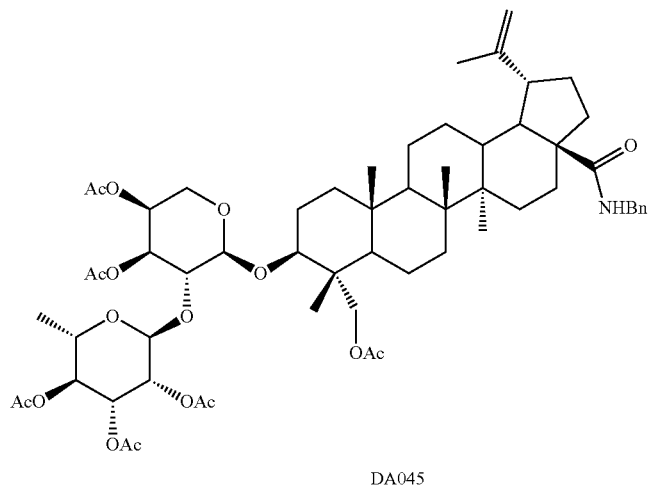

DA045

To a solution of DA044 (190 mg) in 2 mL dry dichloromethane under nitrogen, was added oxalyl chloride (0.2 mL) and the resulting mixture was stirred at room temperature for 6 h. The reaction was cooled to 0 degree Celsius, and benzylamine (5 mL), triethylamine (0.4 mL) were added. After stirring overnight, the reaction was stopped. Aqueous workup and purification by column chromatography on silica gel provided the desired amide product as a white solid.

The white product (180 mg) was dissolved in 3 mL THF and 1.5 mL methanol. Aqueous sodium hydroxide (1 M, 1.5 mL) was added and the resulting mixture was allowed to stir at room temperature overnight. Aqueous workup and purification by column chromatography on silica gel provided the desired product as a white solid.

$^{13}$C NMR (75 MHz, CD$_3$OD, δ ppm): 179.0, 152.4, 141.2, 129.5, 128.6, 128.0, 110.1, 104.3, 102.0, 82.4, 76.7, 74.0, 73.7, 72.2, 72.1, 70.2, 69.2, 64.8, 64.7, 57.1, 52.1, 51.5, 48.1, 44.1, 44.0, 43.8, 43.7, 42.0, 39.5, 39.0, 37.9, 35.1, 34.3, 32.0, 30.6, 27.1, 26.8, 22.3, 19.8, 18.9, 18.1, 17.4, 16.9, 15.2, 13.6.

Example 36

Preparation of Compounds DA046 and DA047

Compounds DA046 and DA047 were prepared by reacting DA044 and 1,2-diaminoethane using the similar procedure as described for compound DA045 in Example 36.

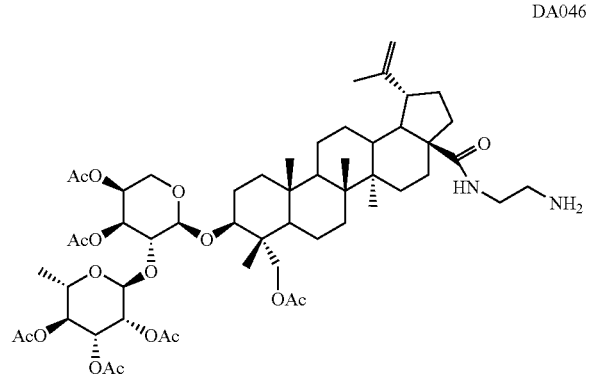

DA046

$^{13}$C NMR (75 MHz, CD$_3$OD, δ ppm) of compound DA046: 180.1, 172.7, 172.1, 172.0, 171.9, 171.8, 171.6, 152.4, 110.2, 104.8, 99.4, 83.0, 75.7, 74.0, 72.3, 71.0, 70.3, 69.7, 68.5, 66.6, 64.1, 57.2, 52.4, 51.5, 49.6, 48.3, 43.6, 43.3, 42.1, 41.8, 41.1, 40.0, 39.4, 39.1, 38.1, 35.4, 34.2, 32.0, 30.7, 27.1, 27.0, 22.3, 21.1, 21.0, 20.9, 20.8, 20.8, 20.7, 19.8, 19.2, 18.0, 17.4, 16.9, 15.2, 13.4.

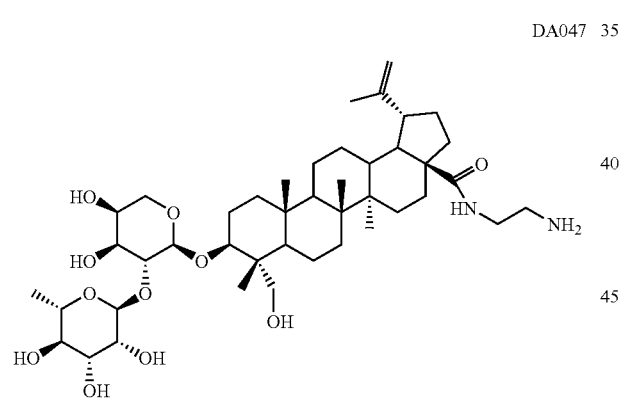

DA047

$^{13}$C NMR (75 MHz, DMSO-d$_6$, δ ppm) of compound DA047: 176.0, 150.8, 109.2, 102.8, 99.9, 79.3, 74.2, 72.7, 72.0, 70.4, 70.3, 68.1, 67.7, 64.2, 62.4, 54.9, 50.0, 49.7, 46.4, 46.2, 42.3, 41.9, 40.2, 38.4, 37.6, 36.6, 36.1, 33.5, 32.3, 30.3, 28.9, 25.4, 25.2, 20.5, 19.0, 17.7, 17.0, 16.4, 15.8, 14.2, 12.8.

Example 37

DA001 Exhibits NMDA Receptor Antagonist Activity Via Whole Cell Patch Clamp

As shown in FIG. 1, whole cell patch clamp studies were conducted to measure the effect of DA001 (10 μg/ml) on NMDA receptor activation by measuring the ion current across the surface of hippocampal neurons in the presence of toxic dose of NMDA. The NMDA receptor is a gated ion channel, which allows inflow of current during a nerve impulse. Antagonists to the receptor would prevent the inflow of current. DMSO was used as the solvent control.

Example 38

DA001 Inhibits NMDA Receptor Activity in Rat Primary Cortical Neurons

Figure 2:
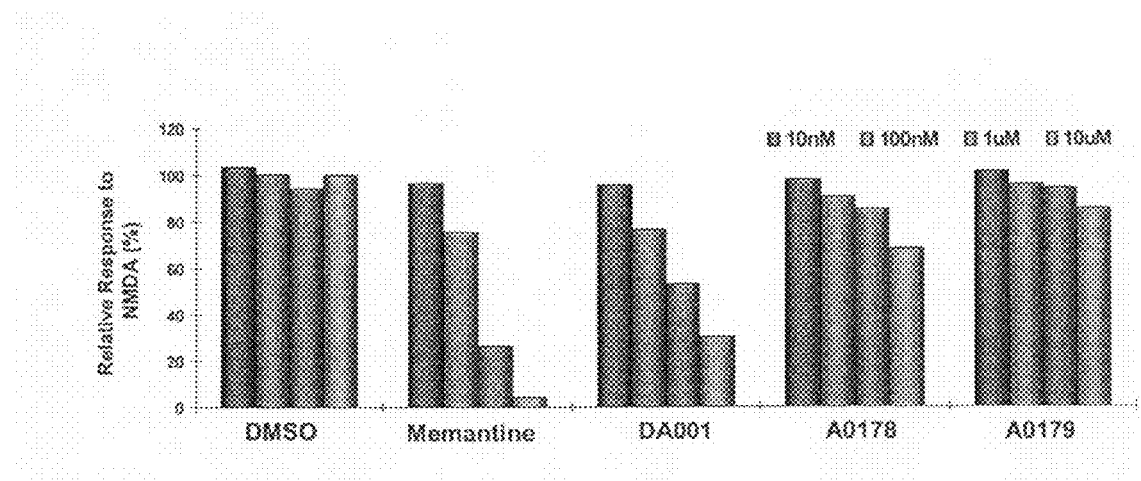
FIG. 2. Embryonic rat primary cortical neuron cultures 11 days in vitro (DIV) were treated with 10 μM glycine and 20 μM NMDA in the absence or presence of DA001 and memantine. Relative fluorescence units were measured and calculated as percentage in relative response to NMDA. Compounds A0178 and A0179 were isolated from the same herb but only DA001 showed a relative inhibitory effect on NMDA-induced current using the FLIPR assay.

NMDA receptor inhibition was determined using a fluorometric imaging plate reader (FLIPR). Primary rat cortical neurons were treated with NMDA to activate the NMDA receptor. NMDA receptor activation in response to NMDA treatment resulted in Ca$^{2+}$ influx, which was measured in relative fluorescence units. As indicated in FIG. 2, DA001 inhibits Ca$^{2+}$ influx in a dose-dependant manner. Memantine, a known NMDA receptor antagonist was included as a positive control. A0178 and A0179 are structurally related compounds isolated from the same herb along with DA001.

Example 39

DA001 Potentiates the Calcium Current Induced by Synaptic Activity

Figure 3:
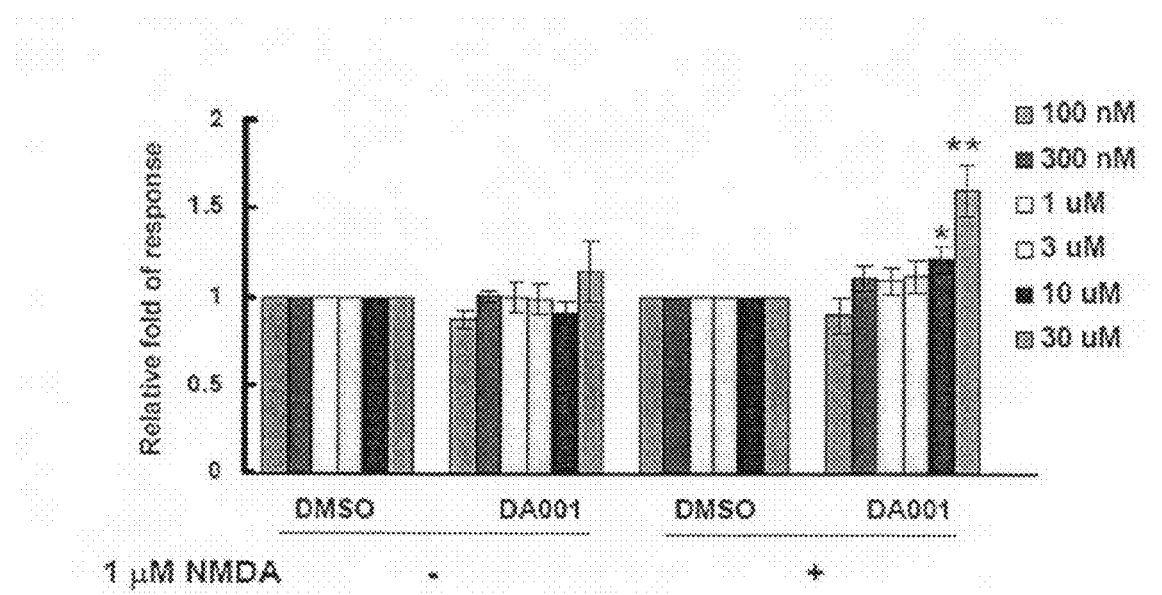
FIG. 3. DA001 potentiates the calcium current induced by 1 μM NMDA (synaptic activity). Embryonic rat primary cortical neuron cultures 9-13 days in vitro (DIV) were incubated in a buffer consisting of 10 mM HEPES pH 7.4, probenecid, and the calcium sensitive fluorescent dye Fluo4-AM (4 mM) for 1 h at 37° C. DA001 was added to the cells in the presence or absence of NMDA (1 μM). The change in fluorescent activity was monitored for 2 minutes using the FLIPR. Data is represented in average fold of response±standard deviation as compared to solvent control (DMSO).* indicates P<0.05, ** indicates P<0.005, as calculated by t-test.

As shown in FIG. 3, embryonic rat primary cortical neuron cultures 9-13 days in vitro (DIV) were incubated in a buffer consisting of 10 mM HEPES pH 7.4, probenecid, and the calcium sensitive fluorescent dye Fluo4-AM (4 mM) for 1 h at 37° C. DA001 was added to the cells in the presence or absence of NMDA (1 μM). The change in fluorescent activity was monitored for 2 minutes using the FLIPR. Data were represented in average fold of response±standard deviation as compared to solvent control (DMSO). * indicates P<0.05, ** indicates P<0.005, as calculated by t-test.

Example 40

Figure 4:
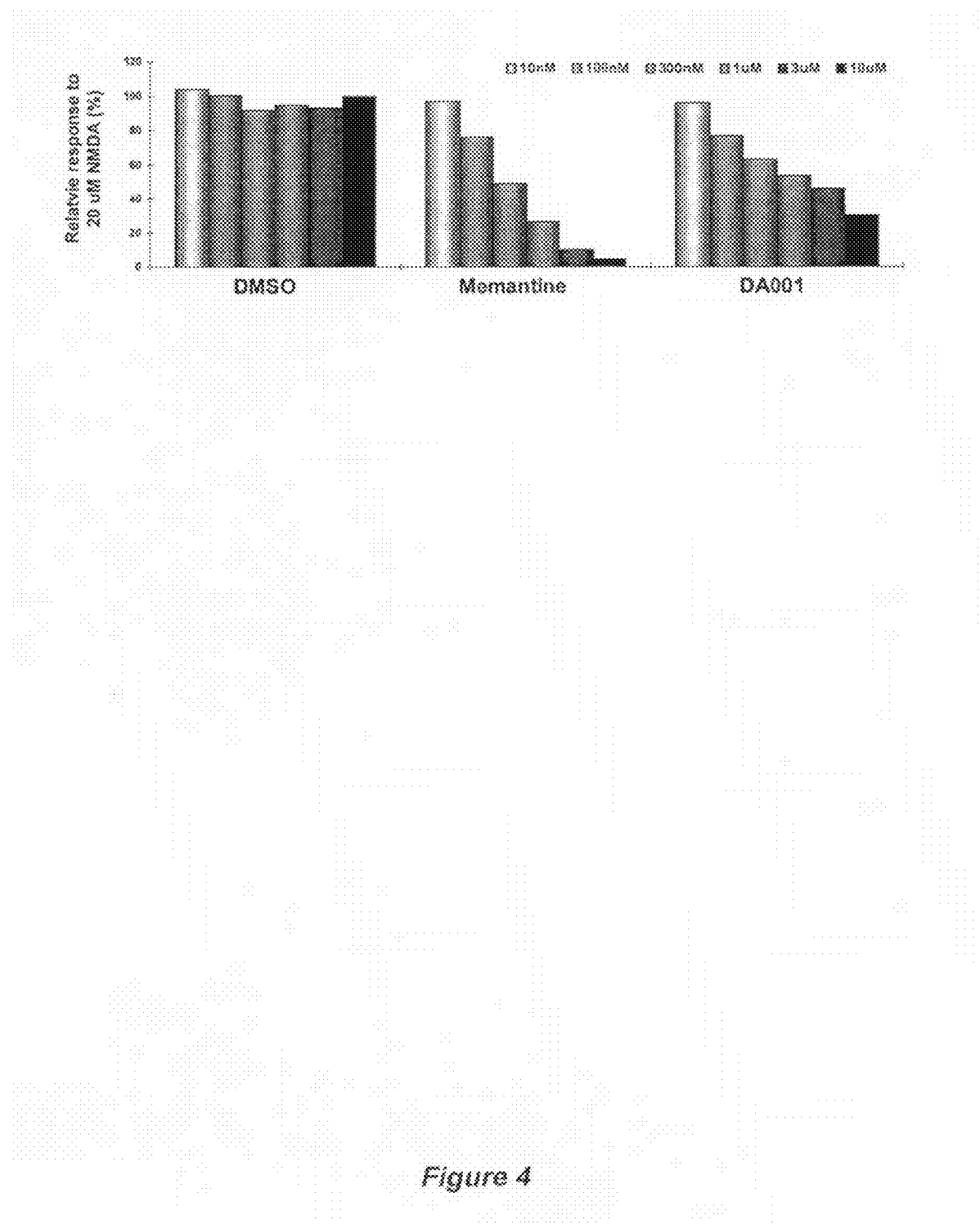
FIG. 4. Embryonic rat primary cortical neuron cultures 11 days in vitro (11DIV) were treated with 10 μM glycine and 20 μM NMDA. They were then treated with DMSO, Memantine or DA001. DMSO percentage variation was identical to DA001 solvent percentage variation per dose; R2=≤0.97 for all $IC_{50}$ values.

DA001 Induces Dose-Dependent Inhibition of NMDA Receptors in Rat Primary Cortical Neurons As shown in FIG. 4, NMDA receptors in primary rat cortical neurons were treated to NMDA and subjected to various doses of DA001 (ranging from 10 nM to 10 μM). DA001 was found to inhibit Ca$^{2+}$ influx in a dose-dependant manner, with a comparable EC$_{50}$ to the known NMDA antagonist memantine.

Example 41

DA001 Protects Rat Primary Cortical Neurons Against NMDA Excitotoxicity

Figure 5:
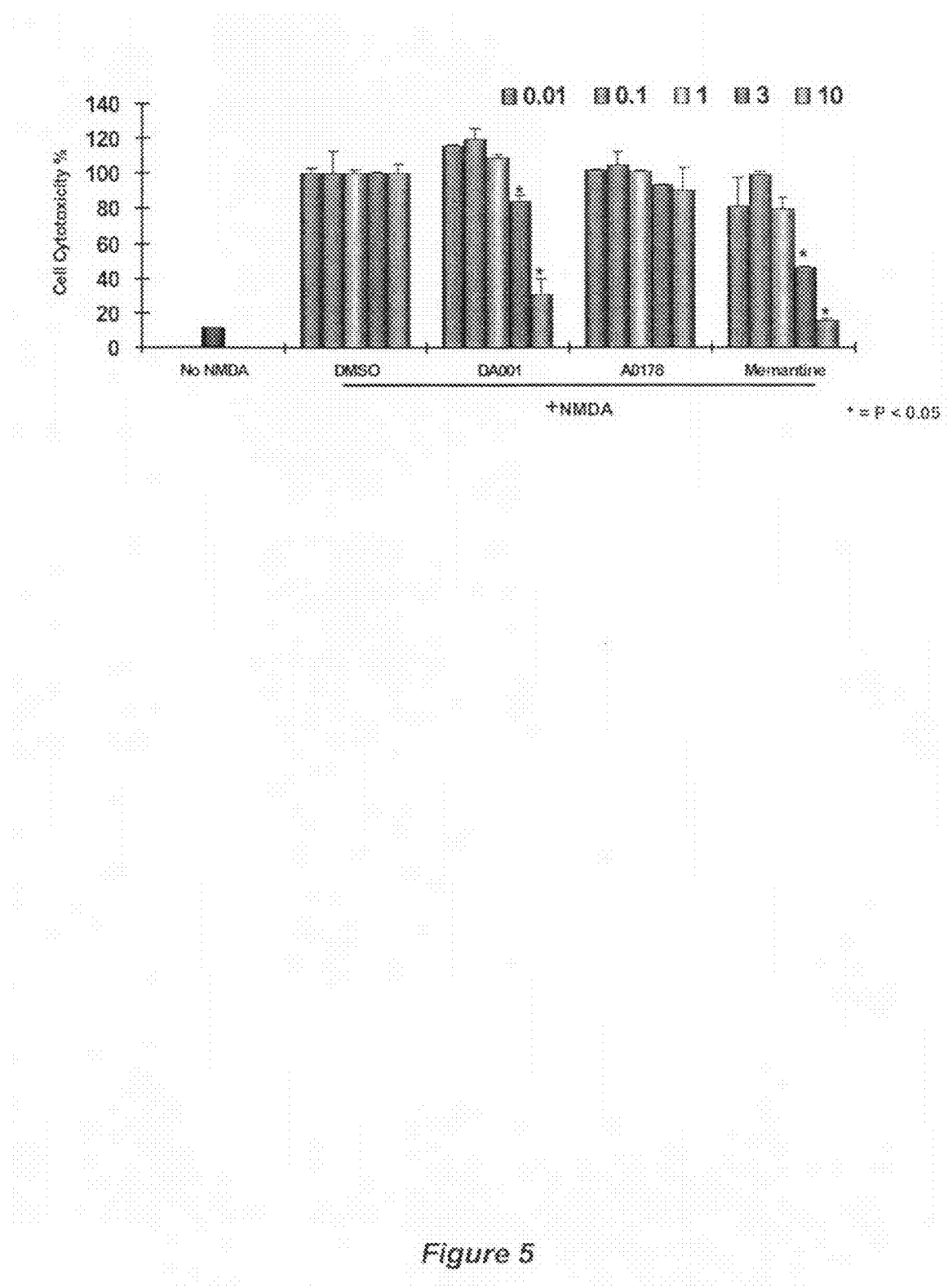
FIG. 5. DA001 protects against NMDA excitotoxicity in rat cortical neurons. Embryonic rat cortical neurons (11 DIV) were treated with NMDA (20 μM) in the absence or presence of TCM samples (μg/ml) or memantine (μM). Memantine is a known NMDA antagonist. LDH release in the medium was measured after overnight incubation and cell cytotoxicity was calculated as a percentage when compared to the solvent control, DMSO.

As shown in FIG. 5, NMDA survival assays were performed to demonstrate the ability of DA001 to prevent NMDA receptor-induced excitotoxicity in primary cortical neuronal cells. FIG. 5 shows the effect of NMDA insults on cortical cells in the absence and presence of differing concentrations of DA001. DA001 (at 10 μg/ml) reduced cell death by more than 60% compared to the DMSO control. Compound A0178 and memantine were included as negative and positive controls, respectively.

Example 42

DA001 Protects Primary Rat Hippocampal Neurons from NMDA Excitotoxicity

Figure 6:
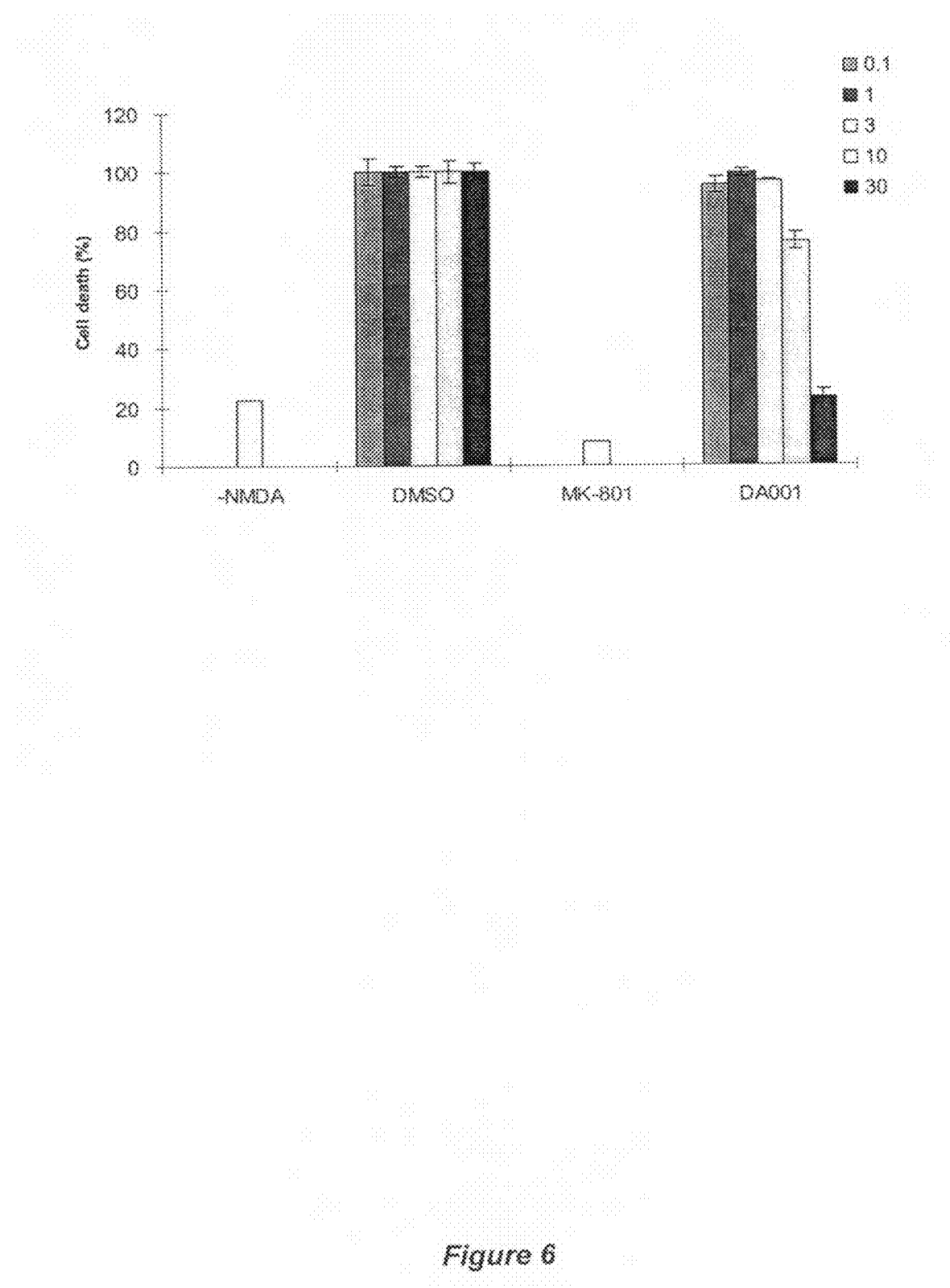
FIG. 6. DA001 protects against NMDA excitotoxicity in rat primary hippocampal neurons. Embryonic rat hippocampal neurons (11DIV) were treated with NMDA (20 μM) in the absence or presence of DA001 (μM) or memantine (μM). LDH release in the medium was measured after overnight incubation and cell cytotoxicity was calculated in percentage when compared to solvent control (DMSO).

NMDA survival assays were performed to demonstrate the ability of DA001 to prevent NMDA receptor-induced excitotoxicity on primary hippocampal neurons. FIG. 6 shows the effect of NMDA insults on hippocampal cells in the presence and absence of DA001. DA001 (at 30 μM) reduced cell death by ~80%.

Example 43

DA001 Prevents NMDA-Induced Excitotoxicity in Rat Primary Cortical Neurons

Figure 7:
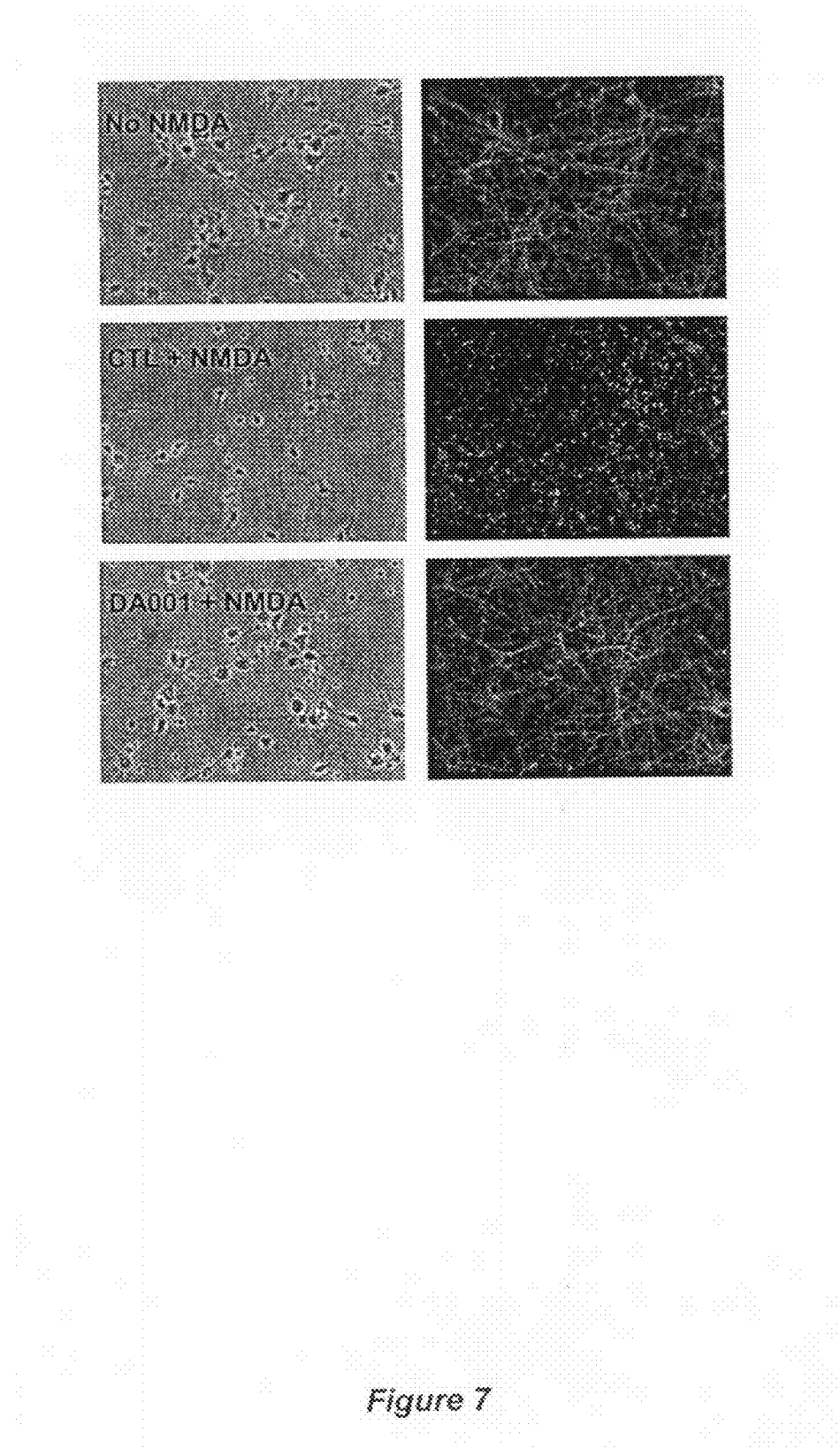
FIG. 7. DA001 protects embryonic rat primary cortical neurons against NMDA excitotoxicity. Neurites were immunostained by beta-tubulin type III antibody and detected with FITC-conjugated antibody. Cell bodies were highlighted with DAPI stain. DMSO was used as the solvent control (CTL).

The ability of compound DA001 to protect against NMDA insults was visually presented through immunostaining experiments. Primary rat cortical neurons subjected to NMDA insults were observed in the presence of DA001 or solvent control DMSO (CTL) as seen in FIG. 7. NMDA insults clearly led to cell death while the addition of compound DA001 (10 μg/ml) protected the cells from excitotoxicity and resulting apoptosis at a level similar to control cells (no NMDA).

Example 44

DA001 Does not Show Cytotoxic Effect on Primary Neurons

Figure 8:
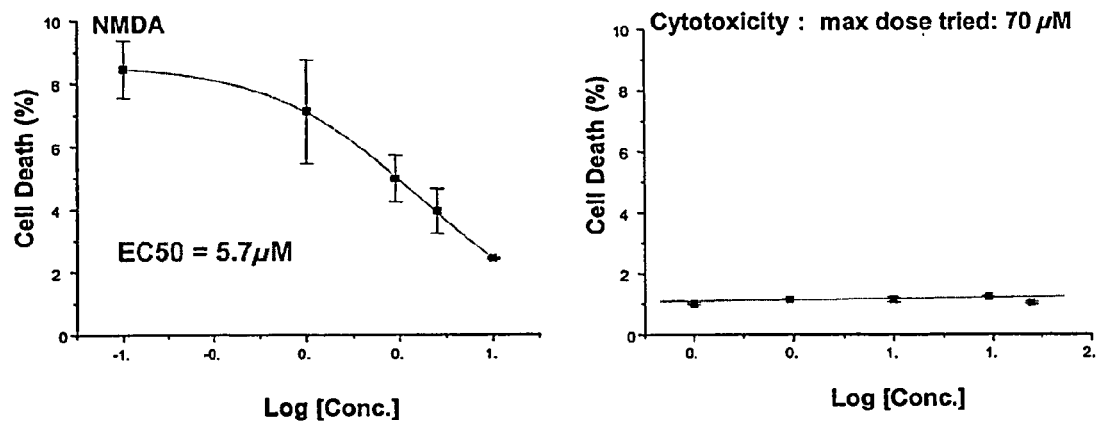
FIG. 8. DA001 does not show any cytotoxic effect on primary neurons. Primary cortical neurons were treated with different concentrations of DA001 for 24 hours. No obvious cell death was observed at all doses examined.

The neuroprotective effects of DA001 were found to be primarily towards NMDA insults. As indicated in FIG. 8, the effect of DA001 on primary cortical neurons was investigated after 24-hour incubation. Importantly, DA001 itself, did not induce cytotoxicity and cell death at all concentrations examined.

Example 45

DA001 Induced CREB Phosphorylation in Rat Primary Cortical Neurons

Figure 9:
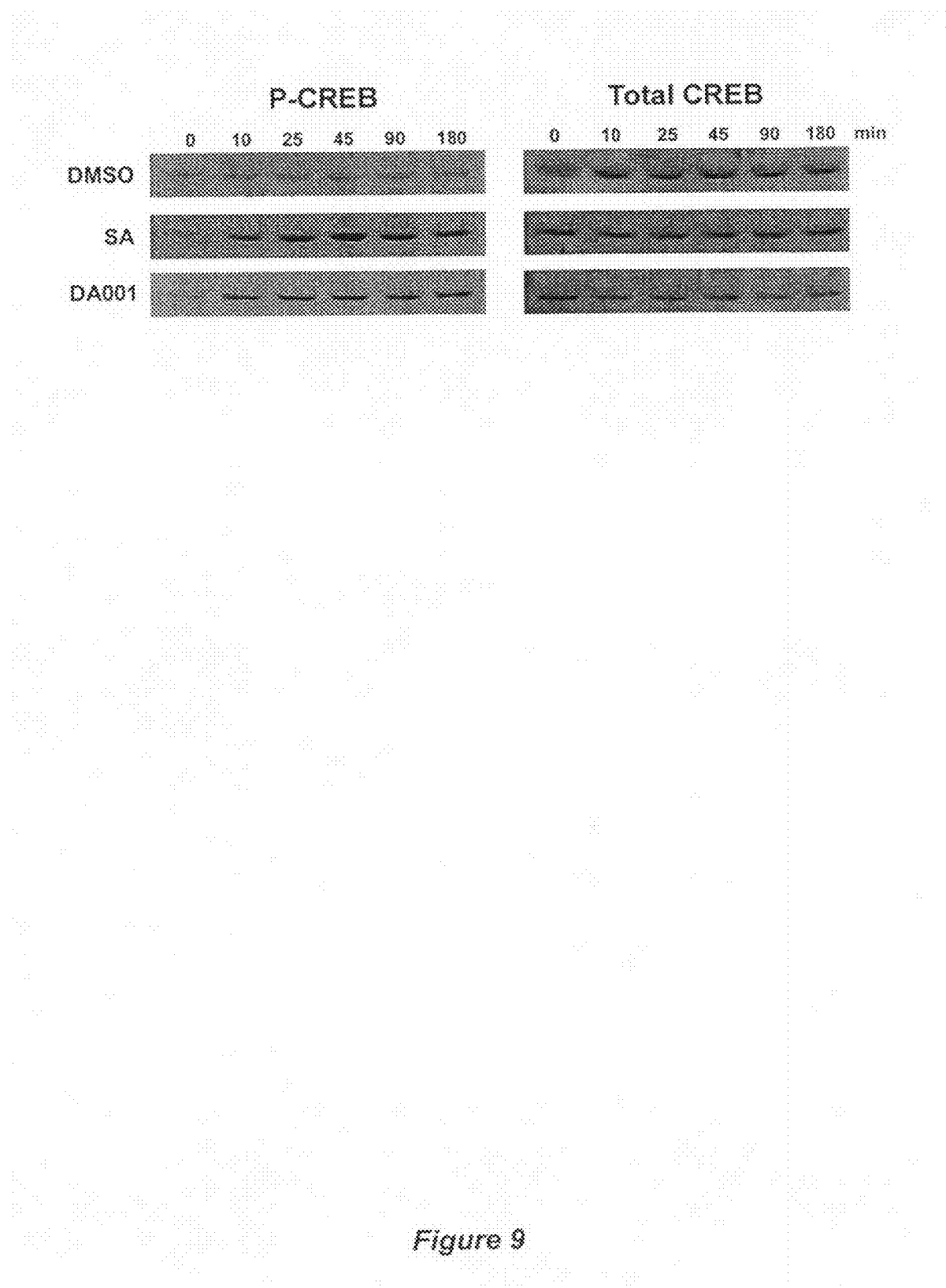
FIG. 9. Long-lasting CREB phosphorylation is induced by DA001. Synaptic activity (SA) was stimulated by addition of bicuculine (50 μM), 4-AP (200 μM), CNQX (10 μM) and nimodipine (5 μM). Transient CREB phosphorylation was induced by NMDA (50 μM). DA001 (13 μM) and SA induced long lasting CREB phosphorylation.

Recent published work has indicated that synaptic activity (SA) mediated by NMDA receptors results in anti-apoptotic activity and neuroprotection. Furthermore, low concentrations of NMDA have been found to induce long-lasting CREB phosphorylation, whereas high doses of NMDA leads to transient CREB phosphorylation and cell toxicity. Neurons pre-treated with SA prior to a high NMDA dose induce long-lasting CREB phosphorylation. Therefore, the neuroprotective effect of DA001 pre-treatment was investigated, the results of which are presented in FIG. 9.

NMDA-mediated synaptic activity was first triggered through the administration of 4-AP ($K^+$ channel blocker) and bicuculline (GABAA receptor antagonist) in the presence of nimodipine (to block L-type voltage-activated $Ca^{2+}$ channels) and CNQX (non-NMDA ionotropic receptor antagonist). This was followed by treatment with a high dose of NMDA (50 μM). Pre-treatment of the cortical neurons with DA001 resulted in long-lasting CREB phosphorylation at a similar level to SA.

Example 46

DA001 Protects Against NMDA Insults Comparatively with Memantine

Figure 10:
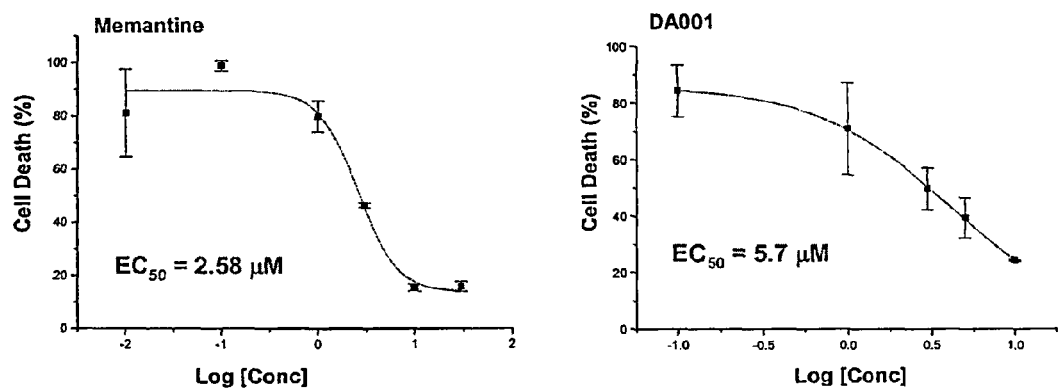
FIG. 10. Comparative dose curves and corresponding $EC_{50}$s for DA001 and Memantine.

As shown in FIG. 10, DA001 exhibits NMDA receptor antagonist activity to protect cells against neurotoxicity. This activity against NMDA-induced insults is comparable to memantine. Memantine is an FDA-approved NMDA antagonist used for clinical indications such as dementia in Alzheimer's disease. Dose-dependant assays were performed for each compound and based on the resulting dose response curve, the corresponding $EC_{50}$ for each compound was determined.

Example 47

Novel Compounds Enhance Learning and Memory in In Vivo Studies

Figure 11A:
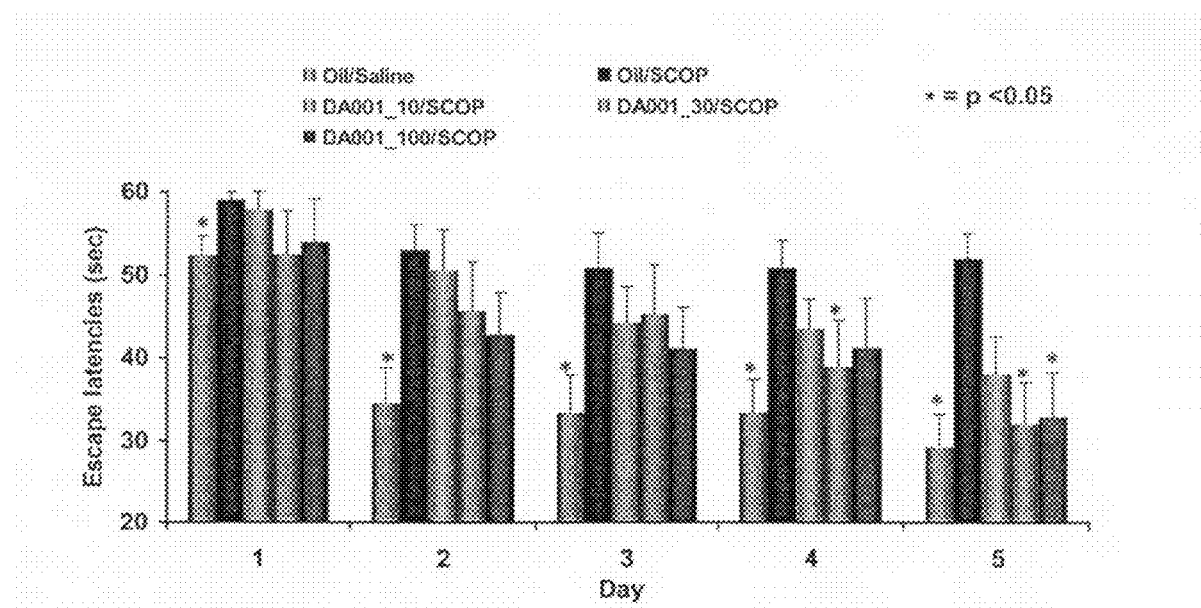
FIG. 11A. DA001 reduces the escape latency in Morris Water Maze model. Scopolamine (SCOP; 4 mg/kg) was first administered intra-peritoneally to mice to impair their memories. Scopolamine-induced memory impaired mice were then orally administered one of three different doses of DA001 (10, 30, or 100 mg/kg) and subjected to the Morris water maze over a period of 5 days. On each day, the time taken for the mice to detect the hidden platform in the water maze was measured, in seconds. Measurements were calculated as the mean latency periods for each mouse, n=12 per group. Data are expressed as mean±s.e.m. and compared to Oil/SCOP group. Doses are represented in mg/kg.
Figure 11B:
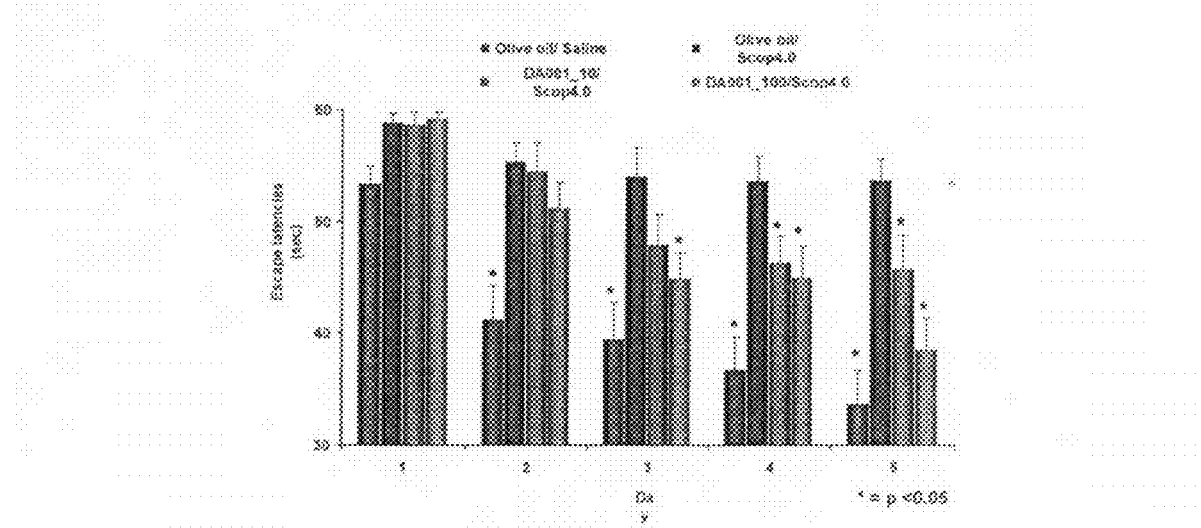
FIG. 11B. DA001 reduces the escape latency in Morris Water Maze model. Scopolamine (SCOP; 4 mg/kg) was first administered intra-peritoneally to mice to impair their memories. Scopolamine-induced memory impaired mice were then orally administered DA001 (10 and 100 mg/kg) and subjected to the Morris water maze over a period of 5 days. On each day, the time taken for the mice to detect the hidden platform in the water maze was measured, in seconds. Measurements were calculated as the mean latency periods for each mouse; n=24. Data are expressed as mean+s.e.m. and compared to Oil/SCOP group. Doses are represented in mg/kg.

As shown in FIG. 11, the therapeutic effect of the novel compounds on spatial learning and memory in mice was demonstrated using Morris water maze task, the favoured test to study hippocampal-dependant learning and memory. The Morris water maze consists of a water pool with a hidden, submerged escape platform. The mice must learn, over a period of consecutive days, the location of the platform using either contextual or local cues. The time taken to locate the hidden platform (escape latency) is a measure of the animal's cognitive abilities.

For the compound DA001, the test subjects in the control group (oil/saline) took ~30 seconds to detect the platform after 5 days of training. In contrast, the scopolamine-induced memory-impaired group required almost twice the amount of time to locate the platform after an identical training period. DA001 reversed the increased escape latency induced by scopolamine at all three test concentrations.

Example 48

Figure 12:
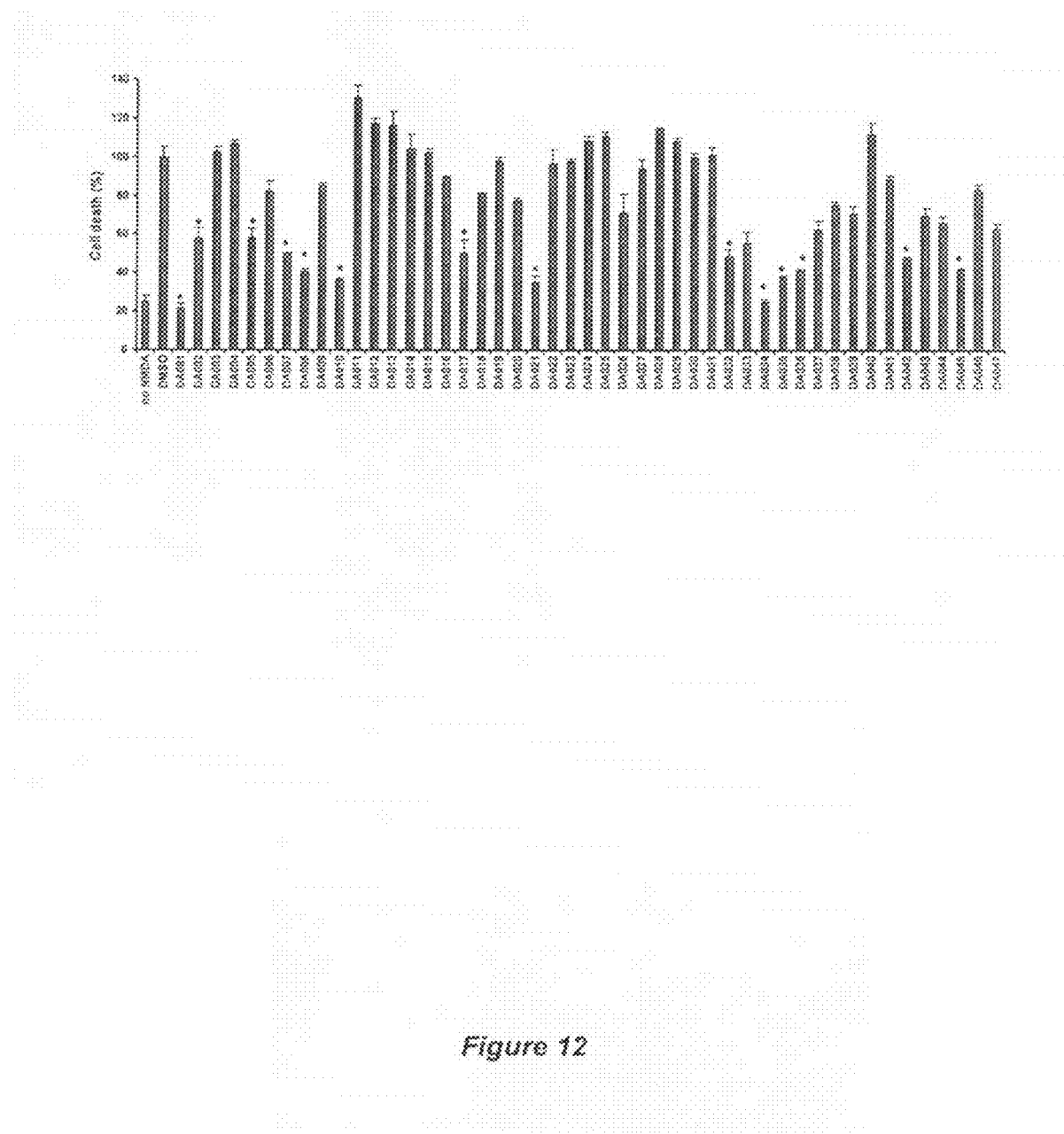
FIG. 12. Derivatives of DA001 rescue the cortical neurons from NMDA excitotoxicity. Embryonic rat cortical neurons (11DIV) were treated with NMDA (20 μM) in the absence or presence of DA001 or its derivatives (10 or 30 μM); LDH release in the medium after overnight or 24 hours incubation was measured and cell death was calculated as a percentage in comparison to DMSO, the solvent control. Data are expressed as mean+s.e.m. *=P<0.05.

Novel DA001 Derivatives Protect Rat Primary Cortical Neurons Against NMDA Excitotoxicity NMDA survival assays were performed to demonstrate the ability of novel compounds derived from DA001 to prevent NMDA receptor-induced excitotoxicity. NMDA survival assays were performed to measure the degree of protection provided to cortical neuronal cells when treated with the novel compounds (at 30 μM except DA026 at 10 μM) prior to NMDA insult. As seen in FIG. 12, treatment with a number of derivatives reduced cell death to levels comparable to that without NMDA treatment. Amongst the derivatives, DA021, a compound with novel structure, showed promising protective effect on cortical neurons against NMDA insults.

Example 49

Figure 13:
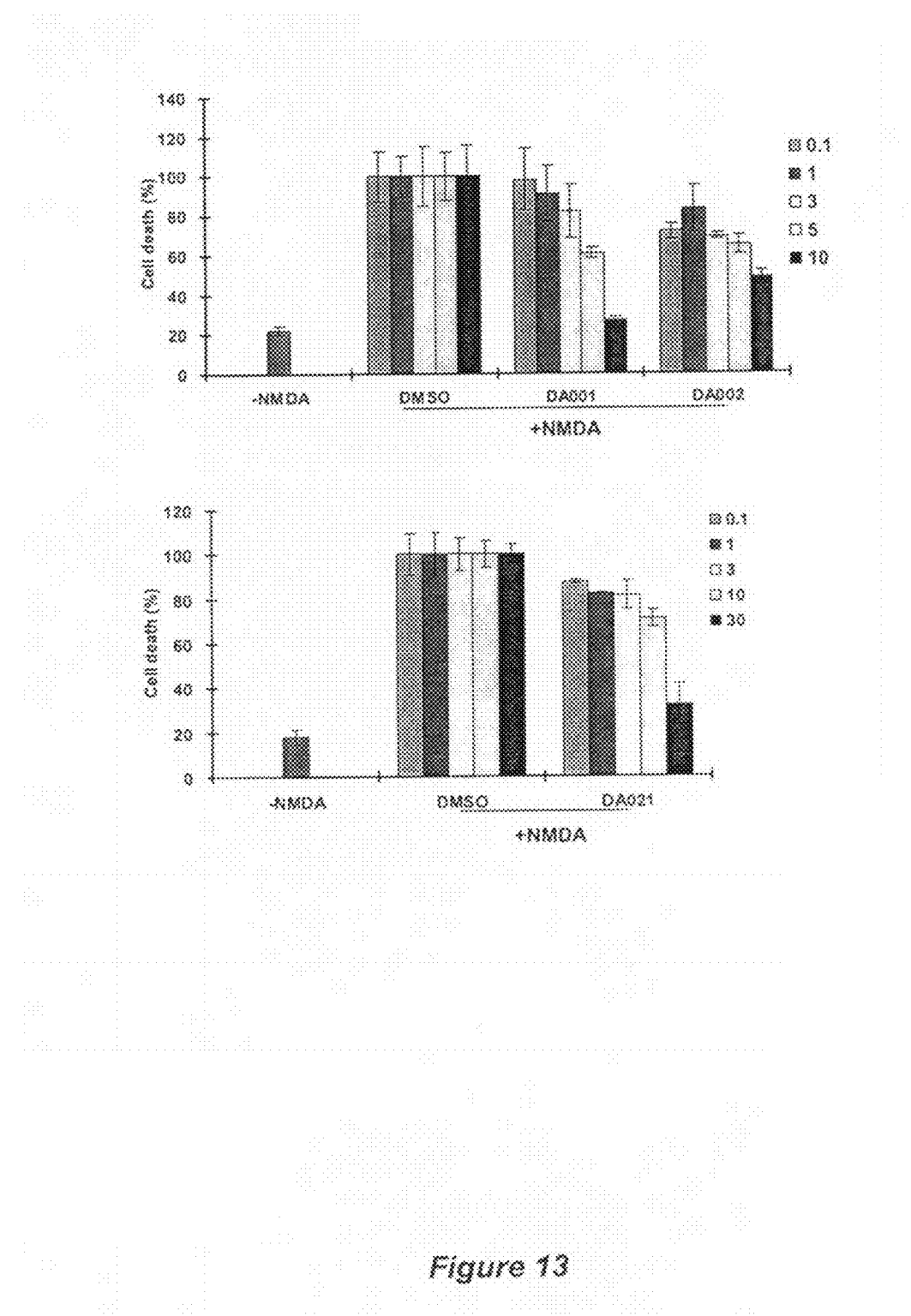
FIG. 13. DA002 and DA021, both derivatives of DA001, reduced NMDA-induced excitotoxicity. Embryonic rat cortical neurons (11DIV) were treated with NMDA (20 μM) in the absence or presence of DA002 or DA021 (μg/ml). LDH release in the medium after overnight incubation was measured and cell cytotoxicity was calculated as a percentage in comparison to DMSO, the solvent control.

The Novel Derivative Compound DA021 Protects Rat Primary Cortical Neurons Against NMDA Excitotoxicity Compounds derived from DA001 were tested for their ability to inhibit NMDA-induced excitotoxicity. Primary rat cortical neurons were subjected to NMDA insults in the presence and absence of the novel derivatives. As shown in FIG. 13, both DA002 and DA021 reduced cell death prominently compared to DA001.

Example 50

DA001 Regulates Spine Morphogenesis in Hippocampal Neurons

Figure 14:
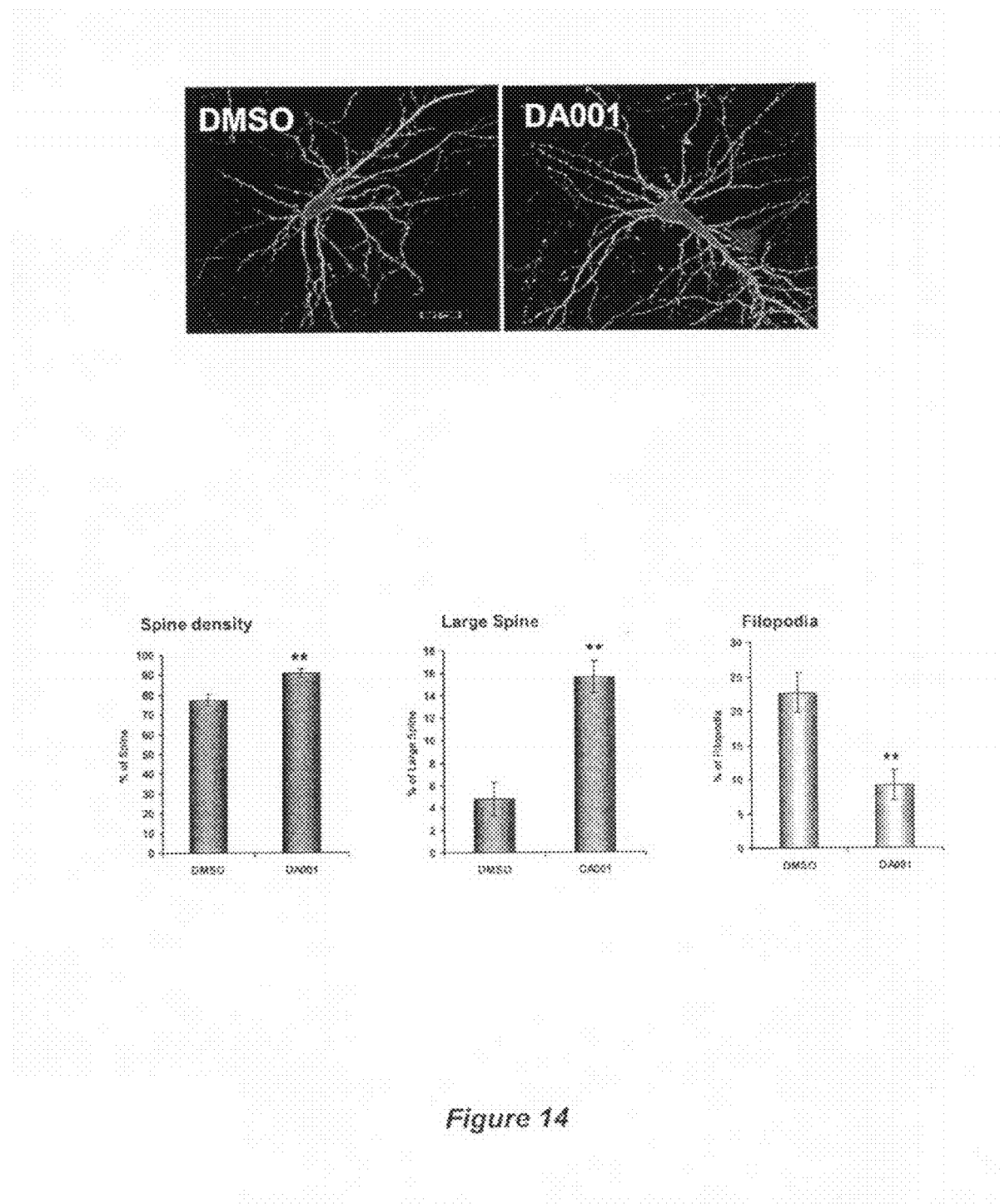
FIG. 14 shows that DA001 regulates spine morphogenesis in hippocampal neurons. DA001 significantly increases spine density and large spine (head>1 um) numbers while the numbers of filopodia are significantly reduced, compared to the control (DMSO). N=20, symbol ** indicates P<0.005.

As shown in FIG. 14, hippocampal neurons were transfected with EGFP (green fluorescent protein) construct at 7 DIV using calcium phosphate precipitation. The GFP-expressing neurons, at 14 DIV, were then treated with 30 μM DA001 or vehicle control (DMSO) for 24 hr. The dendritic spine morphology of hippocampal neurons was examined under confocal microscope. DA001 significantly increased spine density and large spine (head>1 um) numbers while the numbers of filopodia were significantly reduced, compared to the control (DMSO). N=20, ** indicates P<0.005.

Two classes of spines are identified in hippocampal neurons: mature spines and filopodia (immature spines). When the neuronal cells were subjected to DA001, the DA001-treated neurons exhibited an increase in the percentage of spine density, especially for spine that heads were larger than 1 μm. Furthermore, there was a reduction in the frequency of filopodia compared to the control.

Example 51

DA001 Regulates Axon Development in Cortical Neurons

During early neuronal differentiation, axon and dendrites extend from the neuronal cell body. The axon will target to the dendrites of another neuron to form synapse. The process involved in the proper extensions of axon is important for the formation of neural circuits. To examine the effect of DA001 in this process, freshly isolated neurons were treated with the compound and extensions of axons were examined and quantified. DA001 significantly promotes the length of axons in these cultures.

Figure 15:
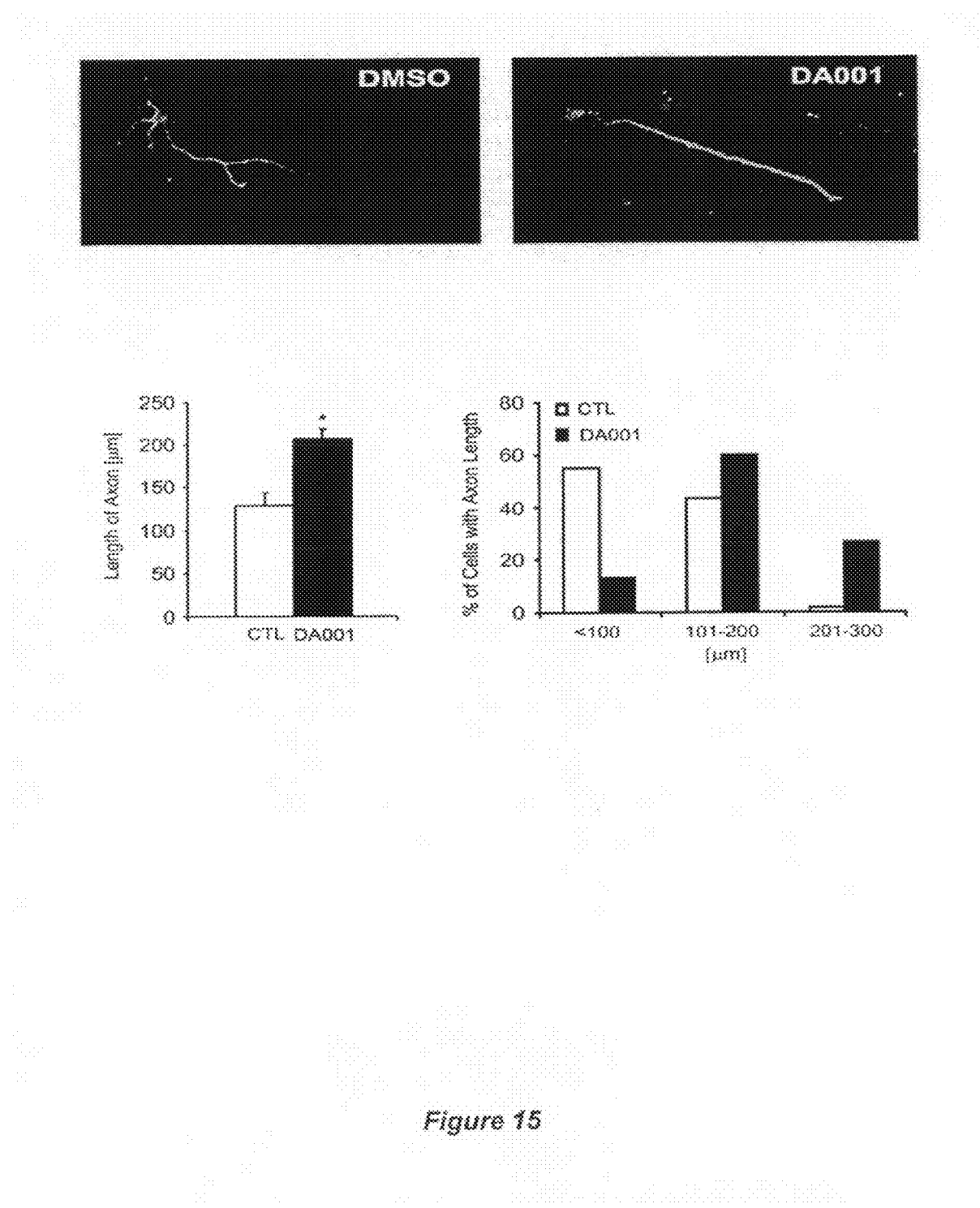
FIG. 15 illustrates that DA001 induces longer axon in cultured cortical neurons.

As shown in FIG. 15, dissociated cortical neurons were treated with solvent control (DMSO) or DA001 (30 μM) at 0 DIV for 2 days. Cells were then fixed and stained with anti-Tau antibodies. Images were taken under Olympus confocal microscope. Length of axons (Tau-positive cells) was calculated and quantified. Scale bar: 50 μm. *=P<0.01.

Example 52

DA001 Protects Neurons Against Differing Concentrations of NMDA

Cortical neurons were pre-treated with DA001 and subsequently subjected to varying concentrations of NMDA. Survival assays were then conducted to determine the ability of DA001 to effectively protect neuronal cells from NMDA-induced excitotoxicity. As indicated in FIG. 16, there was a significant reduction in cell death upon pre-treatment with DA001 compared to the DMSO control at high concentrations of NMDA.

Figure 16:
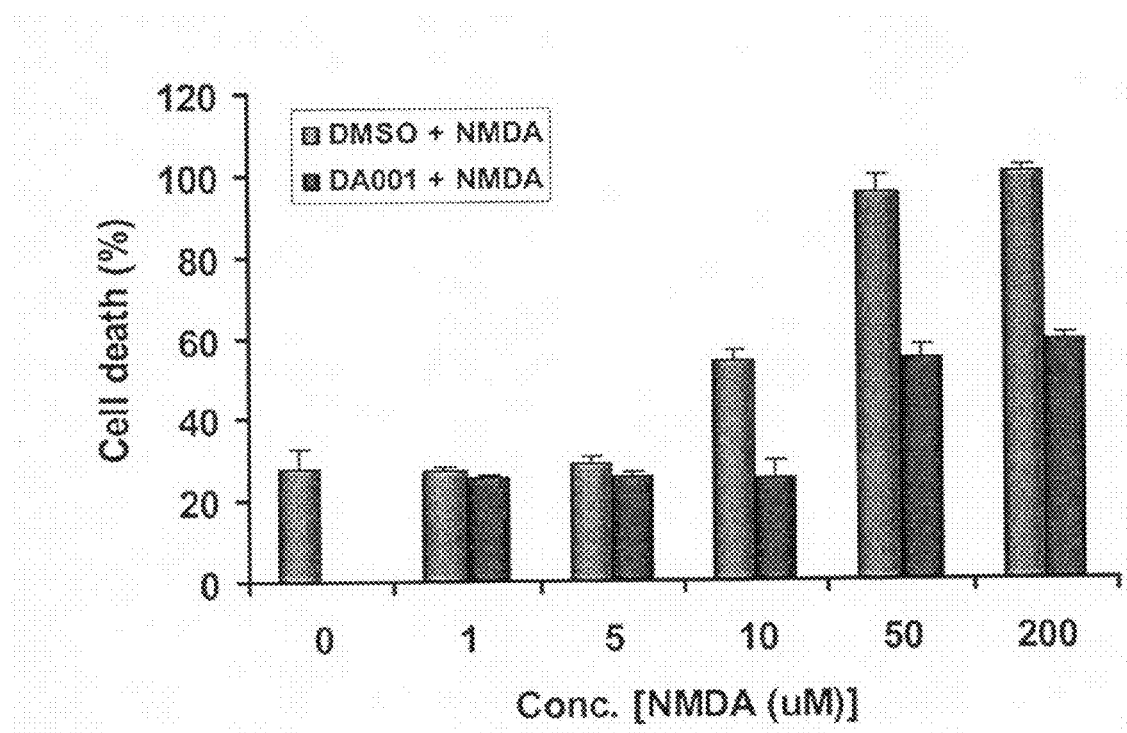
FIG. 16 illustrates that DA001 protects neurons against differing concentrations of NMDA.

As shown in FIG. 16, cortical neurons were incubated with DA001 (30 μM) or control (DMSO) for 24 hrs, followed by treatment with different concentrations of NMDA (1-200 μM) for 20 min. LDH release into the medium was then measured.

Example 53

DA001 Protects Neurons Against Glutamate Insults

Glutamate is the neurotransmitter which activates NMDA receptors. Cortical neurons were pre-treated with DA001 and subsequently subjected to varying concentrations of glutamate (5-200 μM). Survival assays were then conducted to determine the ability of DA001 to effectively protect neuronal cells from excitotoxicity. As indicated in FIG. 17, there was a significant reduction in cell death upon pre-treatment with DA001 compared to the DMSO control at high concentrations of glutamate.

Figure 17:
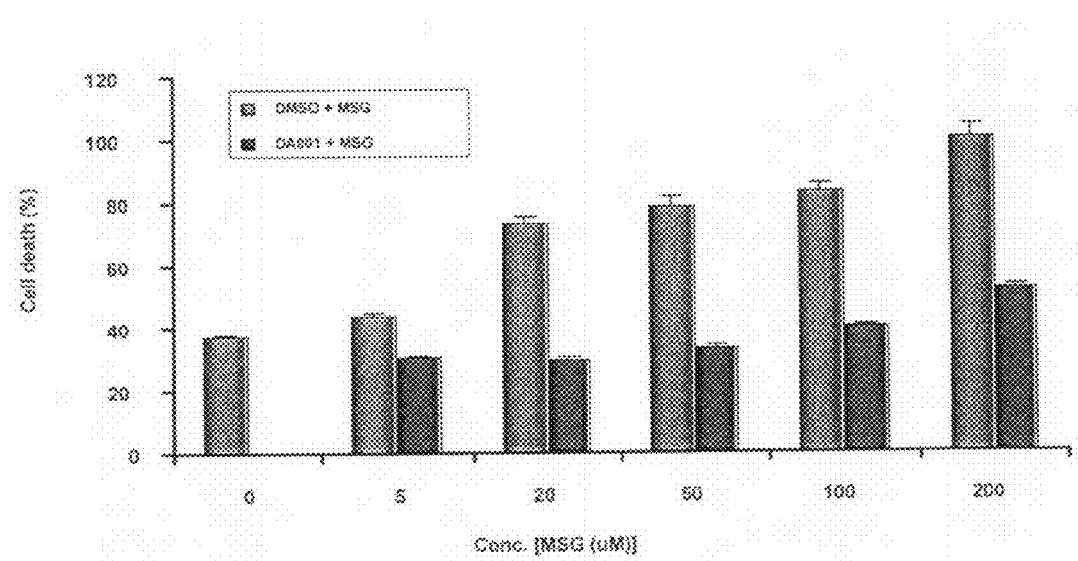
FIG. 17 illustrates that DA001 protects neurons against glutamate insults.

As shown in FIG. 17, cortical neurons were incubated with DA001 (30 μM) or control (DMSO) for 24 hrs, followed by treatment with different concentrations of glutamate (5-200 μM) for 20 min. LDH release into the medium was then measured.

Example 54

DA001 Decreases the Infarct Size and Edema of Ischemic Brain

The MCAO (middle carotid artery occlusion model) was performed to investigate the protective effects of DA001 on the brain when the brain was exposed to transient focal ischemia (or lack of oxygen) such as during a stroke. Hemispheric brain swelling and infarct volume (the area of dead tissue caused by inadequate blood supply) was measured for test subjects treated with the compound 6 hours after ischemia and compared to that of the control group. DA001 effectively reduced infarct volume (the area of dead tissue caused by inadequate blood supply) and the extent of edema during ischemic conditions.

Figure 18:
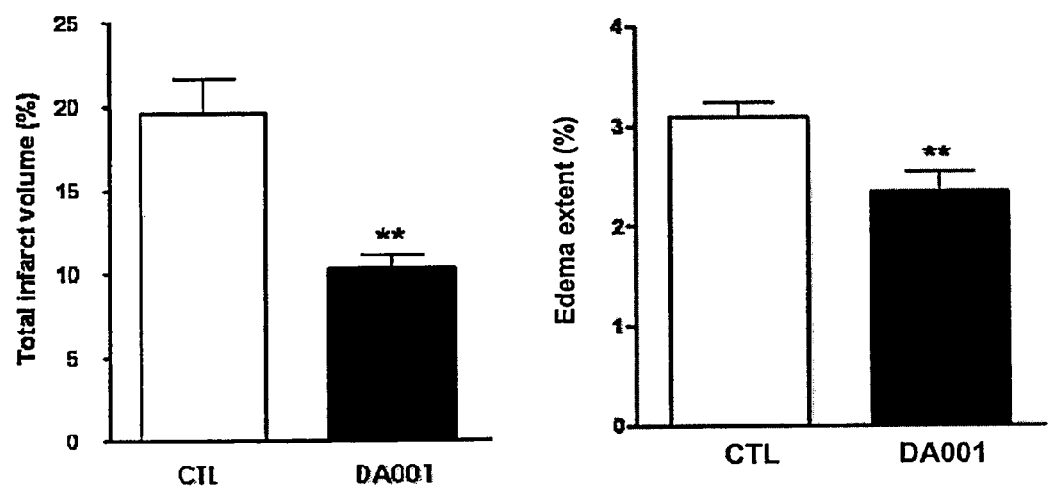
FIG. 18 shows that DA001 decreases the infarct size and edema of ischemic brain. Values are mean±S.E.M, n=8, DA001; n=7, control (CTL); and symbol ** indicates P<0.01 vs the control group.

As shown in FIG. 18, DA001 (12.6 mg/kg and 42 mg/kg) administered 6 h post-ischemia P.O. could significantly decrease the total infarction MCAO rats and the extent of edema respectively.

Example 55

DA001 Induces BDNF Expression Following NMDA Treatment

Cortical neurons were pre-treated with DA001 prior to being subjected to NMDA insults, after which total RNA was extracted at different time intervals after treatment. There was a 5-fold increase in BDNF expression after a 6 hour incubation period. BDNF expression remained ~3-4 fold over the control (DMSO) 12-24 hours after treatment with DA001.

Figure 19:
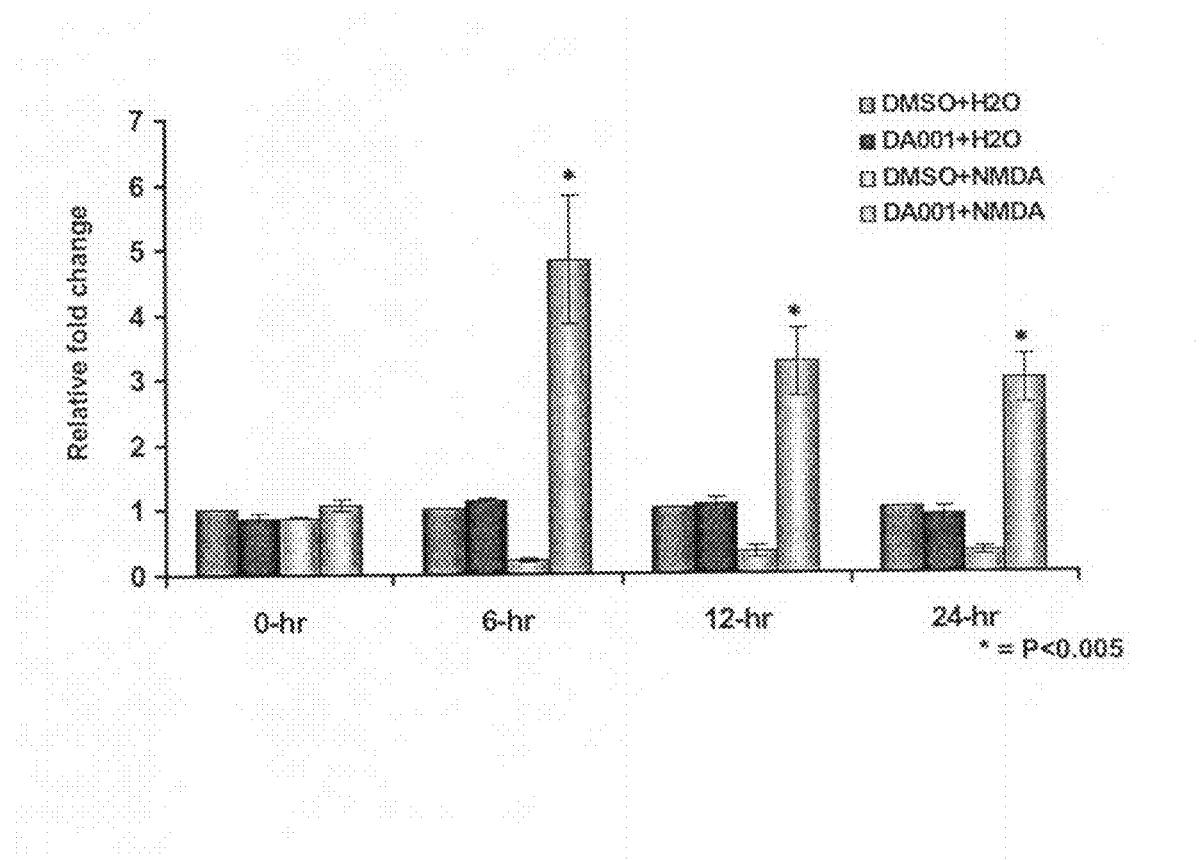
FIG. 19 shows that DA001 induces BDNF expression following NMDA treatment.

As shown in FIG. 19, cortical neurons were incubated with DA001 or DMSO for 24 hrs, followed by treatment with NMDA (20 μM) or water for 20 min. Total RNA was extracted followed by cDNA synthesis. Gene expression was normalized against home gene, hypoxanthine phosphoribosyltransferase 1 (HPRT1) and glyceraldehyde 3-phosphate dehydrogenase (GAPDH). Relative change in gene expression induced by DA001+$H_2O$ and DA001+NMDA was compared with the controls, DMSO+$H_2O$ and DMSO+NMDA, respectively.

Example 56

DA001 Induces BDNF and NT-3 Expression but not Bcl-2 or c-fos Following NMDA Treatment Cortical neurons were pre-treated with DA001 after which the cells were subjected to NMDA insult. The expression of BDNF was measured at three different time intervals and compared to that of NT-3, Bcl-2 and c-fos. DA001 induced BDNF and NT-3 expression but not bcl-2 or c-fos under the same conditions.

Figure 20:
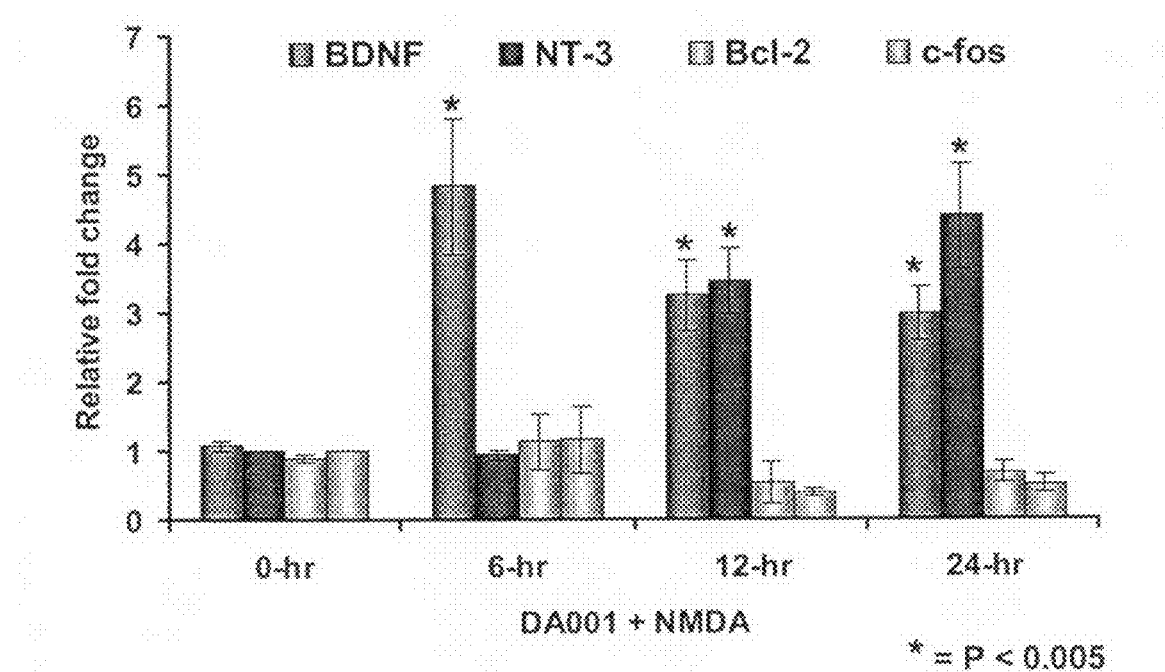
FIG. 20 illustrates that DA001 induces BDNF and NT-3 expression but not Bcl-2 or c-fos following NMDA treatment.

As shown in FIG. 20, cortical neurons were incubated with DA001 or the DMSO control for 24 hrs, followed by treatment with NMDA (20 uM) or water for 20 min. Gene expression was normalized against home gene, hypoxanthine phosphoribosyltransferase 1 (HPRT1) and glyceraldehyde 3-phosphate dehydrogenase (GAPDH) and compared to the control (DMSO) with NMDA treatment. Relative change in gene expression induced by DA001+NMDA was compared with DMSO+NMDA.

Example 57

DA001 Inhibits Melanocortin Binding to MC1 and MC4 Receptors

DA001 was evaluated against 109 receptor binding assays and 17 enzyme assays, comprising of selective, central and peripheral therapeutically-relevant targets. Radioligand competition assays were conducted whereby DA001 was tested at one concentration (10 µM) in duplicate. DA001 significantly inhibits melanocortin binding to melanocortin-1 (MC1) and melanocortin-4 (MC4) receptors (based on the manufacturer's guidelines for a cutoff at 50% inhibition). It could compete with the radioligand [$^{125}$I-NDP-alpha-melanocyte-stimulating hormone (α-MSH)] binding for MC1 and MC4 but not MC3 and MC5 nor the related family, the melanin concentrating hormone receptors (MCH1 and MCH2). Moderate to mild inhibition of DA001 was also observed for kainate, melatonin ($MT_1$) and serotonin ($5\text{-}HT_{1D}$ subtype) receptors.

TABLE 2

| Binding assay | % inhibition of control specific binding | Target |
| --- | --- | --- |
| MC1 | 64 | Melanocortin |
| MC3 | 12 | Melanocortin |
| MC4 | 59 | Melanocortin |
| MC5 | 11 | Melanocortin |
| MCH1 | −9 | Melanin concentrating hormone |
| MCH2 | −12 | Melanin concentrating hormone |
| Kainate | 35 | Kainate |
| MT1 | 28 | Melatonin |
| 5-HT1D | 30 | Serotonin |

To determine the $IC_{50}$ for DA001 to inhibit α-MSH binding on MC1 and MC4 receptor, the compound was further characterized by a dose-dependent study. DA001 was evaluated with 8 concentrations on MC1 and MC4 receptor binding assays. DA001 showed an $IC_{50}$ of 10 µM and 6.8 µM, for MC1 and MC4, respectively.

TABLE 3

|  | $IC_{50}$ (M) | $K_i$ (M) | $n_H$ |
| --- | --- | --- | --- |
| MC1 | 1.00E−05 | 5.20E−06 | 0.9 |
| MC4 | 6.80E−06 | 6.30E−06 | 1.3 |

Figure 21:
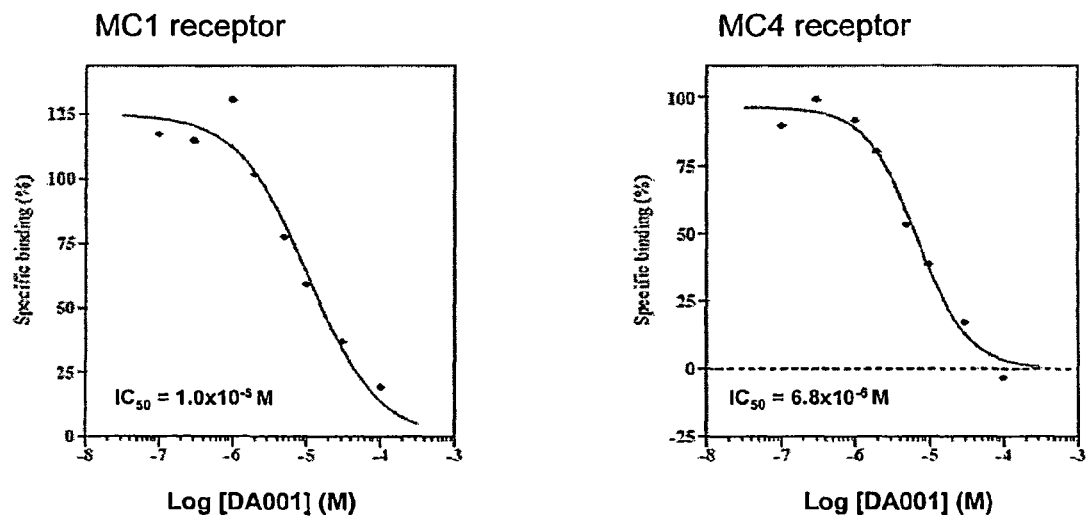
FIG. 21 shows that DA001 inhibits melanocortin binding to MC1 and MC4 receptors. Competition curve is obtained with DA001 at the human MC1 or MC4 receptor.

FIG. 21 shows the competition curves obtained with DA001 at the human MC1 or MC4 receptor. The specific ligand binding to the receptors is defined as the difference between the total binding and the nonspecific binding determined in the presence of an excess of unlabelled ligand. The results are expressed as a percent of control specific binding [(measured specific binding/control specific binding)×100] and as a percent inhibition of control specific binding {100−[(measured specific binding/control specific binding)×100]} obtained in the presence of DA001. The $IC_{50}$ values (concentration causing a half-maximal inhibition of control specific binding) and Hill coefficients (nH) were determined by non-linear regression analysis of the competition curves generated with mean replicate values using Hill equation curve fitting ($Y=D+[(A-D)/(1+(C/C50)nH)]$, where Y=specific binding, D=minimum specific binding, A=maximum specific binding, C=compound concentration, C50=$IC_{50}$, and nH=slope factor). This analysis was performed using a software developed at Cerep (Hill software) and validated by comparison with data generated by the commercial software SigmaPlot® 4.0 for Windows® (© 1997 by SPSS Inc.).

Example 58

DA001 Antagonizes MC4 Receptor

To determine whether the inhibitory effect of DA001 on the ligand binding to MC4 receptors results from agonism or antagonism, DA001 was evaluated at one concentration on these specific binding assays. DA001 showed a 25% inhibition on cyclic AMP induction in the presence of α-MSH, while DA001 alone cannot elicit cAMP increase on MC4 receptor.

TABLE 4

| MC4 receptor | cAMP measurement |
| --- | --- |
| Agonist effect | −1 |
| Antagonist effect | 25 |

As shown in Table 4, DA001 shows a moderate antagonist effect on MC4 receptor. DA001 (10 µM) was subjected to ligand binding assay with human MC4 receptor overexpressing cells. Results are expressed as a percent of control specific agonist response [100−(measured specific response/control specific agonist response)×100] obtained in the presence of DA001.

Example 59

Study the Effect of DA001 as an Anti-Depressant

To examine the effectiveness of DA001 to act as an anti-depressant, the effect of DA001 was evaluated using the forced swim test (FST) and compared to the anti-depresseant, imipramine. DA001 significantly reduces the immobility time of mice in the FST when compared to vehicle control.

Figure 22:
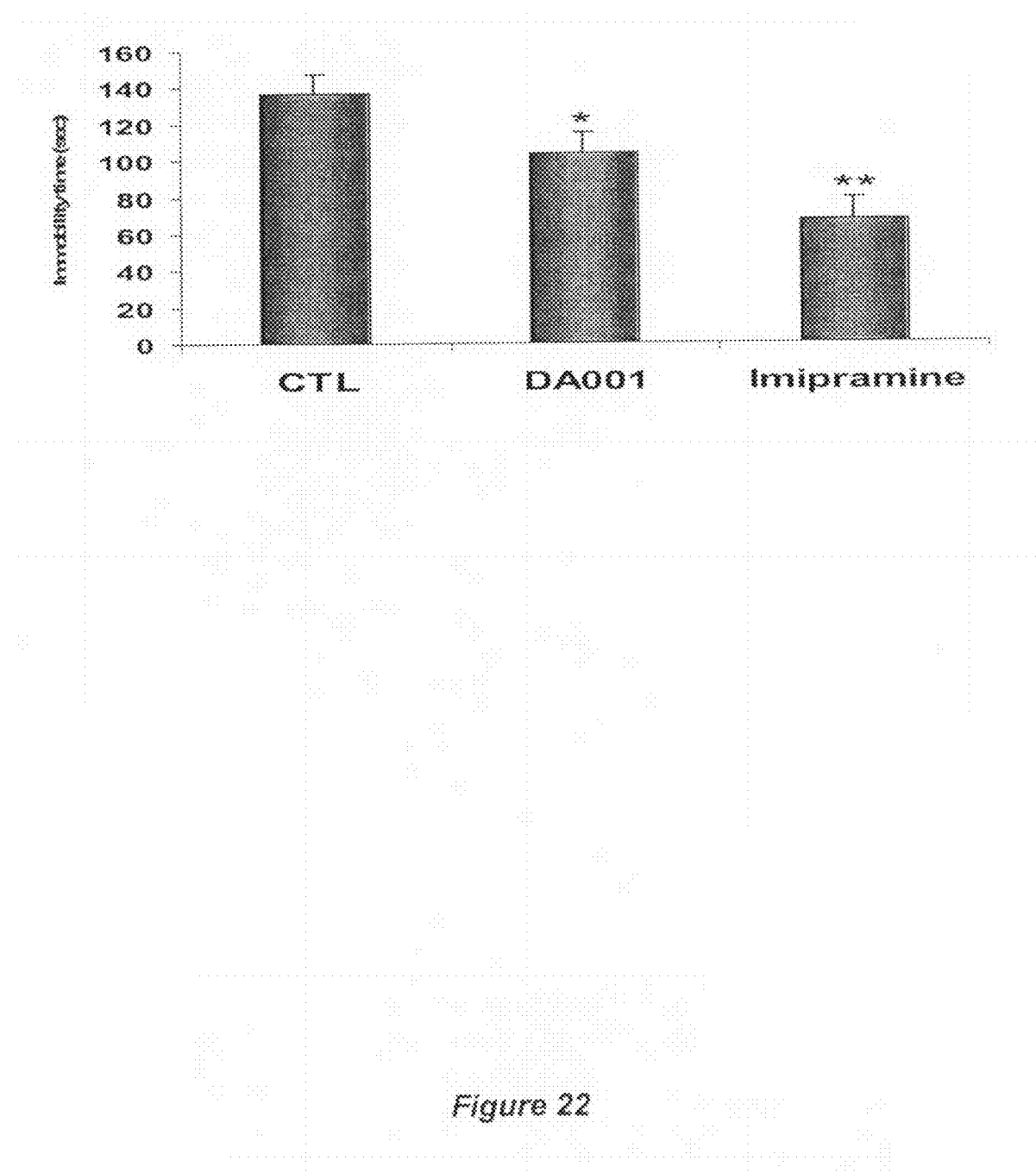
FIG. 22 illustrates the effect of DA001 on the duration of immobility time for mice in forced swim test. Data are expressed as mean+s.e.m, n=30. Symbol * denotes P<0.05, and symbol ** denotes P<0.005.

As shown in FIG. 22, DA001 (100 mg/kg) was administered orally to mice prior to the swimming session. Solvent (CTL) and imipramine (15 mg/kg) were used as negative and positive controls, respectively. Measurements were calculated as the mean of duration of immobility time (sec).

Example 60

Assays, Detections and Tests

Whole-Cell Patch Clamp

Hippocampal neurons were prepared from embryonic day 18 Sprague-Dawley rats. After the hippocampus had been removed from the brain, isolated cells were plated onto Poly d-Lysine (PDL) (P0899, Sigma)-coated 35 mm dishes (153066, NUNC) at a density of $3\times10^5$ cell per plate using Neurobasal Medium (NB) (21103-049, Gibco) with B27 supplement (17504-044, Gibco), penicillin/streptomycin (15140, Gibco) and 1 mM L-glutamine (25030, Gibco). The cell culture was incubated at 37° C. in a humidified atmosphere of 5% $CO_2$ in air. Half of the medium was changed with NB, B27 and 50 µM L-glutamine every 2 to 3 days. On day 12 in vitro (12DIV), whole-cell patch clamp was performed. The internal solution contained 120 mM cesium chloride, 20 mM tetraethylammonium chloride, 2 mM magnesium chloride, 1 mM calcium chloride and 10 mM HEPES (pH 7.2). The external solution contained 137 mM sodium chloride, 1 mM sodium bicarbonate, 0.34 mM sodium phosphate dibasic, 5.37 mM potassium chloride, 0.44 mM potassium phosphate monobasic, 2.5 mM HEPES (pH 7.4) and 22.2 mM glucose. Samples mixed with 50 µM NMDA (M3262, Sigma) were arranged in linear array of up to 8 individual controlled pipes (List Medical, Germany) which were connected to solution reservoirs. Memantine (10 µM, M9292, Sigma) was used as a positive control. Pipettes were fire-polished to produce a pipette resistance of 3-5 MΩ Holding potential of patched cells was kept at −80 mV and currents were recorded using Axopatch-200B amplifier (Axon Instruments, USA). Tetrodotoxin (5 µM) and bicuculline methiodide (20 µM) (0109, Tocris) were present in the bath solution to block synaptic transmission mediated by voltage-gated sodium channels and $Ca^{2+}$-activated potassium channels, respectively. Data was analyzed by pClamp9 software and percentage of inhibition on NMDA-induced current was represented in comparison to solvent control.

Neuronal Cultures and Neuron Survival Assay Against NMDA Insult

Primary cortical and hippocampal neurons were prepared from embryonic day 18 (E18) Sprague-Dawley rats. Neurons were plated on 24-well plate (TPP, Corning) at a density of $2\times10^5$ cells per well using Neurobasal medium (Invitrogen) supplemented with 2% B27 (Invitrogen). Neurons at 11-12 days in vitro (12DIV) were subjected to drug treatment. Neurons were pretreated with the test compound for 2 hours prior to NMDA treatment. 0.1 µM (+)-MK-801 Hydrogen Maleate (Sigma) was added as a positive control. Briefly, the neurons were rinsed with Locke's solution (5 mM potassium chloride, 128 mM sodium chloride, 2.7 mM calcium chloride, 1 mM di-sodium hydrogen orthophosphate, 5 mM HEPES and 10 mM glucose in Milli-Q water) without $Mg^{2+}$, and incubated with addition of glycine (10 µM) for 15 minutes. After the incubation, the neurons were co-treated with the test compound (dissolved in Locke's plus glycine solution) and NMDA (20 µM; Sigma) for 20 minutes. Neurons were rinsed with Locke's plus $Mg^{2+}$ and replaced with fresh growth medium. The cell death was assayed and quantified using the lactate dehydrogenase release assay (Roche) after 24 hours.

NMDA Receptor Activity Assay on Cortical Neuron Cultures (FLIPR)

Cortices from embryonic day 18 Sprague Dawley rats were removed and dissociated in cold Hanks solution without $Mg^{2+}$ and $Ca^{2+}$. Cells were plated at $3\times10^4$ per well onto clear-bottomed 96-well black plates (BD Bioscience) coated with poly-lysine. Cultures were grown in neurobasal media supplemented with 0.2% B27 (v/v) (Invitrogen). Cultures of 9 days in vitro (9DIV) to 13DIV were used for NMDA receptor activity assay. On the day of the assay, primary cultures were incubated in a balanced salt solution buffer consisting of 10 mM HEPES pH 7.4, probenecid, and the calcium sensitive fluorescent dye Fluo4-AM (Molecular Probes) (4 mM) for 1 hr at 37° C. Cells were then placed onto Fluorometric Imaging Plate Reader (FLIPR, Molecular Devices), along with a corresponding drug plate. FLIPR automatically transferred the test compounds into the wells at an injection speed of 50 µl per second. The subsequent calcium ion movements from extracellular membrane to the intracellular membrane were monitored via a fluorescent dye for 2 minutes.

FLIPR Assay Methodology using Primary Neuronal Cultures

Hippocampi from embryonic day 18 Sprague Dawley rats were removed and dissociated in cold Hanks solution without magnesium and calcium. Cells were plated onto clear bottomed black 96-well plates (BD Bioscience) coated with poly-lysine. Cultures were grown in neurobasal media supplemented with 0.2% B27 (v/v) (Invitrogen). Cultures were used from 9-13 days in vitro for NMDA receptor activity assay. On the day of the assay, primary cultures were incubated in a buffer consisting of 10 mM HEPES pH 7.4, probenecid, and the calcium sensitive fluorescent dye Fluo4-AM (Molecular Probes) (4 mM) for 1 h at 37° C. Cells were then placed on a FLIPR (Molecular Devices), after which test compounds were added to the cells in the presence or absence of NMDA. The change in fluorescent activity was monitored for 2 minutes. Data is represented in fold of response compared to solvent (DMSO) control. Memantine was used as a control.

Immunocytochemical Analysis of Neurons after NMDA Insult

Primary cortical and hippocampal neurons were prepared from embryonic day 18 (E18) Sprague-Dawley rats. Neurons were plated on 35-mm dishes (NUNC) at a density of $1\times10^6$ cells per plate using Neurobasal medium (Invitrogen) supplemented with 2% B27 (Invitrogen). Neurons at 11-12 days in vitro (DIV) were subjected to treatment with the test compounds. Neurons were pretreated with the test compound for 2 hours prior to NMDA treatment. 0.1 µM (+)-MK-801 Hydrogen Maleate (Sigma) was added as a positive control. Briefly, the neurons were rinsed with Locke's solution (5 mM potassium chloride, 128 mM sodium chloride, 2.7 mM calcium chloride, 1 mM di-sodium hydrogen orthophosphate, 5 mM HEPES and 10 mM glucose in Milli-Q water) without $Mg^{2+}$, and incubated with addition of glycine (10 µM) for 15 minutes. After the incubation, the neurons were co-treated with the test compound (dissolved in Locke's plus glycine solution) and NMDA (20 µM; Sigma) for 20 minutes. Neurons were rinsed with Locke's plus $Mg^{2+}$ and replaced with fresh growth medium. After incubation in culture medium for 24 hours, neurons were fixed with 4% paraformaldehyde for 20 minutes at room temperature, permeabilized and blocked with 4% goat serum and 0.4% Triton X-100. Double staining was performed by incubating the neurons with mouse monoclonal antibody specific for β tubulin isotype III (1:1000; Sigma) at 4° C. overnight followed by FITC-conjugated goat anti-mouse antibody (1:1000; Invitrogen). Neurons were counter-stained with DAPI (1:5000) to visualize nuclei before mounting. Neurons were then analyzed by a fluorescence microscope using a 40× objective (DMRA; Leica). Immunofluorescent images were acquired with a RT Slider digital camera (#2.3.1, Diagnostics Instruments), collected with SPOT software (Diagnostics Instruments) and prepared for presentation with Adobe Photoshop®.

Cell Toxicity Test

This was performed to study the effects of the invention on primary neurons. Cortical neurons isolated from embryonic day 18 Spraque-Dawley rats were cultured in Neurobasal medium supplemented with 2% B27 and penicillin/streptomycin solution (Invitrogen). Primary neurons of 7 days in culture (7 DIV) were treated with various concentrations of the invention in the absence of B27 for 24 hours. Lactate dehydrogenases (LDH) was released into the medium and measured and calculated as percentage compared to 1% Triton X-100. A basal level of LDH of approximately 20% was detected in all solvent control and no significant toxicity was observed for DA001, including the maximum dose at 70 µM.

Western Blot Detection for CREB Phosphorylation

Embryonic day 18 Sprague Dawley rat pups were decapitated and their brains were removed, and the cortices were isolated. Tissues were triturated and isolated neurons were plated onto 60 mm plate and cultured with Neurobasal medium supplemented with 2% B27 (Invitrogen). Experiments were performed after 10-12 days in vitro (DIV). Cultured cells were transferred from tissue culture medium to a HEPES perfusion solution containing 1 µM tetrodotoxin (TTX) 30 min before stimulation. Cells were stimulated with a test compound or vehicle control (DMSO) or synaptic activity cocktail (bicuculline, 50 µM; 4-aminopyridine, 200 µM; nimodipine, 5 µM; 6-cyano-7-nitroquinoxaline-2,3-dione, 10 µM) for 10 min and changed to perfusion medium with 1 µM TTX. Cells were then lysed at various time intervals with hot (95° C.) 3×SDS sample buffer and were stored at −80° C. before use. Before being loaded, the lysates were heated to 95° C. for 10 min, vortexed and centrifuged for 7 min at 15,000×g. Extracts were electrophoresed on 10% SDS-polyacrylamide gel and transblotted to nitrocellulose membrane. The membranes were washed with 5% (w/v) powdered milk dissolved in PBS with 0.1% Triton X-100, followed by incubation at 4° C. overnight with rabbit polyclonal anti-CREB phosphorylated at Ser 133 (1:1000, Cell Signaling Technology). Next, the membranes were washed and incubated with horseradish peroxidase (HRP)-conjugated secondary antibodies. The signal was visualized using ECL Western Blotting Kit. Blots were stripped and probed for total CREB expression.

Morris Water Maze 6-8 week old outbred male I.C.R. mice, weighing 25-35 g were housed two per cage in a climatically controlled animal room (23-25° C.) under 12 hours light/dark cycling. The animals were allowed access to water and food ad lib. The mice used for the experiment were brought to particular laboratory conditions for two days. All the experiments were conducted between 14:00 and 18:00. Scopolamine hydrobromide (Sigma, USA) was dissolved in saline in 0.1 mg/kg and administered in a volume of 10 ml/kg body weight. The experimental mice were randomly assigned into 4 or 6 groups, each consisting of 12 mice with similar mean body weights and age. The test compound was dissolved in physiological saline before the experiments each day. Scopolamine (0.1-4 mg/kg) was administrated through intraperitoneal injection (i.p.) at 30 minutes before the swimming tasks to induce memory deficit. Oral administrations (p.o.) of the sample (0.1, 0.2, 0.4, 30 and 100 mg/kg), or its saline (0.9% NaCl) was initiated at the first day of the task and administrated according to a volume of 10 ml/kg body weight. Oral administrations were given 45 minutes before the swimming tasks and performed daily for 4 consecutive days until the end of the task.

Each mouse was subjected to 4 trials per day for 5 consecutive days. A trial began when a mouse held facing the pool wall was immersed in the water. The mouse was then allowed 60 seconds to search for the platform. If the mouse failed to escape within this time period, it was guided and placed on the platform. Regardless of whether the mouse found the platform or not, it remained there for 20 seconds. There was a 30 seconds recovery period between trials. The 4 trials were started from the 2 points (north and west) located farthest from the platform. The probe trial (without platform) was assessed within a 60 s period on the fifth day of behavioral testing (one experiment), and the time spent in the southeast quadrant where the escape platform had been set during training was recorded computationally and presented as percentage of spatial bias.

Because both the escape latency and swimming distance of mice in the behavioral experiment showed similar group differences, only the escape latency to find the platform in the water maze was used to evaluate the memory performance in the tested mice. The two-way ANOVA with repeated measures was used to analyze latency values, and calculated as the mean latency periods for each mouse. (Data are expressed as means±S.E.M. by using 2-way ANOVA). One-way ANOVA followed by Duncan's multiple-range test (data expressed as mean±S.E.M. *$P<0.05$ and **$P<0.01$ versus scopolamine) was used to analyze group differences of the data collected during probe trials.

Quantification of Spine

Cultured hippocampal neurons were prepared from embryonic day 18—rat embryos and seeded on 18 mm coverslips coated with poly-D-lysine. The neurons were then grown in Neurobasal medium (Invitrogen) supplemented with 2% B27 (Invitrogen) and 0.5 mM glutamine. To visualize the morphology of dendritic spines, the neurons were transfected with GFP DNA construct between 7-9 DIV by using calcium phosphate precipitation. To examine the development of dendritic spines, the neurons were treated with DA001 on 14 DIV. The neurons were then fixed with 4% paraformaldehyde and morphology was examined using Confocal microscopy. To quantify spine density in cultured hippocampal neurons, a stack of images (z step, 0.5 µm) was collected using a 60× objective. Images were merged and analyzed using Meta-Morph software (Universal Imaging Corp). Dendritic spines, defined as protrusions at least 0.5 µm from the dendritic surface, were scored and expressed as per □m length of dendrite. Three dendrites from each neuron was randomly selected and quantified in a double-blinded manner. For each experimental condition, twenty to thirty neurons were analyzed from 3 independent experiments. Data are presented as mean±SEM.

Quantification of Neurite Extension

Cultured cortical neurons were prepared from embryonic day 18—rat embryos and seeded on 18 mm coverslips coated with poly-D-lysine. The neurons were then grown in Neurobasal medium (Invitrogen) supplemented with 2% B27 (Invitrogen). DA001 was added to ODIV cultured cells and incubated for 48 hours. The neurons were then fixed with 4% paraformaldehyde and immunostained with anti-Tau antibody and anti-MAP2 antibody which detected axon and dendrites, respectively. Morphology was examined using Confocal microscopy. The length of the longest axon was traced using MetaMorph Ver 5.0r1 software (Universal Imaging Corp.). For each measurement, at least 50 cells were counted from randomly selected fields and n=3 cultures. Each experiment was repeated three times.

Cortical Neuron Survival Assay Against NMDA (N-Methyl-D-Aspartate) Excitotoxicity Cortical neurons were prepared from embryonic day 18 Sprague-Dawley rats. After the cortices had been removed from the brain, isolated cells were plated onto Poly d-Lysine (PDL) (P0899, Sigma)-coated 48 well plates (150687, NUNC) at a density of $2\times10^5$ cell per well using Neurobasal Medium (NB) (21103-049, Gibco) with B27 supplement (17504-044, Gibco), penicillin/streptomycin (15140, Gibco) and 1 mM L-glutamine (25030, Gibco). The cell culture was incubated at 37° C. in a humidified atmosphere of 5% $CO_2$ in air. Medium was changed to growth medium (Neurobasal Medium with penicillin/streptomycin and B27 supplement) after 3 hours. Half medium was changed with growth medium every 2-3 days to maintain the cells until day 10 in vitro (10DIV). Serial dilutions of samples were prepared in growth medium and 0.1 µM (+)-Hydrogen Maleate (MK-801) (M-107, Sigma) was used as positive control. For pre-treating assay, half of the medium was removed from wells, and equal amount of diluted samples were replaced. Cells were then incubated for 2 hours at 37° C. in a humidified atmosphere of 5% CO$_2$ in air. Culture was subsequently rinsed with Locke's solution (5 mM potassium chloride, 128 mM sodium chloride, 2.7 mM calcium chloride, 1 mM di-sodium hydrogen orthophosphate, 5 mM HEPES and 10 mM Glucose in Milli-Q water), then incubated with Locke's solution in the presence of glycine (10 µM) for 15 minutes before N-Methyl-D-Aspartic Acid (NMDA) (M-3262, Sigma) treatment. NMDA (20 µM) dissolved in Locke's plus glycine solution was then substituted and incubated for 20 minutes at 37° C. For co-treated NMDA assay, serial dilutions of samples were prepared in Locke's solution plus glycine and 20 µM NMDA solution and incubated for 20 minutes at 37° C., 5% CO$_2$. Afterwards, cells were incubated in growth medium for 18-24 hours and detected with Cytotoxicity Detection Kit (1644793, Roche).

Cortical Neuron Survival Assay Against Glutamate Excitotoxicity

Cortical neurons were prepared from embryonic day 18 Sprague-Dawley rats. After the cortices had been removed from the brain, isolated cells were plated onto Poly d-Lysine (PDL) (P0899, Sigma)-coated 48 well plates (150687, NUNC) at a density of $2 \times 10^5$ cell per well using Neurobasal Medium (NB) (21103-049, Gibco) with B27 supplement (17504-044, Gibco), penicillin/streptomycin (15140, Gibco) and 1 mM L-glutamine (25030, Gibco). The cell culture was incubated at 37° C. in a humidified atmosphere of 5% CO$_2$ in air. Medium was changed to growth medium (Neurobasal Medium with penicillin/streptomycin and B27 supplement) after 3 hours. Half medium was changed with growth medium every 2-3 days to maintain the cells until day 10 in vitro (DIV10). Serial dilutions of samples were prepared in growth medium and 0.1 µM (+)-Hydrogen Maleate (MK-801) (M-107, Sigma) was used as positive control. For pre-treating assay, half of the medium was removed from wells, and equal amount of diluted samples were replaced. Cells were then incubated for 2 hours at 37° C. in a humidified atmosphere of 5% CO$_2$ in air. Culture was subsequently rinsed with Locke's solution (5 mM potassium chloride, 128 mM sodium chloride, 2.7 mM calcium chloride, 1 mM di-sodium hydrogen orthophosphate, 5 mM HEPES and 10 mM Glucose in Milli-Q water), then incubated with Locke's solution in the presence of glycine (10 µM) for 15 minutes before N-Methyl-D-Aspartic Acid (NMDA) (M-3262, Sigma) treatment. NMDA (20 µM) dissolved in Locke's plus glycine solution was then substituted and incubated for 20 minutes at 37° C. For co-treated NMDA assay, serial dilutions of samples were prepared in Locke's solution plus glycine and 20 µM NMDA solution and incubated for 20 minutes at 37° C., 5% CO$_2$. Afterwards, cells were incubated in growth medium for 18-24 hours and detected with Cytotoxicity Detection Kit (1644793, Roche).

Middle Carotid Artery Occlusion Model

Sprague Dawley rat (8-week old and 300 g) were housed in groups of 8 with water and standard rodent chow ad libitum, and were kept under controlled conditions at temperature of 20° C. and on a 07:00-19:00 light cycle. Experiments were conducted between 09:00-12:00. The study design and the experimental protocols were conducted in accordance to the local institutional guidelines for the care and use of laboratory animals. The test compound was dissolved in distilled-deionised water to give an intraperitoneal injection volume of 4 ml/kg. Transient focal ischemia was induced using an intraluminal technique where a filament was introduced from the common carotid artery into the internal carotid artery and advanced into the arterial circle, thereby occluding the middle cerebral artery. Two hours after induction of ischemia, the filament was removed and reperfusion was allowed for 22 hours. The novel compounds were then administered at different times and at various dosages.

To identify potential protective or detrimental effects of the novel compound on the test subject, a four-point scale neurological scoring system (Mann Whitney U test) was employed. The severity of neurological deficits was examined after 22 hours reperfusion: (0) no observable neurological deficits (normal); (1) failure to extend the left forepaw fully (mild); (2) circling to the contralateral side (moderate); and (3) loss of walking and righting reflex (severe).

The rats were then sacrificed by cervical dislocation and the brain was coronally sectioned into five pieces, each 2-mm thick, by placing the whole brain onto the brain mold from rostral to caudal. The slices were stained with 2% 2,3,5-triphenyltetrazolium chloride (TTC) (Sigma, USA) in the dark under 37° C. for 10 minutes and fixed overnight with 10% formalin in phosphate buffer solution [pH 7.4]. The infarct area of each posterior surface was analyzed by an image analysis program (Sigma Scan Pro 5.0, Statistics Package for the Social Sciences; SPSS, Inc., Chicago, Ill., U.S.A.). The percentage of infarct area and volume were calculated and presented as the percentage of the infarct area of the contralateral hemisphere to eliminate the contribution of edema to the ischemic lesion. Hemispheric brain swelling was calculated as follow (ipsilateral volume−contralateral volume)/contralateral volume X 100%. The statistical significance of the results was determined by Mann-Whitney U test, and $P < 0.05$ was considered significant. Values were expressed as mean±SEM.

RNA Extraction, cDNA Synthesis, and Real-Time Quantitative PCR

Cortical neurons of 11DIV-12DIV were pre-incubated with DA001 or DMSO for 24 hours. Cells were washed in Locke's medium without magnesium for 15 min, followed by the treatment of NMDA (20 µM) or water for 20 min. Neurons were incubated with normal growth medium and total RNA were extracted at different time intervals after treatment. Total RNA was extracted using RNeasy Mini kit (Qiagen) according to the manufacturer's protocol, and was reverse-transcribed into single-stranded cDNA with SuperScript II Reverse Transcriptase (Invitrogen) and oligo-dT primers. Real-time Quantitative PCR was performed using Power SYBR Green PCR Master Mix (Applied Biosystems) on the Mx3000P Real-Time PCR System (Stratagene). Thermal cycling was initiated with a 10-min denaturation step at 95° C., followed by 40 cycles of 95° C. for 30 sec, 60° C. for 1 min and 72° C. for 30 sec. The final product was subjected to a Meltcurve detection at the end of the reaction. Regulation of the gene expression was normalized against home gene, hypoxanthine phosphoribosyltransferase 1 (HPRT1) and glyceraldehyde 3-phosphate dehydrogenase (GAPDH). Real-time PCR primers are as follows.

| | | |
|---|---|---|
| BDNF Forward: | TTGAGCACGTGATCGAAGAG | (SEQ ID NO: 2) |
| BDNF Reverse: | CCAGCAGAAAGAGCAGAGGA | (SEQ ID NO: 3) |
| NT-3 Forward: | GGGGGATTGATGACAAACAC | (SEQ ID NO: 4) |
| NT-3 Reverse: | ACAAGGCACACACACAGGAA | (SEQ ID NO: 5) |
| Bcl-2 Forward: | ATAACCGGGAGATCGTGATG | (SEQ ID NO: 6) |
| Bcl-2 Reverse: | CAGGCTGGAAGGAGAAGATG | (SEQ ID NO: 7) |
| c-fos Forward: | GGAGCCGGTCAAGAACATTA | (SEQ ID NO: 8) |
| c-fos Reverse: | TGCTGCATAGAAGGAACCAG | (SEQ ID NO: 9) |

```
HPRT1 Forward:  TGACACTGGTAAAACAATGCA (SEQ ID NO: 10)

HPRT1 Reverse:  GGTCCTTTTCACCAGCAAGCT (SEQ ID NO: 11)

GAPDH Forward:  TGCACCACCAACTGCTTAGC  (SEQ ID NO: 12)

GAPDH Reverse:  GGCATGGACTGTGGTCATGAG (SEQ ID NO: 13)
```

Forced Swim Test (FST)

Outbred male I.C.R. mice of 5-weeks old weighing 22-26 g were used. The mice had free access to food (rodent chow #2053, 5 g/mouse/day) and water. The cage floors were covered with wood shavings and the mice were handled once per week while the cages were cleaned. Mice were randomly assigned into 3 groups: group 1—DA001; group 2—Vehicle; group 3—imipramine. Number of mice per group was ~10. To facilitate adaptation to novel surroundings, mice were transported to the testing area from the core animal facility at least one week prior to testing. All experimental sessions were conducted in the morning between 9:00 am to 12:00 pm. Briefly, mice were put into a pyrex cylinder of 30 cm in height and 11.5 cm in diameter. Mice were put into the cylinder with water (10 cm) to a level that they would not be able to touch the bottom for a 6-min time frame. FST experiments were conducted using Etho-Vision® XT Mobility detection, Noldus. This parameter can be used to score the behavior of animals in the Porsolt Swim Test (PST), automatically. DA001 was orally administered at 24 hour and 45 min before the swimming session. Mice were fasted for 12 hours before testing.

Although the foregoing invention has been described in some detail by way of illustration and example for purposes of clarity of understanding, one with skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A compound of the following structure:

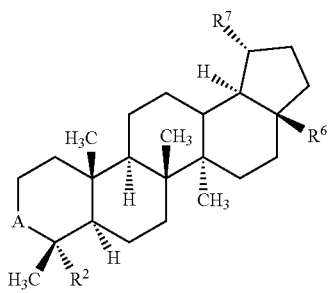

or a pharmaceutically acceptable salt, isomer thereof; wherein:

$R^2$ is $C_{1-6}$alkyl, $C_{1-6}$haloalkyl or $C_{3-6}$cycloalkyl substituted with 1-3 hydroxyl groups; wherein $R^a$, $R^b$, $R^c$ and $R^d$ are each independently H, $C_{1-6}$alkyl or aryl-$C_{1-6}$alkyl; wherein $R^f$ is selected from the group consisting of halo, CN, $NO_2$, —OH, —$R^g$, —$OR^g$, —OC(O)NHR$^g$, —OC(O)N($R^g$)$_2$, —OC(O)$R^g$, —OC(O)H, —$NH_2$, —NHR$^g$, —N($R^g$)$_2$, —SH, —SR$^g$, —S(O)$_2$R$^g$, —SO$_2$NH$_2$, —SO$_2$NHR$^g$, —SO$_2$N($R^g$)$_2$, —NHS(O)$_2$R$^g$, —NR$^g$S(O)$_2$R$^g$, —C(O)NH$_2$, —C(O)NHR$^g$, —C(O)N($R^g$)$_2$, —C(O)H, —C(O)R$^g$, —NHC(O)R$^g$, —NR$^g$C(O)R$^g$, —NHC(O)NH$_2$, —NR$^g$C(O)NH$_2$, —NR$^g$C(O)NHR$^g$, —NHC(O)NHR$^g$, —NR$^g$C(O)N(R$^g$)$_2$, —NHC(O)N(R$^g$)$_2$, —COOH, —CO$_2$R$^g$, —NHCO$_2$R$^g$, —NR$^g$CO$_2$R$^g$ and —OSi(R$^g$)$_3$, wherein each R$^g$ is independently a $C_{1-6}$alkyl;

A is selected from the group consisting of C=Y$^1$, C=NOR$^c$, C=NOC(O)H, C=NOC(O)R$^g$, C=NOCO$_2$R$^g$, C=NOC(O)NH$_2$, C=NOC(O)NHR$^g$, C=NOC(O)N(R$^g$)$_2$ and —CR$^c$R$^h$, wherein Y$^1$ is =O or =S, and R$^h$ is selected from the group consisting of halo, CN, NO$_2$, —OH, —OR$^i$, —OC(O)NHR$^i$, —OC(O)N(R$^i$)$_2$, —OC(O)R$^i$, —OC(O)H, —NH$_2$, —NHR$^i$, —N(R$^i$)$_2$, —SH, —SR$^i$, —S(O)$_2$R$^i$, —SO$_2$NH$_2$, —SO$_2$NHR$^i$, —SO$_2$N(R$^i$)$_2$, —NHS(O)$_2$R$^i$, —NR$^i$S(O)$_2$R$^i$, —C(O)NH$_2$, —C(O)NHR$^i$, —C(O)N(R$^i$)$_2$, —C(O)H, —C(O)R$^i$, —NHC(O)R$^i$, —NR$^i$C(O)R$^i$, —NHC(O)NH$_2$, —NR$^i$C(O)NH$_2$, —NR$^i$C(O)NHR$^i$, —NHC(O)NHR$^i$, —NR$^i$C(O)N(R$^i$)$_2$, —NHC(O)N(R$^i$)$_2$, —COOH, —CO$_2$R$^i$, —NHCO$_2$R$^i$, —NR$^i$CO$_2$R$^i$, —OSi(R$^i$)$_3$, —O—(Z)$_{1-6}$, —S—(Z)$_{1-6}$, —NH(Z)$_{1-6}$ and —NR$^c$(Z)$_{1-6}$, wherein each R$^i$ is independently a $C_{1-6}$alkyl, $C_{1-6}$haloalkyl, aryl$C_{0-6}$alkyl or $C_{3-6}$cycloalkyl, optionally substituted with from 1-3 R$^f$ groups; —(Z)$_{1-6}$ is a sequence of 1-6 independently selected $C_{4-7}$monosaccharide residues linked together through ether bonds, optionally each Z is independently substituted with from 1-3 R$^f$ groups and A is other than CH—OC(O)C$_{1-6}$alkyl;

R$^6$ is selected from the group consisting of $C_{1-6}$haloalkyl, $C_{3-6}$cycloalkyl, —X$^2$CN, —X$^2$NO$_2$, —X$^2$C(O)R$^a$, —X$^2$OC(O)R$^a$, —CR$^b$=NOR$^c$, —X$^2$CO$_2$R$^c$, —X$^2$C(O)NR$^c$R$^d$, —X$^2$C(NR$^c$R$^d$)=NR$^c$, —X$^2$C(O)NR$^c$S(O)R$^d$, —X$^2$C(O)NR$^c$S(O)$_2$R$^d$, —X$^2$OR$^a$, —X$^2$SR$^a$—X$^2$NHR$^a$ and —X$^2$N(R$^a$)$_2$, wherein each X$^2$ is independently a bond or C$_{1-4}$-alkylene; wherein the aliphatic portion of R$^6$ substituent is optionally substituted with from 1-3 R$^f$ groups, wherein the two adjacent R$^f$ substituents together with the atoms to which they are attached optionally form a 5-membered heterocyclic ring having from 1-3 heteroatoms selected from N, O or S, wherein the heterocyclic ring is optionally substituted with from 1-3 R$^g$ groups, and the aromatic ring of R$^6$ is optionally substituted with from 1-5 R$^f$ groups; and $R^7$ is selected from the group consisting of $C_{1-6}$alkyl, $C_{1-6}$haloalkyl, $C_{3-6}$cycloalkyl, $C_{2-6}$alkenyl, $C_{2-6}$haloalkenyl, $C_{5-6}$cycloalkenyl and $C_{2-6}$epoxyalkyl, each of which is optionally substituted with from 1-3 $R^f$ groups;
with the proviso that the compounds are other than
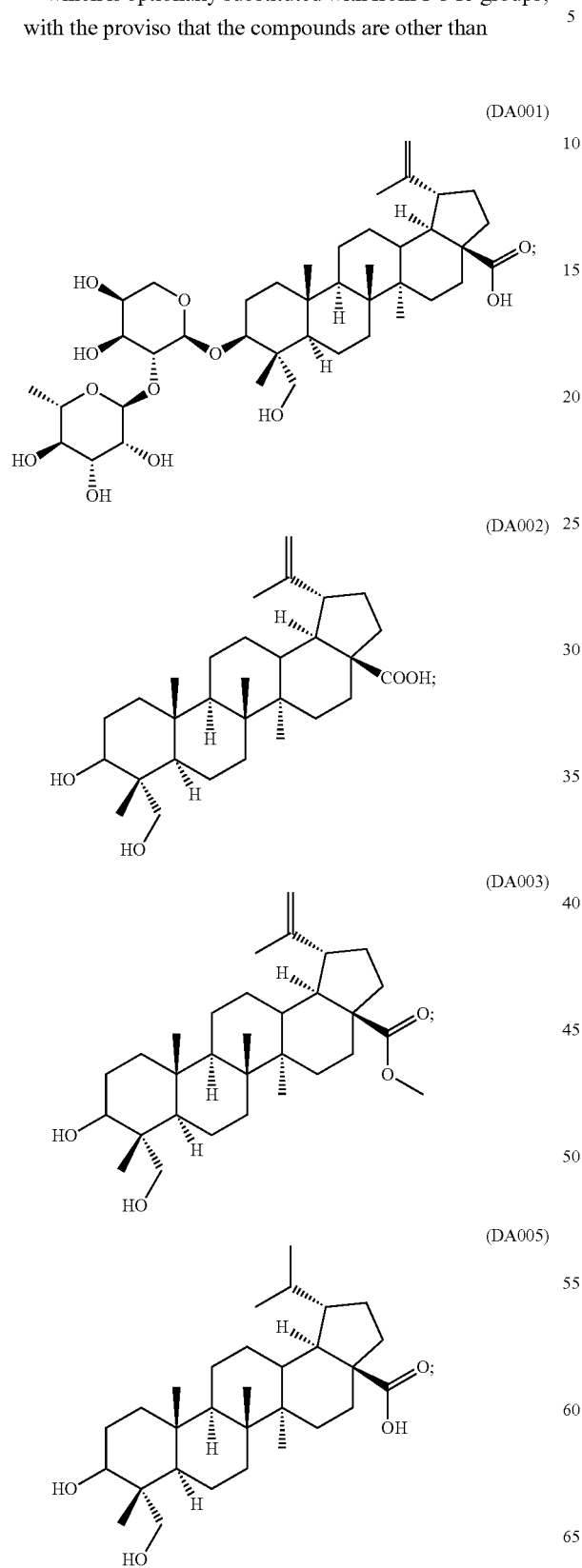
(DA001)
(DA002)
(DA003)
(DA005)
-continued
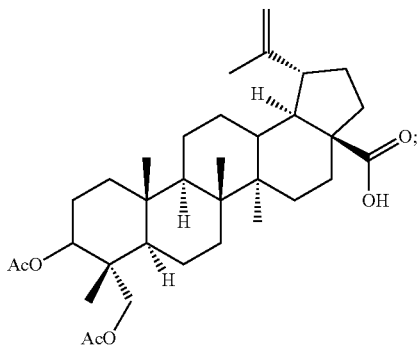
(DA006)
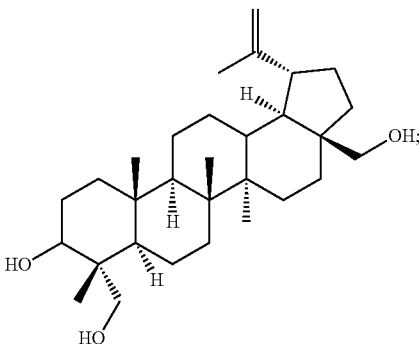
(DA010)
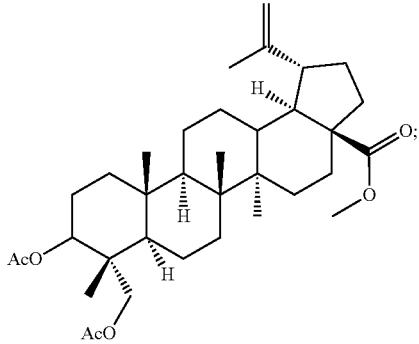
(DA011)
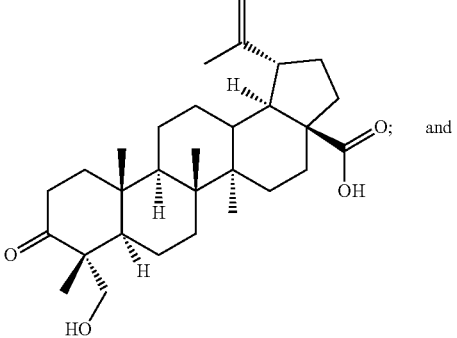
(DA018)
and -continued

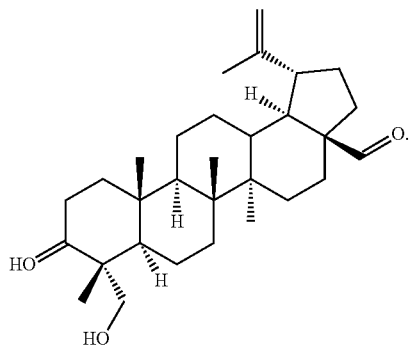
(DA020)

2. The compound of claim 1, wherein $R^2$ is $C_{1-6}$alkyl substituted with a hydroxyl group.

3. The compound of claim 2, wherein $R^2$ is —$CH_2OH$.

4. The compound of claim 1, wherein $R^2$ is selected from the group consisting of —$CH_2OH$.

5. The compound of claim 1, wherein $R^7$ is ethylene oxide radical, optionally substituted with 1-3 $R^f$ groups.

6. The compound of claim 5, wherein $R^7$ is propylene oxide radical, optionally substituted with 1-3 $R^f$ groups.

7. A method of enhancing the brain's cognitive function in a mammal, where said brain cognitive function is associated with neuronal cell death or cytotoxicity induced or caused by N-methyl D-aspartate (NMDA) receptor activity, said method comprising: administering to said mammal a therapeutically effective amount of a compound of claim 1.

8. A method of reducing neuronal cell death induced or caused by NMDA receptor activity in a mammal, said method comprising: administering to said mammal a therapeutically effective amount of a compound of claim 1.

9. A pharmaceutical composition comprising a compound of claim 1 and a pharmaceutically acceptable carrier, excipient or diluent.

* * * * *